US008119589B2

(12) United States Patent
Anguita

(10) Patent No.: US 8,119,589 B2
(45) Date of Patent: Feb. 21, 2012

(54) MODULATION OF CD4+ T CELL RESPONSES BY A TICK SALIVA PROTEIN, SALP15 AND POLYPEPTIDES DERIVED THEREFROM

(75) Inventor: Juan Anguita, Florence, MA (US)

(73) Assignee: University of North Carolina at Charlotte, Charlotte, NC (US)

( * ) Notice: Subject to any disclaimer, the term of this patent is extended or adjusted under 35 U.S.C. 154(b) by 781 days.

(21) Appl. No.: 11/667,748

(22) PCT Filed: Sep. 14, 2005

(86) PCT No.: PCT/US2005/032843
§ 371 (c)(1),
(2), (4) Date: Aug. 1, 2008

(87) PCT Pub. No.: WO2006/055077
PCT Pub. Date: May 26, 2006

(65) Prior Publication Data
US 2008/0305997 A1 Dec. 11, 2008

Related U.S. Application Data

(60) Provisional application No. 60/627,122, filed on Nov. 12, 2004.

(51) Int. Cl.
*C07K 14/00* (2006.01)
(52) U.S. Cl. .......................................... 514/1; 530/300
(58) Field of Classification Search ....... 514/1; 530/300
See application file for complete search history.

(56) References Cited

U.S. PATENT DOCUMENTS
5,741,488 A * 4/1998 Feldman et al. ............ 424/154.1
2001/0046499 A1 11/2001 Kantor et al.

FOREIGN PATENT DOCUMENTS
WO WO0140469 6/2001

OTHER PUBLICATIONS

Van Oosten et al. 1997; Treatment of multiple sclerosis with the monoclonal anti-CD4 antibody cM-T412: results of a randomized, double-blind, placebo-controlled MR-monitored phase II trial. Neurology 49:351-357.*
Iwatani et al. 1993; Intrathyroid lymphocyte subsets, including unusual CD4+CD8+ cells and CD3loTCRgblo/−CD4−CD8-cells, in autoimmune thyroid disease. Clin Exp. Immunol. 93: 430-436.*
Liu et al. 2003. Nondepleting anti-CD4 monoclonal antibody prevents diabetes and blocks induction of insulin autoantibodies following insulin peptide B:9-23 immunization in the NOD mouse. J. Autoimmunity. 21: 213-219.*
Morris et al. 1993; Increase in activated T cells and reduction in suppressor/cytotoxic T cells in acute rheumatic fever and active rheumatic heart disease: a longitudinal study. J. Infectious Diseases. 167: 979-983.*

Otomo et al. 2001; Organ transplant specificity of tolerance to skin grafts with heart or kidney grafts plus nondepleting anti-CD4 monoclonal antibody (RIB 5/2) and intravenous donor alloantigen administration. J. Surgical Research. 98(1): 59-65.*
Prinz et al. 1996. Treatment of severe cutaneous lupus erythematosus with a chimeric CD4 monoclonal antibody, cM-T412. J. Am. Acad. Dermatol. 34:244-252.*
Anguita et al., "Salp15, an Ixodes scapularis Salivary Protein, Inhibits CD4+ T Cell Activation," Immunity. vol. 16, pp. 849-859 (Jun. 2002).
Bank and Chess, "Perturbation of the T4 molecule transmits a negative signal to T cells," J. Exp. Med., vol. 162, pp. 1294-1303 (1985).
Benjamin et al., "Induction of tolerance by monoclonal antibody therapy," Nature, vol. 320, pp. 449-451 (1986).
Briand et al., "Binding of HIV-1 to its receptor induces tyrosine phosphorylation of several CD4-associated proteins, including the phosphatidylinositol 3-kinase," Virology, vol. 228, pp. 171-179 (1997).
Burgdorfer et al., "Lyme disease-a tick-borne spirochetosis?" Science, vol. 216, No. 4552, pp. 1317-1319 (1982).
Bustelo, "Regulatory and Signaling Properties of the Vav Family," Mol. Cell. Biol., vol. 20, No. 5, pp. 1461-1477 (2000).
Chen et al., "Identification of a granulocytotropic *Ehrlichia* species as the etiologic agent of human disease," J. Clin. Microbiol., vol. 32, pp. 589-595 (1994).
Crespo et al., "Phosphotyrosine-dependent activation of Rac-1 GDP/GTP exchange by the vav proto-oncogene product," Nature, vol. 385, pp. 169-172 (1997).
Ferreira and Silva, "Saliva of *Rhipicephalus sanguineus* tick impairs T cell proliferation and IFN-γ-induced macrophage microbicidal activity," Vet. Immunol. Immunopathol., vol. 64, pp. 279-293 (1998).
Hannier et al., "*Ixodes ricinus* tick salivary gland extract inhibits IL-I0 secretion and, CD69 expression by mitogen-stimulated murine splenocytes and induces hyporesponsiveness in B lymphocytes," Parasite Immunology, vol. 25, pp. 27-37 (2003).
Harding et al., "A Therapeutic CD4 Monoclonal Antibody Inhibits TCR-ζ Chain Phosphorylation, ζ-Associated Protein of 70-kDa Tyr319 Phosphorylation, and TCR Internalization in Primary Human T Cells," J. Immunol., vol. 169, No. 1, pp. 230-238 (2002).

(Continued)

*Primary Examiner* — Karen Carlson
(74) *Attorney, Agent, or Firm* — Jenkins, Wilson, Taylor & Hunt, P.A.

(57) ABSTRACT

Salp15, biologically functional equivalents and fragments thereof, and nucleic acid molecules encoding the same are disclosed. Recombinant host cells, recombinant nucleic acids and recombinant proteins are also disclosed. Salp15 gene products and Salp15 polypeptide fragments have biological activity in modulating CD4+ T cell activation through specific binding to CD4. Thus, therapeutic methods involving modulating T cell activation using Salp15 and biologically active polypeptide fragments thereof are also disclosed. The specific binding of Salp15 and fragment peptides thereof to CD4 can inhibit HIV infection of T cells, and thus methods of using Salp15 for inhibiting HIV infection are also disclosed. Screening methods for selecting substances having an ability to modulate activation of T cells are also disclosed.

8 Claims, 14 Drawing Sheets

OTHER PUBLICATIONS

Horejsi et al., "Transmembrane adaptor proteins: organizers of immunoreceptor signaling," Nat. Rev. Immunol., vol. 4, pp. 603-616 (2004).

Kopecky and Kuthejlova, "Suppressive effect of *Ixodes ricinus* salivary gland extract on mechanisms of natural immunity in vitro," Parasite Immunology, vol. 21, pp. 351-356 (1999).

Laub et al., "Anti-Human CD4 Induces Peripheral Tolerance in a Human CD4+, Murine CD4−, HLA-DR+ Advanced Transgenic Mouse Model," J. Immunol., vol. 169, pp. 2947-2955 (2002).

McDougal et al., "Binding of HTLV-III/LAV to $T_4$+ cells by a complex of the 110K viral protein and the $T_4$ molecule," Science, vol. 231, p. 382-385 (1986).

Ramamoorthi et al., "The Lyme disease agent exploits a tick protein to infect the mammalian host," Nature, vol. 436, pp. 573-577 (2005).

Notification of Transmittal of the International Search Report and the Written Opinion of the International Searching Authority, or the Declaration corresponding to International Application No. PCT/US05/32843 dated Dec. 5, 2008.

Notification of Transmittal of International Preliminary Report on Patentability corresponding to corresponding to International Application No. PCT/US05/32843 dated Jan. 29, 2009.

Ribeiro et al., "Purification and characterization of prolixin S (nitrophorin 2), the salivary anticoagulant of the blood-sucking bug *Rhodnius prolixus*," Biochem. J., vol. 308, pp. 243-249 (1995).

Riteau et al., "Vav1 Phosphorylation Is Induced by β2 Integrin Engagement on Natural Killer Cells Upstream of Actin Cytoskeleton and Lipid Raft Reorganization," J. Exp. Med., vol. 198, pp. 469-474 (2003).

Schoeler et al., "*Ixodes scapularis*: effects of repeated infestations with pathogen-free nymphs on macrophage and T lymphocyte cytokine responses of BALB/c and C3H/HeN mice," Exp. Parasitol., vol. 92, pp. 239-248 (1999).

Urioste et al., "Saliva of the Lyme disease vector, *Ixodes dammini*, blocks cell activation by a nonprostaglandin E2-dependent mechanism," J. Exp. Med., vol. 180, pp. 1077-1085.

Veri et al., "Membrane Raft-Dependent Regulation of Phospholipase Cγ-1 Activation in T Lymphocytes," Mol. Cell. Biol., vol. 21, pp. 6939-6950 (2001).

Villalba et al., "Vav1/Rac-dependent actin cytoskeleton reorganization is required for lipid raft clustering in T cells," J. Cell. Biol., vol. 155, pp. 331-338 (2001).

Wikel, "Tick modulation of host immunity: an important factor in pathogen transmission," Int. J. Parasitol., vol. 29, pp. 851-859 (1999).

Wikel and Bergman, "Tick-host immunology: Significant advances and challenging opportunities," Parasitology Today, vol. 13, pp. 383-389 (1997).

Wulfing, "The Vav Exchange Factor Is an Essential Regulator in Actin-Dependent Receptor Translocation to the Lymphocyte-Antigen-Presenting Cell Interface," Proc. Natl. Acad. Sci. USA., vol. 97, pp. 10150-10155 (2000).

Kopecky and Kuthejlova (1998). Parasite Immunol. 20:169-74.

Moore et al. (1992). J. Virol. 66:4784-4793.

Chirmule et al. (1999) CD4-mediated signals induce T cell dysfunction in vivo. *J Immunol.* 163(2):644-649.

* cited by examiner

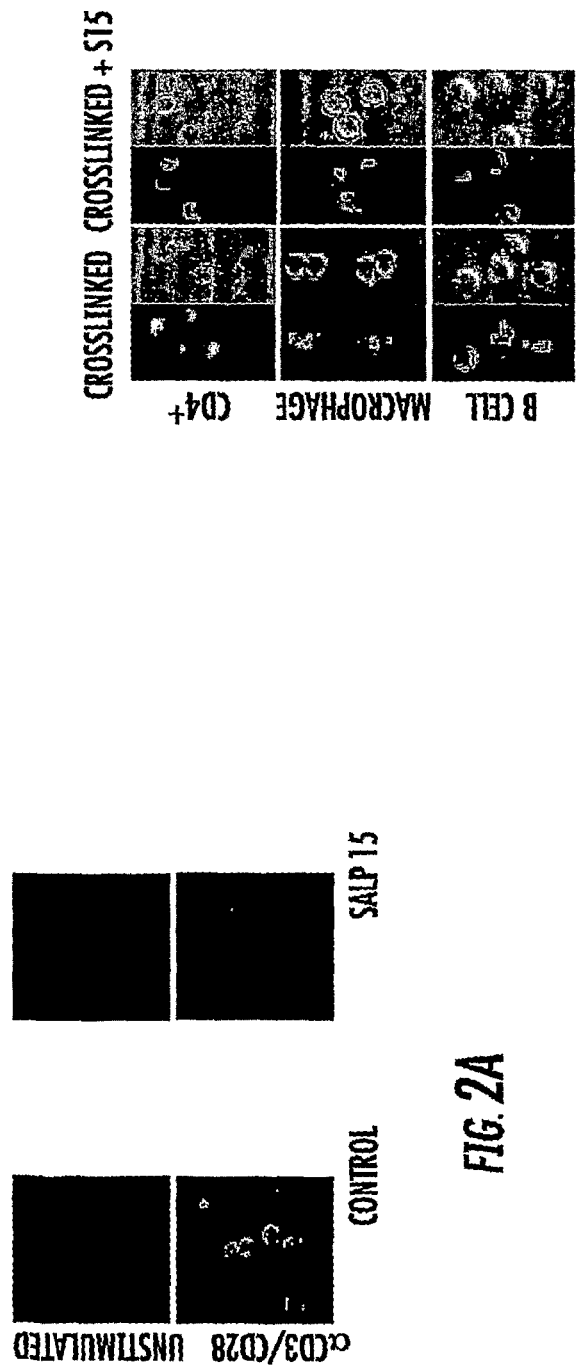
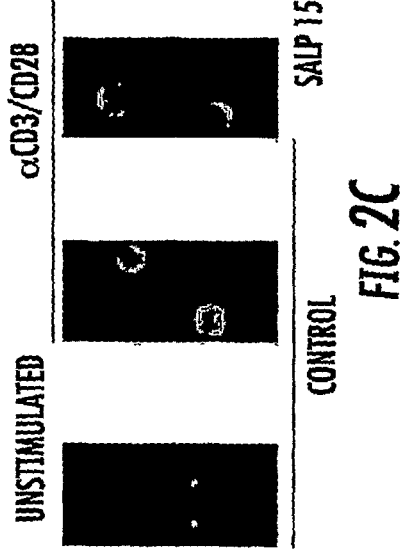
FIG. 2A
FIG. 2B
FIG. 2C

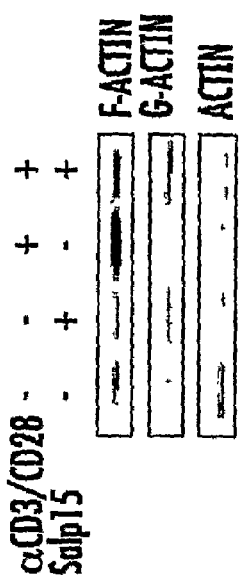
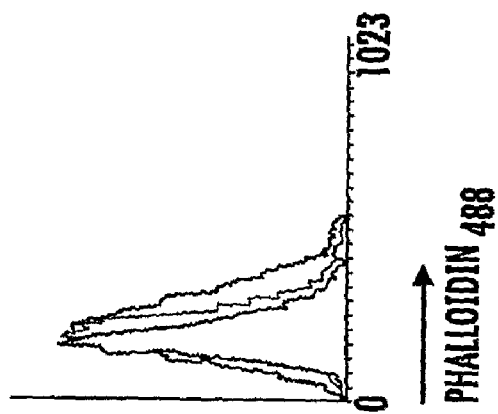
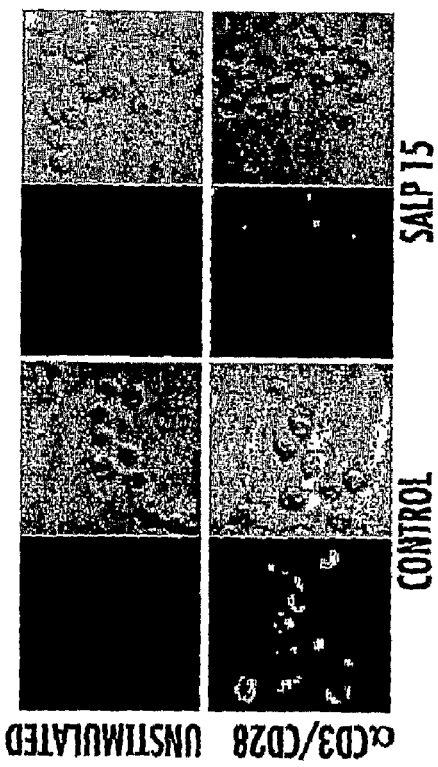

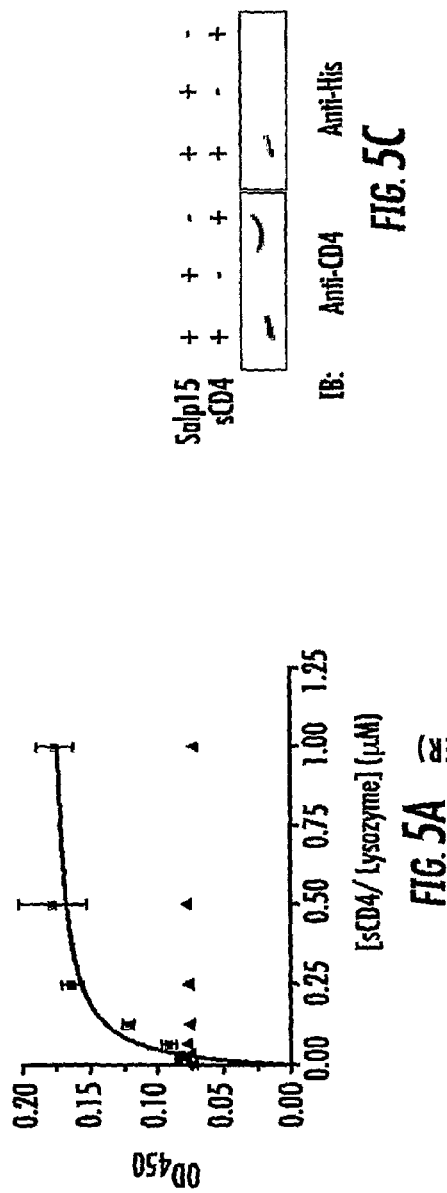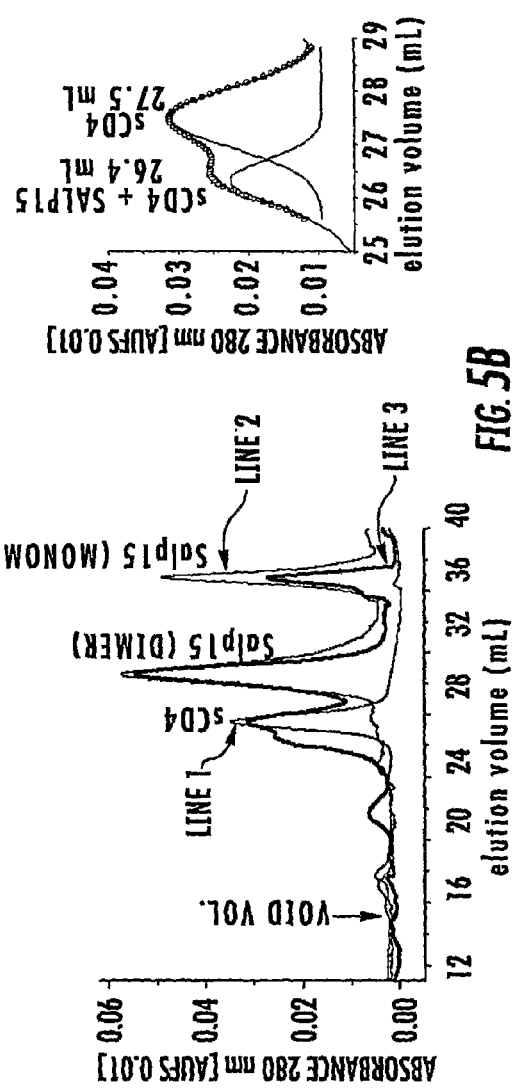

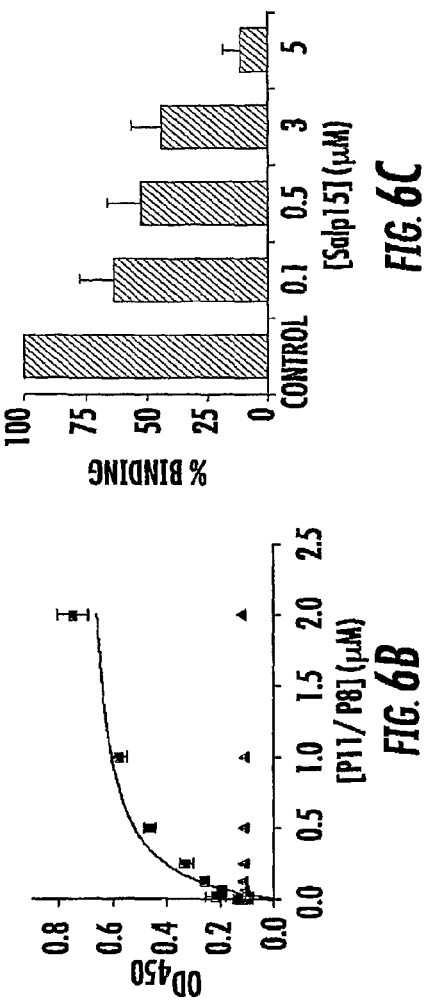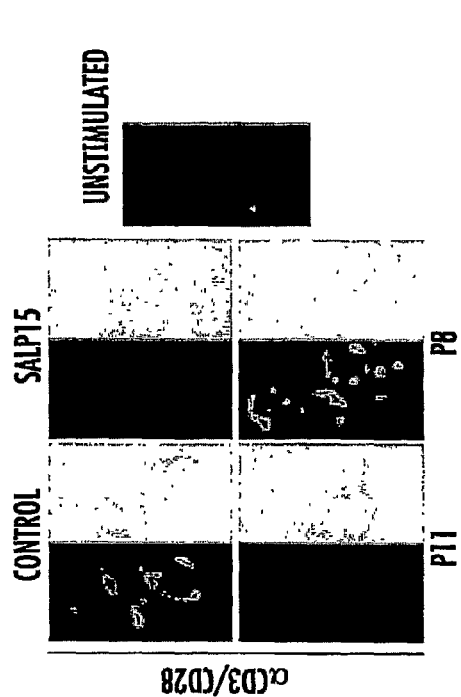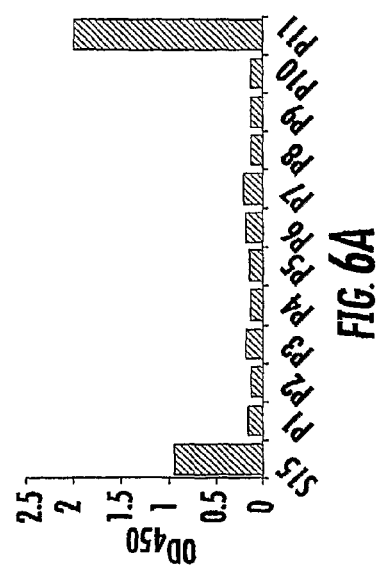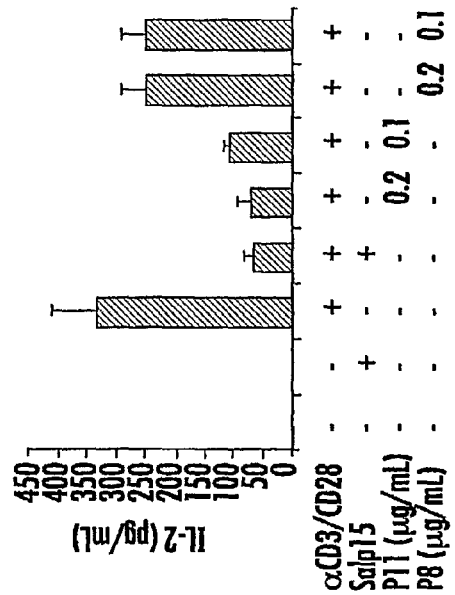

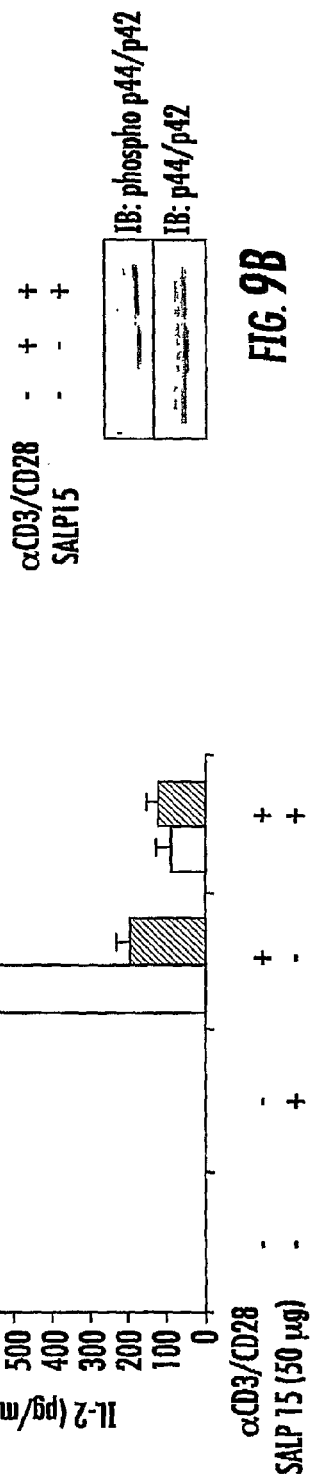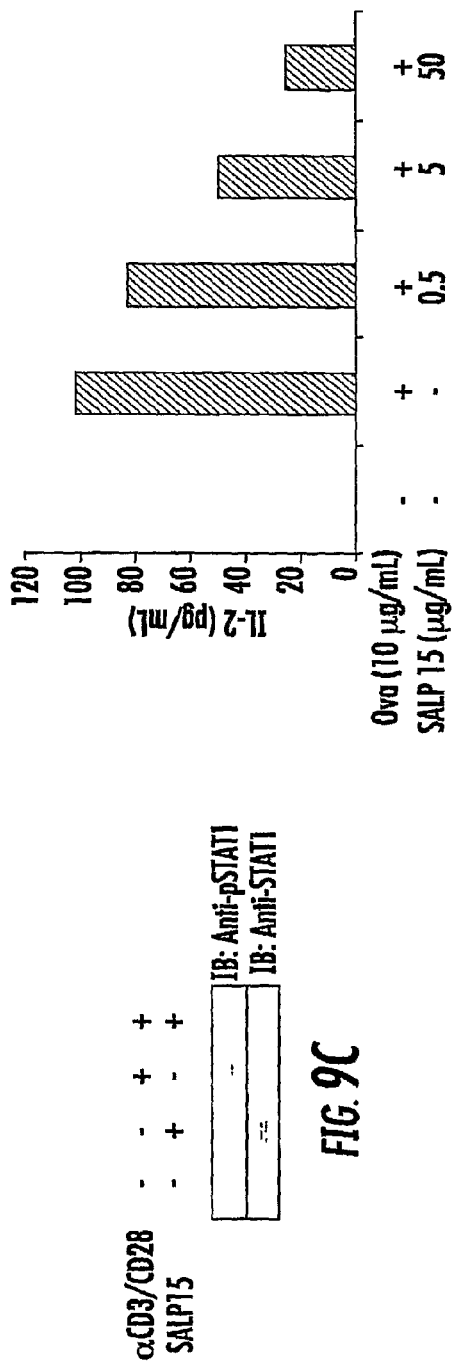
FIG. 9A
FIG. 9B
FIG. 9C
FIG. 9D

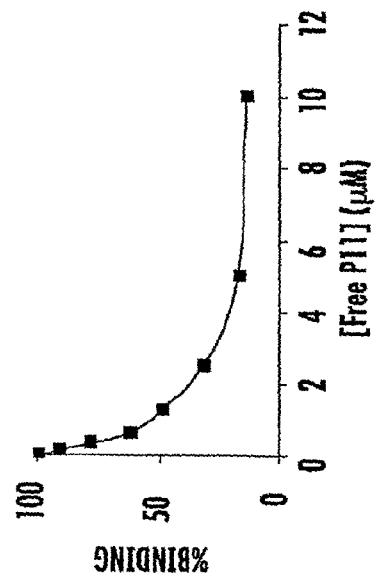
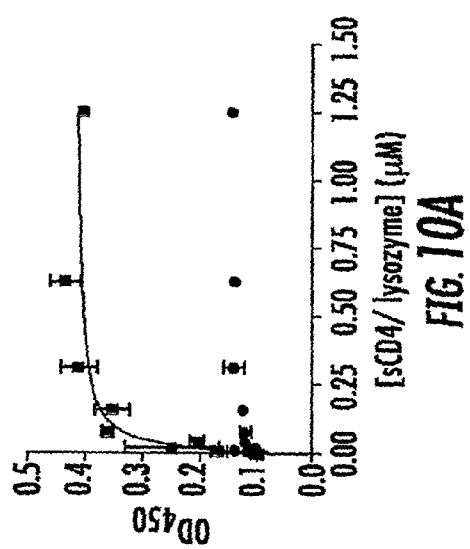
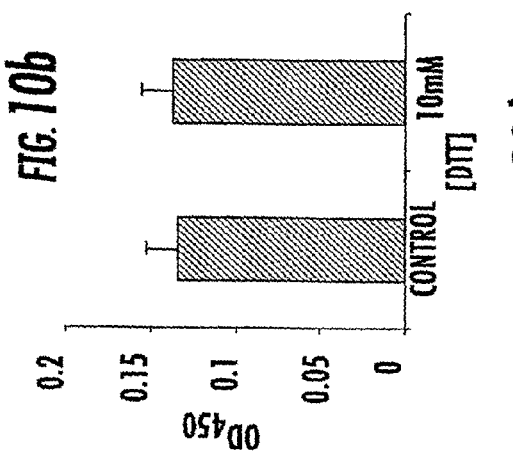
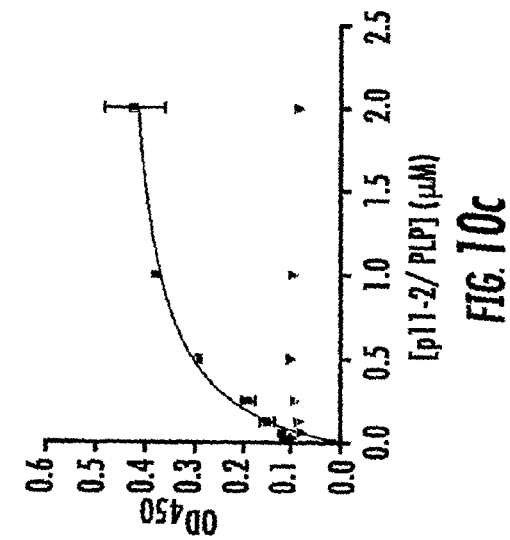

SEQUENCE LISTING

<160> NUMBER OF SEQ ID NOS: 19

<210> SEQ ID NO 1
<211> LENGTH: 408
<212> TYPE: DNA
<213> ORGANISM: Ixodes scapularis

<400> SEQUENCE: 1

```
atggaatctt tcgtcgcaat gaaggtggtg tgcatactat ttttggttgg tgttgtcgct        60
gcgaatgaaa gcggcccaac taaagcagac gcatcaaccg ctgacaaaga tacgaagaaa       120
aacaatgtgc aacttcgatt ccctaattat atttctaacc accaaaagct tgccttgaaa       180
cttctgaaaa tttgcaagga tagcaaatct tctcacaatt cccttagttc ccgttcgtcc       240
gatgtgataa acgacaaata cgtggacttc aagaactgta catttctttg caaacatgga       300
aatgatgtta acgtgacatt gaatttgcca gaagacacgc cttgtggacc gaatggacag       360
acatgcgctg aaaagaataa atgcgttggc cacattcccg gatgttag                    408
```

<210> SEQ ID NO 2
<211> LENGTH: 135
<212> TYPE: PRT
<213> ORGANISM: Ixodes scapularis

<400> SEQUENCE: 2

```
Met Glu Ser Phe Val Ala Met Lys Val Val Cys Ile Leu Phe Leu Val
1               5                   10                  15

Gly Val Val Ala Ala Asn Glu Ser Gly Pro Thr Lys Ala Asp Ala Ser
            20                  25                  30

Thr Ala Asp Lys Asp Thr Lys Lys Asn Asn Val Gln Leu Arg Phe Pro
        35                  40                  45

Asn Tyr Ile Ser Asn His Gln Lys Leu Ala Leu Lys Leu Leu Lys Ile
    50                  55                  60

Cys Lys Asp Ser Lys Ser Ser His Asn Ser Leu Ser Ser Arg Ser Ser
65                  70                  75                  80

Asp Val Ile Asn Asp Lys Tyr Val Asp Phe Lys Asn Cys Thr Phe Leu
                85                  90                  95

Cys Lys His Gly Asn Asp Val Asn Val Thr Leu Asn Leu Pro Glu Asp
            100                 105                 110

Thr Pro Cys Gly Pro Asn Gly Gln Thr Cys Ala Glu Lys Asn Lys Cys
        115                 120                 125

Val Gly His Ile Pro Gly Cys
    130                 135
```

<210> SEQ ID NO 3
<211> LENGTH: 20
<212> TYPE: PRT
<213> ORGANISM: Ixodes scapularis

<400> SEQUENCE: 3

Asn Glu Ser Gly Pro Thr Lys Ala Asp Ala Ser Thr Ala Asp Lys Asp

```
                1               5                  10                 15
Thr Lys Lys Asn
            20

<210> SEQ ID NO 4
<211> LENGTH: 20
<212> TYPE: PRT
<213> ORGANISM: Ixodes scapularis

<400> SEQUENCE: 4

Ser Thr Ala Asp Lys Asp Thr Lys Lys Asn Asn Val Gln Leu Arg Phe
1               5                  10                 15

Pro Asn Tyr Ile
            20

<210> SEQ ID NO 5
<211> LENGTH: 20
<212> TYPE: PRT
<213> ORGANISM: Ixodes scapularis

<400> SEQUENCE: 5

Asn Val Gln Leu Arg Phe Pro Asn Tyr Ile Ser Asn His Gln Lys Leu
1               5                  10                 15

Ala Leu Lys Leu
            20

<210> SEQ ID NO 6
<211> LENGTH: 20
<212> TYPE: PRT
<213> ORGANISM: Ixodes scapularis

<400> SEQUENCE: 6

Ser Asn His Gln Lys Leu Ala Leu Lys Leu Leu Lys Ile Cys Lys Asp
1               5                  10                 15

Ser Lys Ser Ser
            20

<210> SEQ ID NO 7
<211> LENGTH: 20
<212> TYPE: PRT
<213> ORGANISM: Ixodes scapularis

<400> SEQUENCE: 7

Leu Lys Ile Cys Lys Asp Ser Lys Ser Ser His Asn Ser Leu Ser Ser
1               5                  10                 15

Arg Ser Ser Asp
            20

<210> SEQ ID NO 8
<211> LENGTH: 20
<212> TYPE: PRT
<213> ORGANISM: Ixodes scapularis

<400> SEQUENCE: 8

His Asn Ser Leu Ser Ser Arg Ser Ser Asp Val Ile Asn Asp Lys Tyr
1               5                  10                 15

Val Asp Phe Lys
            20

<210> SEQ ID NO 9
<211> LENGTH: 20
<212> TYPE: PRT
<213> ORGANISM: Ixodes scapularis
```

-continued

<400> SEQUENCE: 9

Val Ile Asn Asp Lys Tyr Val Asp Phe Lys Asn Cys Thr Phe Leu Cys
1               5                   10                  15

Lys His Gly Asn
            20

<210> SEQ ID NO 10
<211> LENGTH: 20
<212> TYPE: PRT
<213> ORGANISM: Ixodes scapularis

<400> SEQUENCE: 10

Asn Cys Thr Phe Leu Cys Lys His Gly Asn Asp Val Asn Val Thr Leu
1               5                   10                  15

Asn Leu Pro Glu
            20

<210> SEQ ID NO 11
<211> LENGTH: 20
<212> TYPE: PRT
<213> ORGANISM: Ixodes scapularis

<400> SEQUENCE: 11

Asp Val Asn Val Thr Leu Asn Leu Pro Glu Asp Thr Pro Cys Gly Pro
1               5                   10                  15

Asn Gly Gln Thr
            20

<210> SEQ ID NO 12
<211> LENGTH: 20
<212> TYPE: PRT
<213> ORGANISM: Ixodes scapularis

<400> SEQUENCE: 12

Asp Thr Pro Cys Gly Pro Asn Gly Gln Thr Cys Ala Glu Lys Asn Lys
1               5                   10                  15

Cys Val Gly His
            20

<210> SEQ ID NO 13
<211> LENGTH: 20
<212> TYPE: PRT
<213> ORGANISM: Ixodes scapularis

<400> SEQUENCE: 13

Gly Pro Asn Gly Gln Thr Cys Ala Glu Lys Asn Lys Cys Val Gly His
1               5                   10                  15

Ile Pro Gly Cys
            20

<210> SEQ ID NO 14
<211> LENGTH: 12
<212> TYPE: PRT
<213> ORGANISM: Ixodes scapularis

<400> SEQUENCE: 14

Glu Lys Asn Lys Cys Val Gly His Ile Pro Gly Cys
1               5                   10

<210> SEQ ID NO 15
<211> LENGTH: 13
<212> TYPE: PRT

-continued

```
<213> ORGANISM: Homo sapiens

<400> SEQUENCE: 15

His Ser Leu Gly Lys Trp Leu Gly His Pro Asp Lys Phe
1               5                   10

<210> SEQ ID NO 16
<211> LENGTH: 60
<212> TYPE: DNA
<213> ORGANISM: Ixodes scapularis

<400> SEQUENCE: 16
ggaccgaatg gacagacatg cgctgaaaag aataaatgcg ttggccacat tcccggatgt     60

<210> SEQ ID NO 17
<211> LENGTH: 36
<212> TYPE: DNA
<213> ORGANISM: Ixodes scapularis

<400> SEQUENCE: 17
gaaaagaata aatgcgttgg ccacattccc ggatgt                               36

<210> SEQ ID NO 18
<211> LENGTH: 18
<212> TYPE: DNA
<213> ORGANISM: Artificial Sequence
<220> FEATURE:
<223> OTHER INFORMATION: Artificially synthesized forward DNA primer for
      PCR amplification of Salp15 nucleotide sequence

<400> SEQUENCE: 18
gaaagcggcc caactaaa                                                   18

<210> SEQ ID NO 19
<211> LENGTH: 18
<212> TYPE: DNA
<213> ORGANISM: Artificial Sequence
<220> FEATURE:
<223> OTHER INFORMATION: Artificially synthesized reverse DNA primer for
      PCR amplification of Salp15 nucleotide sequence

<400> SEQUENCE: 19
ctaacatccg ggaatgtg                                                   18
```

MODULATION OF CD4⁺ T CELL RESPONSES BY A TICK SALIVA PROTEIN, SALP15 AND POLYPEPTIDES DERIVED THEREFROM

RELATED APPLICATIONS

This application claims the benefit of U.S. Provisional Patent Application Ser. No. 60/627,122, filed Nov. 12, 2004; the disclosure of which is incorporated herein by reference in its entirety.

GOVERNMENT INTEREST

This invention was made with U.S. Government support under Grant No. R01AI053064 awarded by National Institute of Allergy and Infectious Diseases, National Institutes of Health. The U.S. Government has certain rights in the presently disclosed subject matter.

TECHNICAL FIELD

The presently disclosed subject matter relates generally to isolated and purified polypeptides and nucleic acids and methods of using same. More particularly, the presently disclosed subject matter relates to isolated and purified Salp15 and biologically active fragments thereof having binding specificity for CD4 receptor polypeptides, and purified nucleic acid molecules encoding same. The presently disclosed subject matter further relates to methods of using the polypeptides to modulate activation of CD4⁺ T cells, including therapeutic methods for treating disorders related to T cell activation as well as inhibiting T cell infection by HIV. The presently disclosed subject matter further relates to screening methods for selecting compositions that can modulate activation of CD4⁺ T cells.

BACKGROUND

The immune system is highly complex and tightly regulated, with many alternative pathways capable of compensating for deficiencies in other parts of the system. There are however occasions when the immune response becomes a cause of disease or other undesirable conditions if activated. Immunoinflammatory disorders are thus characterized generally by the inappropriate activation of the body's immune defenses. Rather than targeting infectious invaders, the immune response targets and damages the body's own tissues or transplanted tissues. Such diseases or undesirable conditions are for example autoimmune diseases, graft rejection after transplantation, or allergy to innocuous antigens, psoriasis, chronic inflammatory diseases such as atherosclerosis, and inflammation in general.

The tissue targeted by the immune system varies with the disorder. For example, in multiple sclerosis, the immune response is directed against the neuronal tissue, while in Crohn's disease the digestive tract is targeted. Immunoinflammatory disorders affect millions of individuals and include conditions such as asthma, allergic intraocular inflammatory diseases, rheumatoid arthritis, atopic dermatitis, atopic eczema, type I diabetes, hemolytic anemia, inflammatory dermatoses, inflammatory bowel or gastrointestinal disorders (e.g., Crohn's disease and ulcerative colitis), multiple sclerosis, myasthenia gravis, pruritis/inflammation, psoriasis, cirrhosis, and systemic lupus erythematosus.

In these cases and others involving inappropriate or undesired immune response there is a clinical need for immunosuppression. The pathways leading to these undesired immune responses are numerous and in many cases are not fully elucidated. However, they often involve a common step, which is activation of lymphocytes.

Current treatment regimens for immunoinflammatory disorders typically rely on immunosuppressive agents that often are non-specific in their activity. The effectiveness of these agents can vary and their use is often accompanied by adverse side effects. Thus, improved therapeutic agents having specificity for inhibiting activation of T lymphocytes and methods for the treatment of immunoinflammatory disorders are needed.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In one embodiment, the presently disclosed subject matter provides an isolated and purified biologically active Salp15 polypeptide, comprising (a) a polypeptide encoded by a nucleic acid sequence as set forth in any of SEQ ID NOs: 16 and 17, (b) a polypeptide encoded by a nucleic acid having at least about 90% or greater sequence identity to a DNA sequence as set forth in any of SEQ ID NOs: 16 and 17, (c) a polypeptide having an amino acid sequence of any of SEQ ID NOs: 13 and 14, or a biologically functional equivalent thereof, (d) a polypeptide which is immunologically cross-reactive with antibodies which are immunologically reactive with a polypeptide having an amino acid sequence of any of SEQ ID NOs: 13 and 14, or (e) a polypeptide comprising a fragment of a polypeptide of (a), (b), (c), or (d). In some embodiments, the Salp15 polypeptide is modified to be in detectably labeled form. In some embodiments, a composition comprising the Salp15 polypeptide and a carrier is provided. In some embodiments, the carrier is a pharmaceutically acceptable carrier in humans.

In another embodiment of the presently disclosed subject matter, an isolated nucleic acid molecule is provided, comprising (a) a nucleic acid molecule encoding a polypeptide of any of SEQ ID NOs: 13 and 14, (b) a nucleic acid molecule having at least about 90% or greater sequence identity to a nucleic acid sequence as set forth in any of SEQ ID NOs: 16 and 17, or (c) a nucleic acid molecule having a sequence as set forth in any of SEQ ID NOs: 16 and 17. In some embodiments, a recombinant vector comprising the isolated nucleic acid molecule operatively linked to a promoter is provided, and in some embodiments a recombinant host cell comprising the nucleic acid molecule is further provided.

In yet another embodiment, the presently disclosed subject matter provides a method of modulating activation of a CD4⁺ T cell due to T cell receptor-mediated signaling. In some embodiments, the method comprises contacting the T cell with a Salp15 polypeptide disclosed herein, where activation of the T cell is modulated. In some embodiments, modulating activation of the T cell comprises inhibiting activation of the T cell, and in some embodiments inhibiting activation of the T cell results in decreased proliferation of the T cell. In some embodiments, contacting the T cell with the polypeptide comprises contacting a CD4 receptor expressed on the surface of the T cell with the polypeptide. Further, in some embodiments, contacting the CD4 receptor with the polypeptide comprises contacting at least a region of the extracellular outer two domains (D1-D2) of the CD4 receptor with the polypeptide. In some embodiments, the T cell is within a subject and the polypeptide is administered to the subject. Further, in some embodiments, the polypeptide is administered by systemic administration, parenteral administration, oral delivery, buccal delivery, subcutaneous administration, inhalation, intratracheal installation, surgical implantation, transdermal delivery, local injection, hyper-velocity injection/bombardment, or combinations thereof.

In a still further embodiment, a method of treating a subject suffering from or at risk of suffering from a condition characterized by a $CD4^+$ T cell response is provided. In some embodiments, the method comprises administering to the subject an effective amount of a Salp15 polypeptide disclosed herein. In some embodiments, the condition is an autoimmune disorder or a tissue or organ transplant rejection. Further, in some embodiments, the condition is an autoimmune disorder selected from the group consisting of lupus, rheumatoid arthritis, type 1 diabetes, multiple sclerosis, rheumatic fever, and Hashimoto's disease. In some embodiments, the polypeptide is administered by systemic administration, parenteral administration, oral delivery, buccal delivery, subcutaneous administration, inhalation, intratracheal installation, surgical implantation, transdermal delivery, local injection, hyper-velocity injection/bombardment, or combinations thereof.

In yet another embodiment of the presently disclosed subject matter, a method of treating multiple sclerosis in a subject is provided. In some embodiments, the method comprises administering to the subject an effective amount of a Salp15 polypeptide disclosed herein, or a biologically active fragment thereof, having immunosuppressive activity to the subject. In some embodiments, the Salp15 polypeptide is administered by systemic administration, parenteral administration, oral delivery, buccal delivery, subcutaneous administration, inhalation, intratracheal installation, surgical implantation, transdermal delivery, local injection, hyper-velocity injection/bombardment, or combinations thereof. In some embodiments, treating the multiple sclerosis comprises treating a relapsing episode of multiple sclerosis resulting from epitope spreading.

In yet another embodiment, the presently disclosed subject matter provides a method of inhibiting infection of a T cell by a human immunodeficiency virus (HIV). In some embodiments, the method comprises contacting a CD4 receptor expressed by the T cell with a Salp15 polypeptide disclosed herein, or a biologically active fragment thereof having binding specificity for the CD4 receptor, whereby contacting the Salp15 polypeptide with the CD4 receptor inhibits the HIV from infecting the T cell. In some embodiments, contacting the CD4 receptor with the Salp15 polypeptide comprises contacting the extracellular outer two domains (D1-D2) of the CD4 receptor with the Salp15 polypeptide. In some embodiments, the T cell is within a subject and the Salp15 polypeptide is administered to the subject. Further, in some embodiments, the polypeptide is administered by systemic administration, parenteral administration, oral delivery, buccal delivery, subcutaneous administration, inhalation, intratracheal installation, surgical implantation, transdermal delivery, local injection, hyper-velocity injection/bombardment, or combinations thereof.

In another embodiment, a method of screening a candidate substance for an ability to modulate activation of a $CD4^+$ T cell due to T cell receptor-mediated signaling is provided. In some embodiments, the method comprises establishing a test sample comprising a CD4 receptor polypeptide and a ligand for the CD4 receptor polypeptide, wherein the ligand is a Salp15 polypeptide disclosed herein; administering a candidate substance to the test sample; and measuring the effect of the candidate substance on binding of the CD4 receptor polypeptide and the ligand in the test sample to thereby determine the ability of the candidate substance to modulate activation of a $CD4^+$ T cell due to T cell receptor-mediated signaling. In some embodiments, the test sample further comprises an indicator, and the ability of the candidate substance to modulate activation of a $CD4^+$ T cell is determined by detecting a signal produced by the indicator upon an effect of the candidate substance on binding of the CD4 receptor polypeptide and the ligand; and identifying the candidate substance as a modulator of activation of a $CD4^+$ T cell based upon an amount of signal produced as compared to a control sample. In some embodiments, the candidate substance is a candidate polypeptide. In some embodiments, the ligand comprises an indicator. In some embodiments, the method further comprises the step of purifying and isolating a nucleic acid molecule encoding the candidate polypeptide. In some embodiments, the candidate polypeptide is an antibody or biologically functional equivalent fragment thereof and in other embodiments, the candidate substance is a small molecule. In some embodiments, the CD4 receptor polypeptide is immobilized to a solid support.

Therefore, it is an object of the presently disclosed subject matter to provide compositions comprising a Salp15 polypeptide which can modulate $CD4^+$ T cell responses.

An object of the presently disclosed subject matter having been stated hereinabove, and which is addressed in whole or in part by the presently disclosed subject matter, other objects will become evident as the description proceeds when taken in connection with the accompanying drawings and examples as best described hereinbelow.

BRIEF DESCRIPTION OF THE DRAWINGS

FIG. 1A shows PLCγ1 phosphorylation is decreased in anti-CD3/CD28 induced mouse $CD4^+$ T cells in the presence of Salp15, as analyzed by immunoblotting (upper panel) and confocal microscopy (lower panel) using anti-pPLCγ1$^{783}$.

FIG. 1B is a panel of representative immunofluorescence micrographs showing staining with anti-pTyr (pY) and anti-pLat$^{191}$ (pLAT) in $CD4^+$ T cells stimulated in the presence or absence of Salp15.

FIG. 1C shows a set of Western blots showing the decrease in tyrosine phosphorylation of Lck, Zap70 and Vav1 in $CD4^+$ T cells stimulated in the presence of Salp15.

FIGS. 2A-2C show Salp15 inhibits lipid raft redistribution in activated $CD4^+$ T cells.

FIG. 2A shows photomicrographs of CTB594 staining in $CD4^+$ T cells stimulated in the presence or absence of Salp15.

FIG. 2B shows photomicrographs of Salp15 treatment affects receptor capping in $CD4^+$ T cells but not in macrophages and B cells after activation using anti-CD3/CD28 cross-linked with anti-hamster $IgG_{488}$, anti-CD16/CD32 cross-linked with anti-rat $IgG_{594}$ and anti-IgM cross-linked with anti-rat $IgG_{594}$, respectively.

FIG. 2C shows photomicrographs of $CTB_{594}$ staining in $CD8^+$ T cells stimulated with anti-CD3/CD28 in the presence or absence of Salp15.

FIGS. 3A-3C show Salp15 pretreatment reduces actin polymerization during T cell activation.

FIG. 3A shows photomicrographs of Phalloidin$_{488}$ staining in CD4$^+$ T cells stimulated in the presence or absence of Salp15.

FIG. 3B shows that the levels of F-actin and G-actin isolated from lysates of CD4$^+$ T cells treated as indicated, were determined by immunoblotting with anti-actin. The lower panel shows the respective levels of total actin in the cell lysates.

FIG. 3C is a graph showing flow cytometric analysis of F-actin formation in unstimulated (shaded area) or stimulated CD4$^+$ T cells in the presence (gray) or absence (black) of Salp15 stained with phalloidin$_{488}$.

FIGS. 4A-4G show Salp15 binds directly to CD4.

FIG. 4A shows Jurkat cell lysate containing His-tagged Salp15 was immunoprecipitated using anti-His antibodies or IgG (control). The immunoprecipitate was subjected to Western blotting using anti-His and anti-CD4 antibodies.

FIG. 4B shows confocal photomicrographs demonstrating co-localization of anti-CD4 staining and Salp15$_{488}$ binding on naïve and stimulated CD4$^+$ T cells.

FIG. 4C shows graphs depicting flow cytometric analysis of CD4 expression (left panel) and Salp15$_{488}$ binding (right panel) in HeLa (black shaded) and HeLa-CD4 (unshaded) cells.

FIG. 4D shows co-localization of CD4 and Salp15$_{488}$ binding on HeLa-CD4 cells in photomicrographs.

FIG. 4E shows results of HeLa and HeLa-CD4 cell lysates containing Salp15 after immunoprecipitation using anti-His Ab. The immunoprecipitates and aliquots of both HeLa and HeLa-CD4 cell lysates (WCE) were subjected to immunoblotting using anti-CD4 and anti-His antibodies. Reciprocal immunoprecipitation from HeLa-CD4 cell lysate was done using anti-CD4 or IgG followed by immunoblotting with anti-CD4 or anti-His antibodies.

FIG. 4F shows photomicrographs demonstrating that unlabeled Salp15 but not lysozyme pretreatment of HeLa-CD4 cells blocks Salp15$_{488}$ binding.

FIG. 4G shows photomicrographs demonstrating that preincubation of HeLa-CD4 cells with polyclonal anti-CD4 abolishes Salp15$_{488}$ binding as compared to monoclonal OKT4. MT310 mAb also exhibited competition with Salp15$_{488}$ binding on HeLa-CD4 cells.

FIGS. 5A-5C show Salp15 binds to the outer-most extracellular domains of CD4.

FIG. 5A is a graph of Salp15 (0.4 µM) incubated with increasing amounts of immobilized sCD4 (extracellular domains D1D2, squares) or lysozyme (triangles) in a microtiter assay showing saturable binding. The results are expressed as mean±SE of three independent experiments.

FIG. 5B is a graph showing elution profiles of sCD4 (line 1), S15 (line 2), and sCD4-S15 (line 3) from Superdex-200 gel filtration columns (left panel). The Gaussian deconvolution of S15-sCD4 and sCD4 peaks is shown in the right panel graph.

FIG. 5C is an immunoblot showing both sCD4 and Salp15 were present in the same band when preincubated together. Purified sCD4 (10 µg), Salp15 (10 µg) and sCD4 (10 µg)+ Salp15 (10 µg) were subjected to native PAGE and immunoblotting with anti-CD4 and anti-His antibodies.

FIGS. 6A-6E shows the C-terminal peptide of Salp15 binds CD4 and inhibits T cell activation.

FIG. 6A is a graph showing binding of overlapping synthetic peptides of Salp15 (0.5 µg) to sCD4. The results are representative of four independent experiments.

FIG. 6B is a graph showing increasing concentrations of P11 (squares), but not P8 (triangles) show saturable binding to sCD4.

FIG. 6C is a graph showing competition of P11 (50 nmol) binding to sCD4 by increasing concentrations of Salp15.

FIG. 6D is a graph showing purified CD4$^+$ T cells were activated in vitro with plate bound anti-CD3 and soluble anti-CD28 in the absence or presence of Salp15 (50 µg/mL), P11, or P8. The supernatants were analyzed at 24 hr of activation for IL-2 levels by capture ELISA.

FIG. 6E shows photomicrographs of CTB$_{594}$ staining in CD4$^+$ T cells stimulated with anti-CD3/CD28 in the absence or presence of Salp15 (50 µg/mL), P11 (0.2 µg/mL), or P8 (0.2 µg/mL) for 20 min. The results are expressed as mean±SE of at least three independent experiments.

FIG. 7A is a Western blot showing the decrease in anti-CD3/CD28-induced tyrosine phosphorylation in CD4$^+$ T cells (upper panel) in the presence of Salp15. The middle and lower panels show immunoblotting with anti-actin and anti-Vav1 as loading controls.

FIG. 7B shows representative confocal micrographs of staining with anti-pTyr in Jurkat cells, either unstimulated or stimulated (αCD3/CD28) in the presence or absence of Salp15.

FIG. 7C shows representative confocal micrographs of staining with anti-CTB$_{594}$ in Jurkat cells, either unstimulated or stimulated (αCD3/CD28) in the presence or absence of Salp15.

FIG. 7D shows representative confocal micrographs demonstrating Jurkat cells stimulated with anti-CD3/CD28 in the presence of Salp15 exhibit highly reduced staining with phalloidin$_{488}$ compared to untreated controls.

FIG. 7E is an immunoblot showing the amount of F-actin isolated from lysates of Jurkat cells either unstimulated or stimulated in the presence or absence of Salp15 determined by immunoblotting with anti-actin. The lower panel shows the respective amount of total actin in the cell lysates.

FIG. 8A shows Jurkat cell lysate containing His-tagged Salp15 immunoprecipitated using anti-His, anti-CD3ε and anti-CD28. The immunoprecipitate was subjected to Western blotting using anti-CD4, anti-CD3ε, anti-CD28 and anti-TCRβ antibodies.

FIG. 8B shows confocal micrographs demonstrating Salp15$_{488}$ binding on the cell surface of CD4+, but not on CD8$^+$ cells.

FIG. 8C shows confocal micrographs of Salp15$_{488}$ binding on HeLa (upper panels) and HeLa-CD4 cells (lower panels).

FIG. 8D shows immunoprecipitation from HeLa-CD4 cell lysate containing either His tagged-Salp13-TR fusion protein or Salp15 using anti-His followed by immunoblotting with anti-CD4 or anti-His antibodies.

FIGS. 9A-9D shows Salp15 specifically inhibits CD4 dependent T cell activation.

FIG. 9A is a graph showing that the immunosuppressive activity of Salp15 was highly diminished in T cells isolated from CD4 deficient mice (filled bars) compared to control T cells (open bars). The results are expressed as mean±SE of three independent experiments.

FIG. 9B shows Salp15 does not inhibit ERK1/2 phosphorylation in CD4$^+$ T cells activated with anti-CD3/CD28.

FIG. 9C shows Salp15 does not affect STAT1 phosphorylation in CD4$^+$ T cells activated with 20 ng/mL of INFγ.

FIG. 9D is a graph showing Salp15 inhibits IL-2 production in a dose dependent manner in CD4$^+$ T cells isolated from DO11.10 transgenic mice activated with ovalbumin in the presence of APCs from a control mouse. The results are representative of three independent experiments.

FIGS. 10A-10D show the C-terminal peptide of Salp15 binds CD4.

FIG. 10A is a graph showing saturable binding of Salp15 (0.4 µM) with sCD4 D1-D4 (soluble extracellular domains D1-D4 of CD4). Salp15 was incubated with increasing amounts of immobilized sCD4 D1-D4 (squares) or lysozyme (circle) in a microtiter assay showing.

FIG. 10B is a graph showing competition of increasing concentrations of free P11 with immobilized P11 (50 nmol) for binding to sCD4.

FIG. 10C is a graph showing increasing concentrations of P11-2 (squares) but not PLP (triangles) show saturable binding to sCD4.

FIG. 10D is a graph showing Salp15 treatment with DTT did not affect its binding to sCD4-HRP in a microtiter assay. The results are expressed as mean±SE of at least three independent experiments.

BRIEF DESCRIPTION OF THE SEQUENCE LISTING

Figure 1A:
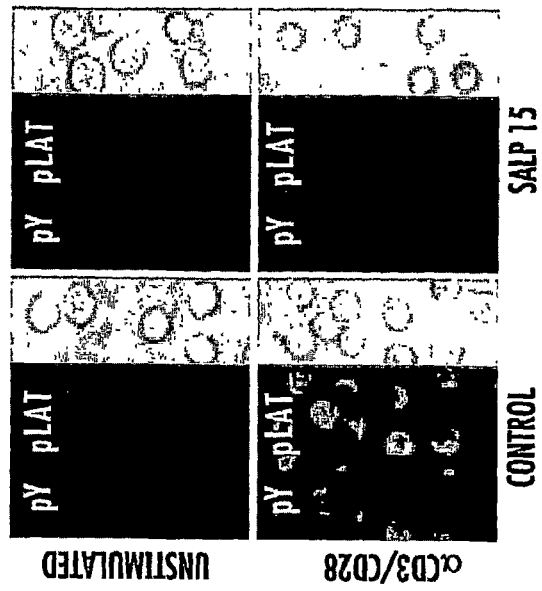
FIGS. 1A-1C show Salp15 inhibits protein tyrosine phosphorylation during T cell activation.

SEQ ID NO: 1 is a polynucleotide sequence encoding a Salp15 polypeptide isolated from *Ixodes scapularis*.

SEQ ID NO: 2 is a Salp15 polypeptide sequence isolated from *Ixodes scapularis*.

SEQ ID NO: 3 is a polypeptide fragment sequence (P1) comprising amino acids 1-20 of SEQ ID NO: 2.

SEQ ID NO: 4 is a polypeptide fragment sequence (P2) comprising amino acids 11-30 of SEQ ID NO: 2.

SEQ ID NO: 5 is a polypeptide fragment sequence (P3) comprising amino acids 21-40 of SEQ ID NO: 2.

SEQ ID NO: 6 is a polypeptide fragment sequence (P4) comprising amino acids 31-50 of SEQ ID NO: 2.

SEQ ID NO: 7 is a polypeptide fragment sequence (P5) comprising amino acids 41-60 of SEQ ID NO: 2.

SEQ ID NO: 8 is a polypeptide fragment sequence (P6) comprising amino acids 51-70 of SEQ ID NO: 2.

SEQ ID NO: 9 is a polypeptide fragment sequence (P7) comprising amino acids 61-80 of SEQ ID NO: 2.

SEQ ID NO: 10 is a polypeptide fragment sequence (P8) comprising amino acids 71-90 of SEQ ID NO: 2.

SEQ ID NO: 11 is a polypeptide fragment sequence (P9) comprising amino acids 81-100 of SEQ ID NO: 2.

SEQ ID NO: 12 is a polypeptide fragment sequence (P10) comprising amino acids 91-110 of SEQ ID NO: 2.

SEQ ID NO: 13 is a polypeptide fragment sequence (P11) comprising amino acids 95-114 of SEQ ID NO: 2.

SEQ ID NO: 14 is a polypeptide fragment sequence (P11-2) comprising amino acids 103-114 of SEQ ID NO: 2.

SEQ ID NO: 15 is a polypeptide fragment sequence comprising amino acids 139-151 of proteolipid protein 1 (PLP).

SEQ ID NO: 16 is a polynucleotide sequence encoding the polypeptide of SEQ ID NO: 13.

SEQ ID NO: 17 is a polynucleotide sequence encoding the polypeptide of SEQ ID NO: 14.

SEQ ID NO: 18 is a forward oligonucleotide primer used to amplify a Salp15 polypeptide by PCR.

SEQ ID NO: 19 is a reverse oligonucleotide primer used to amplify a Salp15 polypeptide by PCR.

DETAILED DESCRIPTION

The presently disclosed subject matter provides compositions capable of specifically binding to T-lymphocyte and of modulating Class II MHC-mediated T-lymphocyte activation via the T cell receptor activation pathway of $CD4^+$ T cells and consequently capable of acting as immunomodulators and anti-inflammatory agents. The compositions have binding specificity for the T cell CD4 co-receptor and can cause conformational changes to the CD4 co-receptor that can inhibit T cell activation. The compositions can further act as inhibitors of human immunodeficiency virus (HIV) infection of $CD4^+$ T cells, as they can bind competitively with the CD4 co-receptor and thereby prevent binding of HIV to the T cell via HIV gp120 polypeptide interaction with T cell CD4. The compositions disclosed herein are further useful in methods of screening for additional substances having similar properties as the presently disclosed compositions.

In some embodiments, the presently disclosed compositions, which are capable of specifically binding to and modulating $CD4^+$ T cells, comprise Salp15, or biologically active fragments thereof. Salp15, disclosed herein for the first time, binds specifically to CD4 on $CD4^+$ T cells and acts at the earliest steps of TCR signaling. This can result in diminished tyrosine phosphorylation of effector proteins, defective actin polymerization, and/or a reduction in lipid raft reorganization. It has also been discovered, and disclosed herein for the first time, that the immunosuppressive effect of Salp15 can be exerted through a direct and specific association between its C-terminal amino acid region and the outer two extracellular domains of CD4 (D1-D2). A direct association between the outer two extracellular domains of CD4 and the C-terminal amino acid residues of Salp15 is sufficient to exert the immunosuppressive effect of Salp15 on $CD4^+$ T cells. Thus, Salp15 and biologically active fragments thereof, have utility in treating or preventing with specificity conditions characterized by $CD4^+$ T cell responses, including autoimmune disorders and allogeneic transplant tolerance and as inhibitors of HIV infection of $CD4^+$ T cells, as disclosed in detail herein.

I. General Considerations

Engagement of the T cell receptor complex (TCR) by Class II MHC protein and associated proteins initiates a complex cascade of biochemical events that culminate in proliferation and the initiation of effector functions by T cells. The most proximal and earliest events include the activation of protein kinases of the Src, Syk, and Tec families (Bolen and Brugge, 1997; Qian and Weiss, 1997), resulting in tyrosine phosphorylation of multiple membrane-bound and cytosolic proteins (Koretzky et al., 2003). The recruitment of these effector proteins to the site of TCR-Class II MHC interaction, also referred to as the "immunological synapse", leads to signal amplification resulting in calcium mobilization from intracellular stores and interleukin (IL)-2 production (Myung et al., 2000; Zhang and Samelson, 2000), which in turn stimulates activation, proliferation, and differentiation of T cells.

*Ixodes scapularis* salivary protein 15 (Salp15) was recently identified as the first antigen responsible for the immuno-modulatory action of tick saliva on acquired immune responses (Anguita et al., 2002, herein incorporated by reference in its entirety). Salp15 causes the repression of calcium fluxes triggered by TCR ligation, and therefore NFAT and NF-κB-induced IL-2 transcription. Thus, inhibition of T cell activation mediated by Salp15 results from the repression of calcium fluxes triggered by TCR ligation with a subsequent reduction in IL-2 production.

*I. scapularis* ticks act as the vector for several pathogens including the causative agents of Lyme disease and human granulocytic ehrlichiosis (Burgdorfer et al., 1982; Chen et al., 1994). In order to thrive in nature, ticks are able to modulate the host immune response. Tick salivary proteins enter the host during feeding and exert pleiotropic immunosuppressive effects (Anguita et al., 2002; Ferreira and Silva, 1998; Kopecky and Kuthejlova, 1998; Ribeiro et al., 1995; Schoeler et al., 1999; Urioste et al., 1994; Wikel and Bergman, 1997). Immunosuppression of the host by tick saliva could also contribute to the efficient transmission of tick-borne pathogens (Wikel, 1999 and Ramamoorthi et al., 2005, herein incorporated by reference).

Salp15 is a candidate for use in immunosuppressive therapies. A clear understanding of the mechanism by which Salp15 causes immunosuppression, however, is a prerequisite for continuing further studies regarding its potential use. Prior to the discovery of the subject matter disclosed herein, a full understanding of Salp15 mechanism of T cell inhibition was unknown.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage can encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "antibody" or "antibody molecule" refers collectively to a population of immunoglobulin molecules and/or immunologically active portions of immunoglobulin molecules, i.e., molecules that contain a paratope. A paratope is the portion or portions of antibodies that is or are responsible for that antibody binding to an antigenic determinant, or epitope.

Representative antibodies for use in the present subject matter are intact immunoglobulin molecules, substantially intact immunoglobulin molecules, single chain immunoglobulins or antibodies, those portions of an immunoglobulin molecule that contain the paratope, including antibody fragments. A monovalent antibody can optionally be used.

The terms "associated with", "operably linked", and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The terms "CD4", "CD4 receptor", and "CD4 coreceptor" are used interchangeably herein and refer to a transmembrane glycoprotein expressed on certain immune system cells, including helper T cells (CD4$^+$ T cells). CD4 expressed on helper T cells acts as a coreceptor along with the T cell receptor complex in the TCR-mediated activation pathway of T cells, which occurs when a TCR (along with accessory molecules, including CD4) recognizes and binds to, in the case of helper T cells, an MHC Class II molecule presenting a particular antigen recognized by the TCR. After initial binding of TCR with the Class II MHC molecule-antigen complex, CD4 binds the Class II MHC molecule at a site separate from the TCR binding site. CD4 primarily functions as part of the T cell activation signaling cascade, but might also play a role in adhesion to stabilize the TCR-MHC complex. CD4 is expressed as a monomer with four extracellular Ig-like domains, numbered D1 through D4 beginning from the N-terminus (D1-D4) (Capon et al., 1989; Fleury et al., 1991), a hydrophobic transmembrane domain, and a highly basic cytoplasmic tail of 38 amino acids. CD4 binds Class II MHC through its two N-terminal extracellular domains (D1-D2).

As used herein, "CD4" refers not only to the full-length protein, but biologically active fragments as well. In particular, the extracellular four domains of CD4 (sCD4) or even D1-D2 alone can function to bind Class II MHC, and so these fragments are biologically active in the sense of binding MHC and may be referred to herein simply as CD4, for example. Further, Salp15 can specifically bind the D1-D2 fragment of CD4 and so is a particularly relevant biologically active fragment for the purposes of the presently disclosed subject matter.

The terms "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide.

The term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction.

The term "fragment" refers to a sequence that comprises a subset of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc.

A fragment can also be a "functional fragment", in which the fragment retains a specific biological function of the nucleic acid sequence or amino acid sequence of interest. For example, a functional fragment of a Salp15 polypeptide can include a region having binding specificity for a CD4 co-receptor and/or capable of modulating activation of a CD4$^+$ T cell.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

A "homologous" nucleic acid (or amino acid) sequence is a nucleic acid (or amino acid) sequence naturally associated with a host cell into which it is introduced.

The term "inhibitor" refers to a chemical substance that inactivates or decreases the biological activity of a target entity such as a complement component.

The term "isolated", when used in the context of an isolated DNA molecule or an isolated polypeptide, is a DNA molecule or polypeptide that, by the hand of man, exists apart from its native environment and is therefore not a product of nature. An isolated DNA molecule or polypeptide can exist in a purified form or can exist in a non-native environment such as, for example, in a transgenic host cell.

The term "MHC polypeptide" and "MHC molecule" as used herein refers to a polypeptide expressed on the membrane surface of an antigen presenting cell (APC), which serves as a peptide display (antigen presentation) molecule for recognition by T cells, and more specifically, by the TCRs in complex with other signaling molecules of the T cells. MHC polypeptides can generally be categorized into two structurally distinct classes. Class I MHC molecules are present on most nucleated cells, bind and present peptides derived from cytosolic proteins, and are recognized by TCRs on $CD8^+$ T cells. Class II MHC polypeptides are restricted primarily to "professional" antigen presenting cells (such as macrophages and dendritic cells), bind and present peptides derived from endocytosed proteins, and are recognized by TCRs on $CD4^+$ T cells.

As used herein, the term "modulate" means an increase, decrease, or other alteration of any, or all, chemical and biological activities or properties of a target entity, such as a wild-type or mutant polypeptide, including but not limited to a Salp15 polypeptide. The term "modulation" as used herein refers to both upregulation (i.e., activation or stimulation) and downregulation (i.e. inhibition or suppression) of a response, such as for example, modulation of a T cell activation response, including modulation of activation and proliferation of the T cell resulting from the modulated response.

As used herein, the term "mutation" carries its traditional connotation and means a change, inherited, naturally occurring or introduced, in a nucleic acid or polypeptide sequence, and is used in its sense as generally known to those of skill in the art.

As used herein, the terms "T lymphocyte" or "T cell" are used interchangeably and refer to cells of the immune system that mediate cell-mediated immune responses as part of the adaptive immune system. T cells are named for their tissue of origin, the thymus. T cells, however, circulate in the blood, populate lymphoid tissues and some subclasses are recruited to peripheral sites of antigen exposure when activated to facilitate an immune response to an antigen. T cells express T cell receptors (TCRs) that recognize antigen (e.g., peptide fragments) when bound to MHC molecules. T cells can be further divided into subclasses of $CD4^+$ T cells (referred to as helper T cells) and $CD8^+$ T cells (referred to as cytotoxic T lymphocytes), which express as membrane bound coreceptors of TCR CD4 or CD8, respectively.

As used herein, the term "T cell receptor" or "TCR" refers to a clonally distributed polypeptide expressed on the membrane surface of $CD4^+$ and $CD8^+$ T lymphocytes. TCRs are antigen receptors that function as a component of the immune system for recognition of peptides bound to MHC molecules on the surface of antigen presenting cells. A TCR comprises a diversity or variable region within its polypeptide sequence that contributes to the determination of the particular antigen and MHC molecule to which the TCR has binding specificity. In turn, the specificity of a T cell for a unique antigen-MHC complex resides in the particular TCR expressed by the T cell.

The most common structural form of a TCR found in vivo is as a heterodimer of two disulfide-linked transmembrane polypeptide chains, designated $\alpha$ and $\beta$, each chain comprising one N-terminal diversity region, one immunoglobulin-like constant domain, a hydrophobic transmembrane region and a short cytoplasmic region. A less common type of TCR comprising $\gamma$ and $\delta$ chains is found in a small subset of cells and is included by the term TCR as used herein.

Although the term TCR, as used herein, includes the entire heterodimer structure, the term is not intended to be limited to this single definition. TCR, as used herein, further includes each $\alpha$ and $\beta$ chain individually, as well as biologically active fragments thereof, including fragments soluble in aqueous solutions, of either chain alone or both chains joined. Biologically active fragments maintain the ability to at least bind with specificity to a specific antigen, and therefore will include at least a portion of the diversity region imparting antigen-MHC complex specificity. Biologically active fragments of TCRs disclosed herein can further include other functionalities of full-length TCRs, such as forming a TCR complex with other proteins, such as signaling proteins, on the membrane surface of a T cell and activating the T cell. TCR as used herein also includes, and is used interchangeably with the term "TCR complex", which comprises the TCR along with noncovalently associated proteins that play a role in transduction of the signal arising from TCR binding to a particular antigen-MHC complex, such as for example CD3 and ξ proteins.

TCRs normally play a role in recognition of foreign antigens, followed by T cell activation, proliferation (i.e., clonal expansion of the activated T cell), and differentiation (i.e., maturation to either an effector or memory T cell, each having distinct roles in the immune system) with a resultant activation and targeting of the immune system against the foreign antigen. However, TCRs can sometimes have specificity for and activate when contacted with MHC presented self-antigens, also referred to herein as autoantigens. Activation of T cells as a result of binding by TCRs to autoantigen-MHC complexes can play a role in certain autoimmune diseases, including for example multiple sclerosis. T cell activation via TCR-mediated signaling also plays a role in tissue and organ transplant rejection.

The term "transformation" refers to a process for introducing heterologous DNA into a cell. Transformed cells are understood to encompass not only the end product of a transformation process, but also transgenic progeny thereof.

The terms "transformed", "transgenic", and "recombinant" refer to a cell of a host organism such as a mammal into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof. A "non-transformed," "non-transgenic", or "non-recombinant" host refers to a wild type organism, e.g., a mammal or a cell therefrom, which does not contain the heterologous nucleic acid molecule.

III. Polypeptides and Nucleic Acids

The presently disclosed subject matter discloses isolated and purified biologically active Salp15 polypeptides and nucleic acid molecules encoding same. As used in the following detailed description and in the claims, the term "Salp15" includes tick (e.g. *Ixodes scapularis*) salivary protein 15 polypeptides, and biologically functional equivalents thereof and nucleic acids encoding same. The term "Salp15" includes homologs from non-tick species. Preferably, Salp15 nucleic acids and polypeptides are isolated from eukaryotic sources.

The terms "Salp15 gene product", "Salp15 protein", and "Salp15 polypeptide" refer to peptides having amino acid sequences which are substantially identical to native amino acid sequences from the organism of interest and which are biologically active in that they comprise all or a part of the amino acid sequence of a Salp15 protein, or cross-react with antibodies raised against a Salp15 polypeptide, or retain all or some of the biological activity of the native amino acid sequence or protein. For example, in one embodiment a Salp15 protein is a polypeptide isolated originally as a secreted salivary protein from *Ixodes scapularis* and set forth herein as SEQ ID NO: 2 and encoded by a polynucleotide, for example, as set forth in SEQ ID NO:1. See also Anguita et al., 2002.

In some embodiments, the Salp15 polypeptide is modified to be in a detectably labeled form. A labeled form of the Salp15 polypeptide has several utilities, as would be appreciated by one of skill in the art. For example, a labeled Salp15 polypeptide could be used to identify the presence of a molecule to which Salp15 binds with specificity in a sample, e.g., a CD4 receptor polypeptide. The molecule to which Salp15 binds could be soluble or bound. For example, the molecule could be expressed by a cell, or certain types of cells, and a labeled Salp15 polypeptide could be utilized to determine whether a population of cells, or individual members thereof, express the molecule. Methods of using a labeled Salp15 polypeptide in this manner are known to those of skill in the art. For example, a population of cells could be quickly screened for cells expressing a molecule to which Salp15 binds with specificity (e.g., CD4) using a labeled Salp15 polypeptide in conjunction with a fluorescence activated cell sorter.

The terms "Salp15 gene product", "Salp15 protein", and "Salp15 polypeptide" also include biologically functional equivalents and analogs of Salp15. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct Salp15 analogs. There is no need for a "Salp15 gene product", "Salp15 protein", and "Salp15 polypeptide" to comprise all or substantially all of the amino acid sequence of a native Salp15 gene product. Shorter or longer sequences are anticipated to be of use in the presently disclosed subject matter; shorter sequences are herein referred to as "fragments" or "segments". Thus, the terms "Salp15 gene product", "Salp15 protein", and "Salp15 polypeptide" also include fragment, fusion, chemically modified, or recombinant Salp15 polypeptides and proteins comprising sequences of the presently disclosed subject matter. Methods of preparing such proteins are known in the art.

The terms "Salp15 gene", "Salp15 gene sequence", and "Salp15 gene fragment" refer to any DNA sequence that is substantially identical to a polynucleotide sequence encoding a Salp15 gene product, protein or polypeptide as defined above, and can also comprise any combination of associated control sequences. The terms also refer to RNA, or antisense sequences, complementary to such DNA sequences. As used herein, the term "DNA segment" or "DNA fragment" refers to a DNA molecule that has been isolated free of total genomic DNA of a particular species. Furthermore, a DNA segment encoding a Salp15 polypeptide refers to a DNA segment that contains Salp15 coding sequences, yet is isolated away from, or purified free from, total genomic DNA of a source species, such as *I. scapularis*. Included within the term "DNA segment" are DNA segments and smaller fragments of such segments, and also recombinant vectors, including, for example, plasmids, cosmids, phages, viruses, and the like.

Exemplary polypeptide fragments of Salp15 encompassed by the presently disclosed subject matter are set forth in Table 1 (SEQ ID NOs: 3-14; SEQ ID NO: 15 is a non-SALP15 polypeptide negative control). As disclosed herein in the Examples, Salp15 polypeptide fragments P11 (SEQ ID NO: 13) and P11-2 (SEQ ID NO: 14) are derived from the C-terminus of Salp15 and have been experimentally determined to exhibit the highest activity of the tested polypeptide fragments of Salp15 for modulating naïve $CD4^+$ T cell activation.

SEQ ID NOs: 16 and 17 set forth the polynucleotide coding sequences for P11 and P11-2, respectively.

TABLE 1

Overlapping synthetic peptides of Salp15

| Peptide | Position | Sequence | SEQ. ID NO: |
|---|---|---|---|
| P1 | 1-20 | NESGPTKADASTADKDTKKN | 3 |
| P2 | 11-30 | STADKDTKKNNVQLRFPNYI | 4 |
| P3 | 21-40 | NVQLRFPNYISNHQKLALKL | 5 |
| P4 | 31-50 | SNHQKLALKLLKICKDSKSS | 6 |
| P5 | 41-60 | LKICKDSKSSHNSLSSRSSD | 7 |
| P6 | 51-70 | HNSLSSRSSDVINDKYVDFK | 8 |
| P7 | 61-80 | VINDKYVDFKNCTFLCKHGN | 9 |
| P8 | 71-90 | NCTFLCKHGNDVNVTLNLPE | 10 |
| P9 | 81-100 | DVNVTLNLPEDTPCGPNGQT | 11 |
| P10 | 91-110 | DTPCGPNGQTCAEKNKCVGH | 12 |
| P11k | 95-114 | GPNGQTCAEKNKCVGHIPGC | 13 |
| P11-2* | 103-114 | EKNKCVGHIPGC | 14 |
| PLP | 139-151 | HSLGKWLGHPDKF | 15 |

*Polynucleotide coding sequences for:
P11-gga ccg aat gga cag aca tgc gct gaa aag aat aaa tgc gtt ggc cac att ccc gga tgt (SEQ ID NO: 16); and P11-2-gaa aag aat aaa tgc gtt ggc cac att ccc gga tgt (SEQ ID NO: 17).

The term "substantially identical", when used to define either a Salp15 gene product or amino acid sequence, or a Salp15 gene or nucleic acid sequence, means that a particular sequence varies from the sequence of a natural Salp15 or fragment thereof by one or more deletions, substitutions, or additions, the net effect of which is to retain at least some of the biological activity of the natural gene, gene product, or sequence. Such sequences include "mutant" sequences, or sequences in which the biological activity is altered to some degree but retains at least some of the original biological activity.

Alternatively, DNA analog sequences are "substantially identical" to specific DNA sequences disclosed herein if: (a) the DNA analog sequence is derived from coding regions of the natural Salp15 gene; or (b) the DNA analog sequence is capable of hybridization of DNA sequences of (a) under stringent conditions and which encode biologically active Salp15 gene product; or (c) the DNA sequences are degenerate as a result of alternative genetic code to the DNA analog sequences defined in (a) and/or (b). Substantially identical analog proteins will be greater than about 80% identical to the corresponding sequence of the native protein or biologically active fragment thereof. Sequences having lesser degrees of identity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids or modifications to amino acids (e.g., chemical modifications) to create biologically functional equivalents.

Sequence identity or percent similarity of a DNA or peptide sequence can be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See Schwartz et al., 1979; Gribskov et al., 1986.

In certain embodiments, the presently disclosed subject matter concerns the use of Salp15 genes and gene products that include within their respective sequences a sequence that is essentially that of a Salp15 gene, or the corresponding protein, or fragments thereof. The term "a sequence essentially as that of a Salp15 gene", means that the sequence is substantially identical or substantially similar to a portion of a Salp15 gene or gene products and contains a minority of bases or amino acids (whether DNA or protein) which are not identical to those of a Salp15 protein or a Salp15 gene, or which are not a biologically functional equivalent. The term "biologically functional equivalent" is well understood in the art and is further defined in detail herein. Nucleotide sequences are "essentially the same" where they have between about 80% and about 85% or more preferably, between about 86% and about 90%, or more preferably greater than 90%, or more preferably about 91%, 92%, 93%, 94%, 95%, 96%, 97%, 98%, or 99%; of nucleic acid residues which are identical to the nucleotide sequence of a Salp15 gene. Similarly, peptide sequences which have about 80%, or 90% or greater, or about 91%, 92%, 93%, 94%, 95%, 96%, 97%, 98%, or 99% or greater amino acids which are identical or functionally equivalent or biologically functionally equivalent to the amino acids of a Salp15 polypeptide will be sequences which are "essentially the same".

Salp15 gene products and Salp15 encoding nucleic acid sequences, which have functionally equivalent codons, are also covered by the subject matter disclosed herein. The term "functionally equivalent codon" is used herein to refer to codons that encode the same amino acid, such as the ACG and AGU codons for serine. Thus, when referring to the sequence examples presented in SEQ ID NOs: 1, 16 or 17, for example, applicants contemplate substitution of functionally equivalent codons of Table 2 into the sequence examples of SEQ ID NOs: 1, 16 or 17. Thus, applicants are in possession of amino acid and nucleic acid sequences which include such substitutions but which are not set forth herein in their entirety for convenience.

TABLE 2

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |

TABLE 2-continued

Functionally Equivalent Codons

| Amino Acids | | | Codons |
|---|---|---|---|
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present subject matter also encompasses the use of nucleotide segments that are complementary to the sequences of the presently disclosed subject matter, in one embodiment, segments that are fully complementary, i.e. complementary for their entire length. Nucleic acid sequences that are "complementary" are those, which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

One technique in the art for assessing complementary sequences and/or isolating complementary nucleotide sequences is hybridization. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See e.g., Wethmur & Davidson, 1968. Determining appropriate hybridization conditions to identify and/or isolate sequences containing high levels of homology is well known in the art. See e.g., Sambrook et al., 2001.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C. Another example of "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68° C. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate).

Nucleic acids that are substantially identical to the provided Salp15 sequences, e.g., allelic variants, genetically altered versions of the gene, etc., bind to the provided Salp15 sequences under stringent hybridization conditions. By using probes, particularly labeled probes of DNA sequences, one can isolate homologous or related genes. The source of homologous genes can be any species, e.g., arthropod species, particularly tick species (Order acari), and also including primate species, particularly human; rodents, such as rats and mice, canines, felines, bovines, ovines, equines, yeast, nematodes, etc.

Between arthropod species, e.g., ticks, mites, insects, and spiders, homologs have substantial sequence similarity, i.e. at least 80% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides long, more usually at least about 30 nucleotides long, and can extend to the complete sequence that is being compared. Algorithms for sequence analysis are known in the art, such as BLAST, described in Altschul et al., 1990. The sequences provided herein are essential for recognizing Salp15 related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position—these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

The Salp15 polypeptides disclosed herein are thus homologous polypeptides, but when percentages are referred to herein, it is meant to refer to percent identity. The percent identities referenced herein can be generated, for example, by alignments with the program GENEWORKS™ (Oxford Molecular, Inc. of Campbell, Calif., United States of America) and/or the BLAST program at the NCBI website.

Another commonly used alignment program is entitled CLUSTAL W and is described in Thompson et al., 1994, among other places.

Probe sequences can also hybridize specifically to duplex DNA under certain conditions to form triplex or other higher order DNA complexes. The preparation of such probes and suitable hybridization conditions are disclosed herein and are known in the art.

The term "gene" is used for simplicity to refer to a functional protein, polypeptide or peptide encoding unit. As will be understood by those in the art, this functional term includes both genomic sequences and cDNA sequences.

Preferred embodiments of genomic and cDNA sequences are disclosed herein. In particular embodiments, the presently disclosed subject matter concerns isolated DNA segments and recombinant vectors incorporating DNA sequences, which encode a Salp15 polypeptide or biologically active fragment thereof that includes within its amino acid sequence an amino acid sequence as described herein. In other particular embodiments, the presently disclosed subject matter concerns recombinant vectors incorporating DNA segments, which encode a protein comprising the amino acid sequence of an *I. scapularis* Salp15 protein (for example, but not limited to SEQ ID NO: 2) or biologically functional equivalents thereof (for example, but not limited to SEQ ID NOs: 13 and 14).

III.A. Biologically Functional Equivalents

As mentioned above, modifications and changes can be made in the structure of the Salp15 proteins and peptide fragments described herein and still constitute a molecule having like or otherwise desirable characteristics. For example, certain amino acids can be substituted for other amino acids or chemically modified (e.g., to increase stability of the peptide) in a protein structure without appreciable loss of interactive capacity with, for example, proteins expressed on the surface of T cells, including in particular the CD4 co-receptor expressed by helper T cells ($T_H$) cells, which can modulate activation of these T cells. Since it is the interactive capacity and nature of a protein that defines that protein's biological functional activity, certain amino acid sequence modifications or substitutions can be made in a protein sequence (or the nucleic acid sequence encoding it) to obtain a protein with the same, enhanced, or antagonistic properties. Such properties can be achieved by interaction with the normal targets of the native protein, but this need not be the case. It is thus provided in accordance with the present subject matter that various modifications or changes can be made in the sequence of the Salp15 proteins and peptides or underlying nucleic acid sequence without appreciable loss of their biological utility or activity.

Biologically functional equivalent peptides, as used herein, are peptides in which certain, but not most or all, of the amino acids can be substituted and/or chemical modifications, substitutions or additions are made to one or more amino acids. Thus, for example, when referring to the sequence examples presented in SEQ ID NOs: 2, 13, and 14 applicants contemplate substitution of codons that encode biologically equivalent amino acids as described herein into the sequence examples of SEQ ID NOs: 2, 13, and 14. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test Salp15 mutants in order to examine Salp15 activity at the molecular level.

Amino acid substitutions, such as those which might be employed in modifying the Salp15 proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Those of skill in the art will appreciate other biologically functionally equivalent changes.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those, which are within ±1 of the original value, are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those, which are within ±1 of the original value, are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that the presently disclosed subject matter is not limited to the particular nucleic acid and amino acid sequences of SEQ ID NOs: 1, 2, 13, 14, 16, and 17. Recombinant vectors and isolated DNA segments can therefore variously include the Salp15 polypeptide-encoding region itself, include coding regions bearing selected alterations or modifications in the basic coding region, or include larger polypeptides which nevertheless comprise Salp15-encoding regions or can encode biologically functional equivalent proteins or peptides which have variant amino acid sequences, or can encode biologically functional equivalent fragments of the entire Salp15, including in particular fragments of the C-terminus of Salp15 having binding specificity for T cell-expressed proteins, including CD4 co-receptor. Biological activity of a Salp15 polypeptide can include binding specificity for CD4 co-receptor and ability to modulate activation of T cells. Determining biological activity as described herein is within the ordinary skill of one skilled in the art, upon review of the present disclosure. Exemplary procedures for determining biological activity of Salp15 polypeptides are disclosed herein in the Examples.

In particular embodiments, the presently disclosed subject matter concerns isolated DNA sequences and recombinant DNA vectors incorporating DNA sequences that encode a protein comprising the amino acid sequence of the Salp15 polypeptide from *I. scapularis*. In certain other embodiments, the present subject matter concerns isolated DNA segments and recombinant vectors that comprise a nucleic acid sequence essentially as set forth in SEQ ID NOs: 16 or 17.

The nucleic acid segments of the present subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of SEQ ID NOs: 1, 16, or 17 such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also contemplated to be useful.

The DNA segments of the present subject matter encompass biologically functionally equivalent Salp15 proteins and peptides. Such sequences can arise as a consequence of codon redundancy and functional equivalency that are known to occur naturally within nucleic acid sequences and the proteins thus encoded. Alternatively, functionally equivalent proteins or peptides can be created via the application of chemical synthesis or recombinant DNA technology, in which changes in the protein structure can be engineered, based on considerations of the properties of the amino acids being exchanged. Changes can be introduced through the application of site-directed mutagenesis techniques, e.g., to introduce improvements to the antigenicity of the protein or to test Salp15 mutants in order to examine activity in the modulation of, for example, binding specificity for CD4 co-receptor polypeptides, modulation of T cell activity, inhibition of HIV infection, or other activity at the molecular level. Site-directed mutagenesis techniques are known to those of skill in the art and are disclosed herein.

The presently disclosed subject matter further encompasses fusion proteins and peptides wherein the Salp15 coding region is aligned within the same expression unit with other proteins or peptides having desired functions, such as for purification, labeling, or immunodetection purposes.

Recombinant vectors form further aspects of the present disclosure. Particularly useful vectors are those in which the coding portion of the DNA segment is positioned under the control of a promoter. The promoter can be that naturally associated with the Salp15 gene, as can be obtained by isolating the 5' non-coding sequences located upstream of the coding segment or exon, for example, using recombinant cloning and/or polymerase chain reaction (PCR) technology and/or other methods known in the art, in conjunction with the compositions disclosed herein.

In other embodiments, it is provided that certain advantages will be gained by positioning the coding DNA segment under the control of, i.e. operatively linked to, a recombinant, or heterologous, promoter. As used herein, a recombinant or heterologous promoter is a promoter that is not normally associated with a Salp15 gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al., 2001). The promoters employed can be constitutive or inducible and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccinia virus promoter and the baculovirus promoter.

In an alternative embodiment, the presently disclosed subject matter provides an expression vector comprising a polynucleotide that encodes a biologically active Salp15 polypeptide in accordance with the present disclosure. In one example, an expression vector of the present subject matter comprises a polynucleotide that encodes a Salp15 gene product. In another example, an expression vector of the present subject matter comprises a polynucleotide that encodes a polypeptide comprising an amino acid residue sequence of SEQ ID NOs: 13 or 14. In yet another example, an expression vector of the presently disclosed subject matter comprises a polynucleotide comprising the nucleotide sequence of SEQ ID NOs: 16 or 17. Optionally, an expression vector of the presently disclosed subject matter comprises a polynucleotide operatively linked to an enhancer-promoter. For example, an expression vector can comprise a polynucleotide operatively linked to a prokaryotic promoter. Alternatively, an expression vector of the presently disclosed subject matter comprises a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide.

In yet another embodiment, disclosed herein is a recombinant host cell transfected with a polynucleotide that encodes a biologically active Salp15 polypeptide in accordance with the present subject matter. SEQ ID NOs: 16 and 17 and 13 and 14 set forth representative nucleotide and amino acid sequences of Salp15, respectively, from ticks. Also provided are homologous or biologically functionally equivalent polynucleotides and Salp15 polypeptides found in other animals, including for example other arthropod homologs. Optionally, a recombinant host cell of the present subject matter is transfected with the polynucleotide that encodes a Salp15 polypeptide. As another option, a recombinant host cell is transfected with the polynucleotide sequence encoding or set forth in SEQ ID NOs: 16 or 17. A recombinant host cell is a bacterial cell, a mammalian cell or an insect cell. In some embodiments, the host cell is an attenuated bacterium, such as for example, attenuated *Salmonella* and the host is utilized to deliver the Salp15 polynucleotide sequence to a target cell or tissue within a subject, wherein the Salp15 polypeptide is translated from the polynucleotide. Motameni et al., 2004 discloses representative methods for engineering the exemplary attenuated *Salmonella* host cells, and is incorporated herein by reference in its entirety.

In another aspect, a recombinant host cell is a prokaryotic host cell, including parasitic and bacterial cells. Preferably, a recombinant host cell is a bacterial cell, for example, a strain of *Escherichia coli*. The recombinant host cell can comprise a polynucleotide under the transcriptional control of regulatory signals functional in the recombinant host cell, wherein the regulatory signals appropriately control expression of the Salp15 polypeptide in a manner to enable all necessary transcriptional and post-transcriptional modification.

In yet another embodiment, provided is a process of preparing a Salp15 polypeptide comprising transfecting a cell with polynucleotide that encodes a biologically active Salp15 polypeptide as disclosed herein, to produce a transformed host cell, and maintaining the transformed host cell under biological conditions sufficient for expression of the polypeptide. The polypeptide can be isolated if desired, using any suitable technique. The host cell can be a prokaryotic or eukaryotic cell, such as, but not limited to a bacterial cell of *Salmonella* sp. or *Escherichia coli*. More preferably, a polynucleotide transfected into the transformed cell comprises the nucleotide base sequence of SEQ ID NOs: 16 or 17. SEQ ID NOs: 16-17 and 13-14 set forth nucleotide and amino acid sequences, respectively, for representative Salp15 polypeptides of the presently disclosed subject matter. Also provided are homologs or biologically equivalent Salp15 polynucleotides and polypeptides found in other vertebrates besides tick species.

As mentioned above, in connection with expression embodiments to prepare recombinant Salp15 and peptides, it is provided that longer DNA segments can be used, with DNA segments encoding the entire Salp15 protein, biologically active domains or cleavage products thereof, being most preferred. However, it will be appreciated that the use of shorter DNA segments to direct the expression of Salp15 peptides, epitopes or core regions, such as can be used to generate anti-Salp15 antibodies, also falls within the scope of the presently disclosed subject matter.

DNA segments which encode peptide antigens from about 5 to about 50 amino acids in length, or more preferably, from about 10 to about 30 amino acids in length are contemplated to be particularly useful. DNA segments encoding peptides will generally have a minimum coding length in the order of about 15 to about 150, or to about 90 nucleotides. DNA segments encoding full-length proteins can have a minimum coding length on the order of about 400 or 500 nucleotides for a protein in accordance with SEQ ID NO 1.

III.B. Peptide Modification Techniques and Derivatives

A Salp15 polypeptide or biologically functional equivalents thereof of the presently disclosed subject matter can be subject to various changes, substitutions, insertions, and deletions where such changes provide for certain advantages in its use. Thus, the term "polypeptide", "gene product" and "peptide" encompasses any of a variety of forms of peptide derivatives, that include amides, conjugates with proteins, cyclized peptides, polymerized peptides, conservatively substituted variants, analogs, fragments, peptoids, chemically modified peptides, and peptide mimetics. The modifications disclosed herein can also be applied as desired and as appropriate to antibodies.

Additional residues can also be added at either terminus of a peptide for the purpose of providing a "linker" by which the peptides of the presently disclosed subject matter can be conveniently affixed to a label or solid matrix, or carrier. Amino acid residue linkers are usually at least one residue and can be 40 or more residues, more often 1 to 10 residues, but do alone not constitute radiation inducible target ligands. Typical amino acid residues used for linking are tyrosine, cysteine, lysine, glutamic and aspartic acid, or the like. In addition, a peptide can be modified by terminal-$NH_2$ acylation (e.g., acetylation, or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half-life of the peptides in solutions, particularly biological fluids where proteases can be present.

Peptides of the presently disclosed subject matter can comprise naturally occurring amino acids, synthetic amino acids, genetically encoded amino acids, non-genetically encoded amino acids, and combinations thereof. Peptides can include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

III.B.1. Peptide Synthesis and Modification

Production of and modifications to the Salp15 proteins and peptides described herein can be carried out using techniques known in the art, including site directed mutagenesis and chemical synthesis.

Site-specific mutagenesis is a technique useful in the preparation of individual peptides, or biologically functional equivalent proteins or peptides, through specific mutagenesis of the underlying DNA. The technique further provides a ready ability to prepare and test sequence variants; for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983; Sambrook et al., 2001) and can be achieved in a variety of ways generally known to those of skill in the art.

Peptides of the presently disclosed subject matter, including peptoids, can also be chemically synthesized by any of the techniques that are known to those skilled in the art of peptide synthesis. Synthetic chemistry techniques, such as a solid-phase Merrifield-type synthesis, can be used for reasons of purity, antigenic specificity, freedom from undesired side products, ease of production, and the like. A summary of representative techniques can be found in Stewart & Young, 1969; Merrifield, 1969; Fields & Noble, 1990; and Bodanszky, 1993. Solid phase synthesis techniques can be found in Andersson et al., 2000, and in U.S. Pat. Nos. 6,015,561; 6,015,881; 6,031,071; and 4,244,946. Peptide synthesis in solution is described by Schröder & Lübke, 1965. Appropriate protective groups usable in such synthesis are described in the above texts and in McOmie, 1973. In addition, peptides comprising a specified amino acid sequence can be purchased from commercial sources (e.g., Biopeptide Co., LLC of San Diego, Calif., United States of America and PeptidoGenics of Livermore, Calif., United States of America).

III.B.2. Cyclic Peptides

Peptide cyclization is a useful modification because of the stable structures formed by cyclization and in view of the biological activities observed for such cyclic peptides as described herein. An exemplary method for cyclizing peptides is described by Schneider & Eberle, 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxyl termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

III.B.3. Peptoids

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al., 1993; Garbay-Jaureguiberry et al., 1992; Tung et al., 1992; Urge et al., 1992; Pavone et al., 1993.

III.B.4. Peptide Mimetics

The term "peptide mimetic" as used herein refers to a ligand that mimics the biological activity of a reference peptide, by substantially duplicating the targeting activity of the reference peptide, but it is not a peptide or peptoid. In one embodiment, a peptide mimetic is a small molecule having a molecular weight of less than about 700 daltons.

A peptide mimetic can be designed by: (a) identifying the pharmacophoric groups responsible for the targeting activity of a peptide; (b) determining the spatial arrangements of the pharmacophoric groups in the active conformation of the peptide; and (c) selecting a pharmaceutically acceptable template upon which to mount the pharmacophoric groups in a manner that allows them to retain their spatial arrangement in the active conformation of the peptide. For identification of pharmacophoric groups responsible for targeting activity, mutant variants of the peptide can be prepared and assayed for targeting activity. Alternatively or in addition, the three-dimensional structure of a complex of the peptide and its target molecule can be examined for evidence of interactions, for example the fit of a peptide side chain into a cleft of the target molecule, potential sites for hydrogen bonding, etc. The spatial arrangements of the pharmacophoric groups can be determined by NMR spectroscopy or X-ray diffraction studies. An initial three-dimensional model can be refined by energy minimization and molecular dynamics simulation. A template for modeling can be selected by reference to a template database and will typically allow the mounting of 2-8 pharmacophores. A peptide mimetic is identified wherein addition of the pharmacophoric groups to the template maintains their spatial arrangement as in the peptide.

A peptide mimetic can also be identified by assigning a hashed bitmap structural fingerprint to the peptide based on its chemical structure, and determining the similarity of that fingerprint to that of each compound in a broad chemical database. The fingerprints can be determined using fingerprinting software commercially distributed for that purpose by Daylight Chemical Information Systems, Inc. (Mission Viejo, Calif., U.S.A.) according to the vendor's instructions. Representative databases include but are not limited to SPREI'95 (InfoChem GmbH of Munchen, Germany), Index Chemicus (ISI of Philadelphia, Pa., U.S.A.), World Drug Index (Derwent of London, United Kingdom), TSCA93 (United States Environmental Protection Agency), Med-Chem (Biobyte of Claremont, Calif., U.S.A.), Maybridge Organic Chemical Catalog (Maybridge of Cornwall, England), Available Chemicals Directory (MDL Information Systems of San Leandro, Calif., U.S.A.), NCI96 (United States National Cancer Institute), Asinex Catalog of Organic Compounds (Asinex Ltd. of Moscow, Russia), and NP (Inter-BioScreen Ltd. of Moscow, Russia). A peptide mimetic of a reference peptide is selected as comprising a fingerprint with a similarity (Tanamoto coefficient) of at least 0.85 relative to the fingerprint of the reference peptide. Such peptide mimetics can be tested for binding to a substrate molecule, such as for example the CD4 co-receptor of T cells using the methods disclosed herein.

Additional techniques for the design and preparation of peptide mimetics can be found in U.S. Pat. Nos. 5,811,392; 5,811,512; 5,578,629; 5,817,879; 5,817,757; and 5,811,515.

III.B.5. Salts of Compositions

Any peptide or peptide mimetic of the presently disclosed subject matter can be used in the form of a pharmaceutically acceptable salt. Suitable acids which are capable of the peptides with the peptides of the presently disclosed subject matter include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the presently disclosed subject matter include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

IV. Introduction of Gene Products

In accordance with the present subject matter, where a Salp15 gene itself is employed to introduce a Salp15 gene product, a convenient method of introduction will be through the use of a recombinant vector that incorporates the desired gene, together with its associated control sequences. The preparation of recombinant vectors is well known to those of skill in the art and described in many references, such as, for example, Sambrook et al., 2001, incorporated herein in its entirety.

IV.A. Vector Construction

It is understood that the DNA coding sequences to be expressed, in this case those encoding the Salp15 gene products, are positioned in a vector adjacent to and operatively linked to a promoter (i.e., under the control of a promoter). It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

One can also desire to incorporate into the transcriptional unit of the vector an appropriate polyadenylation site (e.g., 5'-AATAAA-3'), if one was not contained within the original inserted DNA. Typically, these poly-A addition sites are placed about 30 to 2000 nucleotides "downstream" of the coding sequence at a position prior to transcription termination.

While use of the control sequences of the specific gene will be preferred, other control sequences can be employed, so long as they are compatible with the genotype of the cell being treated. Thus, one can mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the present subject matter can be any enhancer-promoter that drives expression in a cell to be transfected. By employing an enhancer-promoter with well-known properties, the level and pattern of gene product expression can be optimized.

For introduction of a Salp15 gene, a vector construct that will deliver the gene to cells of interest is desired. Viral vectors can be used. These vectors can optionally be a HSV-1, an adenovirus, a retrovirus, such as a Lentivirus, a vaccinia virus vector or an adeno-associated virus; these vectors have been successfully used to deliver desired sequences to cells and tend to have a high infection efficiency. Suitable vector-Salp15 gene constructs are adapted for administration as pharmaceutically acceptable formulation, as described herein below. Viral promoters can also be of use in vectors of the present subject matter, and are known in the art.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments can also be used, provided there is included the approximately 250 base pair sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral source, or can be provided by the host cell chromosomal replication mechanism. If the vector is integrated into the host cell chromosome, the latter is often sufficient.

As described herein, bacterial host cells can also be used to deliver a Salp15 to a cell or tissue of interest. See, for example, Motameni et al., 2004 for representative methods for delivering Salp15 genes and vectors to target tissues using a bacterial host cell. The Salp15 gene can be operatively linked to a eukaryotic promoter in these vectors such that the gene is not transcribed prior to delivery to the cell or tissue of interest.

Where a Salp15 gene itself is employed it will be most convenient to simply use a wild type Salp15 gene directly. However, it is provided that certain regions of a Salp15 gene can be employed exclusively without employing an entire wild type Salp15 gene, including fragments, and particularly fragments encoding the C-terminus of Salp15. Optionally, the smallest region needed to modulate biological activity so that one is not introducing unnecessary DNA into cells that receive a Salp15 gene construct can be employed. The ability of these regions to modulate biological activity can be determined by the assays reported in the Examples.

V. Methods Employing the Presently Disclosed Compositions

The presently disclosed subject matter provides isolated and purified biologically active Salp15 polypeptides and nucleic acid molecules encoding same. As disclosed herein, the Salp15 polypeptides are capable of specifically binding to $CD4^+$ T cells and modulating Class II MHC-mediated T-lymphocyte activation via the T cell receptor activation pathway of the $CD4^+$ T cells. The Salp15 polypeptides disclosed herein can modulate T cell activation via the specific binding to CD4 receptor molecules expressed on the surface of T cells. More particularly, the Salp15 polypeptides can bind the extracellular outer two domains (D1-D2) region of the CD4 receptor and thereby prevent propagation of the TCR-mediated activation signal, inhibiting activation of the T cell. The presently disclosed subject matter provides methods of employing these unique properties of Salp15 polypeptides, as discussed herein below.

V.A. Methods of Modulating T Cell Activation

The presently disclosed subject matter provides in some embodiments a method of modulating activation of a $CD4^+$ T cell due to T cell receptor-mediated signaling, comprising contacting the T cell with a Salp15 polypeptide as disclosed herein, where activation of the T cell is modulated. In some embodiments, T cell activation is inhibited by contacting the T cell with the Salp15 polypeptide. Thus, activation of the T cell (or a population of T cells overall) is decreased or substantially completely prevented. By inhibiting activation of the T cell, the T cell is unable to proliferate and differentiate, thereby dampening the immune response that otherwise would have been produced by the activated T cell or population of T cells.

In some embodiments, the Salp15 polypeptide comprises a polypeptide encoded by a nucleic acid sequence as set forth in any of SEQ ID NOs: 16 and 17; a polypeptide encoded by a nucleic acid having at least about 90% or greater sequence identity to a DNA sequence as set forth in any of SEQ ID NOs: 16 and 17; a polypeptide having an amino acid sequence of any of SEQ ID NOs: 13 and 14, or a biologically functional equivalent thereof; a polypeptide which is immunologically cross-reactive with antibodies which are immunologically reactive with a polypeptide having an amino acid sequence of any of SEQ ID NOs: 13 and 14; or a fragment of one of these Salp15 polypeptides.

In some embodiments, the Salp15 polypeptide is contacted with a T cell cultured in vitro. In other embodiments, the T cell is found within a subject and the Salp15 is contacted with the T cell by administering the Salp15 polypeptide to the subject. Therapeutic methods of administration are described in detail elsewhere herein.

V.B. Methods of Treating Disorders In Subjects

As discussed hereinabove and in the Examples, Salp15 polypeptides of the presently disclosed subject matter are useful to modulate CD4+ T cell activation. The Salp15 polypeptides bind CD4 receptor and inhibit activation of the T cell via the TCR-mediated signaling pathway, resulting in inhibition of IL-2 production and/or CD25 production (the IL-2 receptor). IL-2 mediated signaling is an important step in naïve T cell activation, and ultimately proliferation and differentiation. Thus, Salp15 polypeptides of the presently disclosed subject matter can inhibit inflammatory responses due at least in part to naïve $CD4^+$ T cell activation and therefore are useful for the treatment of disorders characterized by the activation of T cells, including but not limited to autoimmune disorders and tissue and organ transplant rejection.

V.B.1. Methods of Treating T Cell Response-Related Conditions

As such, the presently disclosed subject matter provides methods of treating a subject suffering from or at risk of suffering from a condition characterized by a $CD4^+$ T cell response, comprising administering to the subject an effective amount of a Salp15 polypeptide as disclosed herein.

In some embodiments, the Salp15 polypeptide comprises a polypeptide encoded by a nucleic acid sequence as set forth in any of SEQ ID NOs: 16 and 17; a polypeptide encoded by a nucleic acid having at least about 90% or greater sequence identity to a DNA sequence as set forth in any of SEQ ID NOs: 16 and 17; a polypeptide having an amino acid sequence of any of SEQ ID NOs: 13 and 14, or a biologically functional equivalent thereof; a polypeptide which is immunologically cross-reactive with antibodies which are immunologically reactive with a polypeptide having an amino acid sequence of any of SEQ ID NOs: 13 and 14; or a fragment of one of these Salp15 polypeptides.

In some embodiments the condition treated with the Salp15 polypeptide relates to inhibiting (reducing the risk of) rejection of transplanted tissues and/or organs. In these embodiments, the Salp15 polypeptide can be administered prior to, in conjunction with, and/or after transplantation of the tissue or organ. In some embodiments, the condition is an autoimmune disorder. Exemplary autoimmune disorders include but are not limited to lupus, rheumatoid arthritis, type 1 diabetes, multiple sclerosis, rheumatic fever, and Hashimoto's disease.

Effective dosages and formulations are chosen according to a number of factors, including but not limited to the particular subject, the condition treated and the severity of the condition, for example. Guidance regarding subjects treated, dosages and formulations is provided in detail elsewhere herein.

V.B.2. Methods of Treating Multiple Sclerosis

Multiple sclerosis (MS) is a chronic inflammatory disease of the central nervous system (CNS). Despite intensive investigation, the mechanisms of disease pathogenesis remain unclear, and curative therapies are unavailable for MS. Genetic predisposition, epidemiologic factors, and autoimmunity are all thought to be involved in the pathogenesis of MS (Vanderlugt et al., 2000). Self-reactive T cell activation and innate immune cell activation are thought to be major eliciting factors for the appearance of the symptomatology associated with the damage of the myelin sheath (Kuchroo et al., 2002). The inflammation associated with the disease is believed to be caused by the activation of $CD4^+$ T cells with a Th1 phenotype that produce IFNγ, activate innate immune cells and induce the production of complement-fixing antibody isotypes (Tran et al., 2002).

The study of MS has advanced dramatically with the use of different rodent models, including rats and mice. These studies have allowed a better understanding of how the rodent MS-like syndrome can be regulated, leading to therapeutic modalities which have been applied in clinical studies of MS patients. Some strains of mice develop a demyelinating inflammatory disease of the central nervous system known as Relapsing-remitting Experimental Autoimmune Encephalomyelitis (R-EAE) that mimics MS (McRae et al., 1992). R-EAE can be induced in a number of mouse strains (SJL, $(SWR\times SJL)F_1$). These mice are especially useful because the specificity of the eliciting antigen has been characterized to the peptide level and the hierarchy of epitope spreading has been determined (Lehmann et al., 1992; McRae et al., 1995; Yu et al., 1996). The animals, when immunized with a specific peptide from the myelin proteolipid protein (PLP) or Myelin Basic Protein (MBP) develop the MS-like syndrome R-EAE. The disease course in mice is similar to that found in humans: an initial bout of disease is followed by the remission of the symptoms (Goverman and Brabb, 1996).

Evidence exists that points to reactivation of memory T cells and/or epitope spreading (i.e. neoautoreactivity) to explain the chronicity and the relapsing-remitting clinical course often associated with the disease (Vanderlugt et al., 2000; McRae et al., 1995; Lehrnann et al., 1993). The animals present with relapsing episodes that are at least partially due to epitope spreading, which gives rise to the activation of new CD4+ T cells recognizing other CNS peptides. These include peptides present in PLP (intramolecular epitope spreading) or other proteins (MBP, MOG; intermolecular epitope spreading) (McRae et al., 1995). Therefore, control of these relapsing episodes could provide a way to evade progression of disease. Experiments carried out in the murine model have indicated that neoreactive CD4+ T cells are able to induce relapsing episodes, since 1) CD4+ T cells specific to relapse-associated epitopes can transfer the disease to naïve animals (Vanderlugt et al., 2000; McRae et al., 1995; Yu et al., 1996), 2) induction of peptide-specific tolerance to relapsing-associated epitopes during remission from acute disease prevents the progression of the disease (Vanderlugt et al., 2000), and 3) manipulation of costimulatory pathways required for T cell activation also modulates disease progression (Vanderlugt et al., 2000; Karandikar et al., 2000). Thus, it is likely that the inhibition of T cell activation in response to relapsing-associated epitopes during remission of the acute phase of the disease can reduce or even prevent the appearance of relapsing episodes.

Peptide specific disease therapy is difficult due to the diversity of peptides that can trigger relapsing episodes in humans. Alternative approaches include the inhibition of T cell activation using blocking antibodies to costimulatory molecules. The presently disclosed subject matter provides methods for administering Salp15 polypeptides disclosed herein as a treatment of patients with MS.

In some embodiments, the presently disclosed subject matter further provides a method of treating multiple sclerosis in a subject, comprising administering to the subject an effective amount of a Salp15 polypeptide as disclosed herein, or a biologically active fragment thereof, having immunosuppressive activity to the subject.

In some embodiments, the Salp15 polypeptide comprises a polypeptide encoded by a nucleic acid sequence as set forth in SEQ ID NO: 1; a polypeptide encoded by a nucleic acid having at least about 90% or greater sequence identity to a DNA sequence as set forth in SEQ ID NO: 1; a polypeptide encoded by a nucleic acid capable of hybridizing under stringent conditions to a nucleic acid comprising a sequence or the complement of a sequence as set forth in SEQ ID NO: 1; a polypeptide having an amino acid sequence of SEQ ID NO: 2, or a biologically functional equivalent thereof; a polypeptide which is immunologically cross-reactive with antibodies which are immunologically reactive with a polypeptide having an amino acid sequence of SEQ ID NO: 2; or a fragment of one of these Salp15 polypeptides, including but not limited to polypeptides having an amino acid sequence of SEQ ID NOs: 13 or 14, or a biologically functional equivalent thereof.

In some embodiments, the Salp15 polypeptide comprises a polypeptide encoded by a nucleic acid sequence as set forth in any of SEQ ID NOs: 16 and 17; a polypeptide encoded by a nucleic acid having at least about 90% or greater sequence identity to a DNA sequence as set forth in any of SEQ ID NOs: 16 and 17; a polypeptide having an amino acid sequence of any of SEQ ID NOs: 13 and 14, or a biologically functional equivalent thereof; a polypeptide which is immunologically cross-reactive with antibodies which are immunologically reactive with a polypeptide having an amino acid sequence of any of SEQ ID NOs: 13 and 14; or a fragment of one of these Salp15 polypeptides.

V.C. Methods of Inhibiting Infection of T Cells By HIV

Human immunodeficiency virus (HIV) is the etiologic agent of acquired immunodeficiency syndrome (AIDS). HIV is a human retrovirus of the Lentivirus group. The four recognized human retroviruses belong to two distinct groups: the human T lymphotropic (or leukemia) retroviruses, HTLV-1 and HTLV-2, and the human immunodeficiency viruses, HIV-1 and HIV-2. The former are transforming viruses whereas the latter are cytopathic viruses. As used herein, "HIV" refers to HIV-1 and HIV-2, and variant strains thereof.

The common denominator of AIDS is a profound immunosuppression, predominantly of cell-mediated immunity. This immune suppression leads to a variety of opportunistic diseases, particularly certain infections and neoplasms.

The main cause of the immune defect in AIDS has been identified as a quantitative and qualitative deficiency in the CD4+ T cells, which has been demonstrated to be the cellular receptor for HIV. Dalgleish et al., 1984. Although the T4 cell is the major cell type infected with HIV, essentially any human cell that expresses the CD4 molecule on its surface is capable of binding to and being infected with HIV.

HIV binds specifically and with high affinity, via a stretch of amino acids in the viral envelope protein Env (gp120), to a portion of the D1 region of the CD4 receptor located near its N-terminus. Following binding, the virus fuses with the target cell membrane and is internalized. Once internalized it uses the enzyme reverse transcriptase to transcribe its genomic RNA to DNA, which is integrated into the cellular DNA where it exists for the life of the cell as a "provirus."

The provirus may remain latent or be activated to transcribe mRNA and genomic RNA, leading to protein synthesis, assembly, new virion formation, and budding of virus from the cell surface. Although the precise mechanism by which the virus induces cell death has not been established, it is believed that the major mechanism is massive viral budding from the cell surface, leading to disruption of the plasma membrane and resulting osmotic disequilibrium.

During the course of the infection, the host organism develops antibodies against viral proteins, including the major envelope glycoproteins gp120 and gp41. Despite this humoral immunity, the disease progresses, resulting in a lethal immunosuppression characterized by multiple opportunistic infections, parasitemia, dementia, and death. The failure of the host anti-viral antibodies to arrest the progression of the disease represents one of the most vexing and alarming aspects of the infection, and augurs poorly for vaccination efforts based upon conventional approaches.

Evidence that the CD4-gp120 binding is responsible for viral infection of cells bearing the CD4 antigen (along with gp120 binding to a chemokine coreceptor) includes the finding that a specific complex is formed between gp120 and CD4 (McDougal et al., 1986). Other investigators have shown that cell lines, which were non-infective for HIV, were converted to infectable cell lines following transfection and expression of the human CD4 cDNA gene. Maddon et al., 1986.

Methods have previously been proposed for blocking HIV infection of T cells using molecules that can specifically block the binding of HIV gp120 to T cell CD4, thereby preventing infection of the T cells by HIV. For example, Capon et al. proposed the use of fusion polypeptides comprising the soluble four domains of CD4 (D1-D4) and an immunoglobulin Fc region, suggesting the fusion peptide would bind HIV gp120 and block gp120 interaction with CD4 on T cells. See Capon et al., 1989, incorporated herein by reference in its entirety. Arenzanz-Seisdedos et al. proposed utilizing a fragment of the RANTES chemokine having binding specificity for the CCR5 receptor, a coreceptor (along with CD4) utilized by HIV for infection of T cells. It was proposed the RANTES fragment could possibly inhibit infection by blocking gp120 interaction with CCR5. See Arenzanz-Seisdedos et al., 1996, incorporated herein by reference in its entirety.

The presently disclosed subject matter provides methods of blocking HIV infection by blocking effective gp120 binding to CD4. As disclosed herein, Salp15 binds with specificity at the D1-D2 domains of CD4. As demonstrated in the Examples, specific binding of Salp15 to CD4 can effectively block binding of gp120 to CD4. Thus, Salp15 polypeptides disclosed herein can be utilized to inhibit HIV infection of T cells, including in vivo, by blocking gp120 binding of CD4. One of skill in the art will appreciate that in some circumstances, it will be desirable to utilize Salp15 polypeptides, fragments, or mimetics thereof that only block binding of gp120 to CD4 and do not further cause modification to CD4 structure such that T cell activation is inhibited resulting in immunomodulation. Such peptides could be particularly preferred for use in subjects whose immune systems are previously suppressed, due to for example previous infection by HIV. Therefore, Salp15 polypeptides exhibiting these qualities are encompassed by the presently disclosed subject matter as well.

In some embodiments, the presently disclosed subject matter provides a method of inhibiting infection of a T cell by a human immunodeficiency virus (HIV), comprising contacting a CD4 receptor expressed by the T cell with a Salp15 polypeptide, or a biologically active fragment thereof having binding specificity for the CD4 receptor, whereby contacting the Salp15 polypeptide with the CD4 receptor inhibits the HIV from infecting the T cell.

In some embodiments, the Salp15 polypeptide comprises a polypeptide encoded by a nucleic acid sequence as set forth in SEQ ID NO: 1; a polypeptide encoded by a nucleic acid having at least about 90% or greater sequence identity to a DNA sequence as set forth in SEQ ID NO: 1; a polypeptide encoded by a nucleic acid capable of hybridizing under stringent conditions to a nucleic acid comprising a sequence or the complement of a sequence as set forth in SEQ ID NO: 1; a polypeptide having an amino acid sequence of SEQ ID NO: 2, or a biologically functional equivalent thereof; a polypeptide which is immunologically cross-reactive with antibodies which are immunologically reactive with a polypeptide having an amino acid sequence of SEQ ID NO: 2; or a fragment of one of these Salp15 polypeptides, including but not limited to polypeptides having an amino acid sequence of SEQ ID NOs: 13 or 14, or a biologically functional equivalent thereof.

In some embodiments, the Salp15 polypeptide comprises a polypeptide encoded by a nucleic acid sequence as set forth in any of SEQ ID NOs: 16 and 17; a polypeptide encoded by a nucleic acid having at least about 90% or greater sequence identity to a DNA sequence as set forth in any of SEQ ID NOs: 16 and 17; a polypeptide having an amino acid sequence of any of SEQ ID NOs: 13 and 14, or a biologically functional equivalent thereof; a polypeptide which is immunologically cross-reactive with antibodies which are immunologically reactive with a polypeptide having an amino acid sequence of any of SEQ ID NOs: 13 and 14; or a fragment of one of these Salp15 polypeptides.

In some embodiments, the Salp15 polypeptide is contacted with a T cell cultured in vitro. In other embodiments, the T cell is found within a subject and the Salp15 is contacted with the T cell by administering the Salp15 polypeptide to the subject. Methods of administration are described in detail elsewhere herein.

V.D. Subjects

Further with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

V.E. Formulations

A composition as described herein preferably comprises a composition that includes a carrier. In some embodiments, particularly with regard to the therapeutic methods, the carrier is a pharmaceutically acceptable carrier in mammals, e.g. humans. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The composition can be formulated according to the mode of administration, which can include, but is not limited to systemic administration, parenteral administration (including intravascular, intramuscular, and intraarterial administration), oral delivery, buccal delivery, subcutaneous administration, inhalation, intratracheal instal-lation, surgical implantation, transdermal delivery, local injection, and hyper-velocity injection/bombardment or combinations thereof of administration modes.

The compositions used in the methods can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a Salp15 polypeptide, including biologically active fragments and modified polypeptides, and polypeptide mimetics, can be formulated in combination with hydrochlorothiazide, and as a pH stabilized core having an enteric or delayed release coating which protects the active agents until reaching desired regions of the gastrointestinal tract.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

V.F. Doses

The term "effective amount" is used herein to refer to an amount of a composition (e.g., a composition comprising a Salp15 polypeptide) sufficient to produce a measurable biological response (e.g., a measurable inhibition in T cell activation). Actual dosage levels of active ingredients in a composition of the presently disclosed subject matter can be varied so as to administer an amount of the active compound(s) that is effective to achieve the desired response for a particular subject and/or application. The selected dosage level will depend upon a variety of factors including the activity of the composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., 1966). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al., 1966. Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

For oral administration, a satisfactory result can be obtained employing the Salp15 polypeptide in an amount ranging from about 0.01 mg/kg to about 100 mg/kg and preferably from about 0.1 mg/kg to about 30 mg/kg. A preferred oral dosage form, such as tablets or capsules, will contain the Salp15 polypeptide in an amount ranging from about 0.1 to about 500 mg, preferably from about 2 to about 50 mg, and more preferably from about 10 to about 25 mg.

For parenteral administration, the Salp15 polypeptide can be employed in an amount ranging from about 0.005 mg/kg to about 100 mg/kg, preferably about 10 to 50 or 10 to 70 mg/kg, and more preferably from about 10 mg/kg to about 30 mg/kg.

For additional guidance regarding formulation and dose, see U.S. Pat. Nos. 5,326,902; 5,234,933; PCT International Publication No. WO 93/25521; Berkow et al., 1997; Goodman et al., 1996; Ebadi, 1998; Katzung, 2001; Remington et al., 1975; Speight et al., 1997; and Duch et al., 1998.

V.G. Routes of Administration

Suitable methods for administering to a subject a Salp15 polypeptide in accordance with the methods of the presently disclosed subject matter include but are not limited to systemic administration, parenteral administration (including intravascular, intramuscular, and intraarterial administration), oral delivery, buccal delivery, subcutaneous administration, inhalation, intratracheal installation, surgical implantation, transdermal delivery, local injection, and hypervelocity injection/bombardment. Where applicable, continuous infusion can enhance drug accumulation at a target site (see, e.g., U.S. Pat. No. 6,180,082).

The particular mode of administration used in accordance with the methods of the present subject matter depends on various factors, including but not limited to the vector and/or carrier employed, the severity of the condition to be treated, and mechanisms for metabolism or removal of the drug following administration.

V.H. Screening Methods

As discussed herein, Salp15 can bind with specificity to an extracellular region of the CD4 co-receptor, which results in an inability of the CD4 receptor to participate effectively in the TCR-mediated signaling pathway. As a result, the T cell expressing the bound CD4 will be inhibited in whole or part from becoming activated by the TCR-mediated signal, and therefore will not undergo the proliferation or differentiation process, and instead remaining quiescent. Further, as discussed herein, the presently disclosed subject matter provides compositions with the same biological activity as Salp15, which is based on an ability to bind also with specificity the CD4 receptor. Methods of screening for compounds with the desired activity are thus also provided.

A method of screening candidate substances for an ability to modulate activation of a CD4$^+$ T cell is provided in accordance with the presently disclosed subject matter. In some embodiments, the method comprises (a) establishing a test sample comprising a CD4 receptor polypeptide and a ligand for the CD4 receptor polypeptide, wherein the ligand is a Salp15 polypeptide; (b) administering a candidate substance or a sample suspected of containing a candidate substance to the test sample; and (c) measuring an effect of the candidate substance on binding of the CD4 receptor polypeptide and the ligand in the test sample. In some embodiments, the measuring can comprise determining the ability of the candidate substance to modulate activation of a $CD4^+$ T cell resulting from T cell receptor-mediated signaling. Further, in some embodiments, the measuring can comprise determining whether or not the candidate substance can block binding of the CD4 receptor polypeptide and the ligand.

The test sample can further comprise an indicator. The term "indicator" is meant to refer to a chemical species or compound that is readily detectable using a standard detection technique, such as dark versus light detection, fluorescence or chemiluminescence spectrophotometry, scintillation spectroscopy, chromatography, liquid chromatography/mass spectroscopy (LC/MS), colorimetry, and the like. Representative indicator compounds thus include, but are not limited to, fluorogenic or fluorescent compounds, chemiluminescent compounds, calorimetric compounds, UV/VIS absorbing compounds, radionucleotides and combinations thereof. In a preferred embodiment, the ligand further comprises an indicator.

The ability of the candidate substance to modulate activation of a $CD4^+$ T cell can determined in any suitable manner. For example, the ability of the candidate substance to modulate activation of a $CD4^+$ T cell can determined by: (i) detecting a signal produced by the indicator upon an effect of the candidate substance on binding of the CD4 receptor polypeptide and the ligand; and (ii) identifying the candidate substance as a modulator of activation of a $CD4^+$ T cell based upon an amount of signal produced as compared to a control sample.

In some embodiments, a fluorescence based screening methodology is utilized to identify compositions that can bind with specificity at a region of the CD4 receptor such that the composition competitively inhibits the ligand Salp15 from binding the CD4 receptor. The method is readily amenable to both robotic and very high throughput systems.

Thus, in one embodiment, a screening method of the present subject matter pertains to a method for a identifying a candidate substance for an ability to modulate activation of a $CD4^+$ T cell due to T cell receptor-mediated signaling. The method comprises establishing a test sample comprising a CD4 receptor and a candidate substance, administering to the test sample a Salp15 peptide (a ligand for CD4) comprising an indicator, incubating the sample for a sufficient time to allow interaction of the ligand with the CD4 receptor; and detecting a signal produced by the indicator; and identifying the candidate substance as having an ability to modulate activation of a $CD4^+$ T cell due to T cell receptor-mediated signaling based upon an amount of signal produced by the indicator as compared to a control sample, which did not contain the candidate substance. In the presence of a candidate substance capable of binding CD4 at the same region as Salp15, the candidate substance will compete for binding of CD4 with Salp15. The greater the affinity of the candidate substance for CD4 at the region where Salp15 binds, the lower the amount of signal produced and the more promising the candidate substance as a modulator of T cell activation.

In some embodiments, the candidate substance is a polypeptide, and in some embodiments, the polypeptide is an antibody or functional equivalent fragment thereof. Functional fragments of antibodies are described in detail herein. In some embodiments, a nucleic acid molecule encoding the candidate polypeptide is isolated and purified. Alternatively, in some embodiments, the candidate substance is a small molecule, such as a peptide mimetic of Salp15. Peptide mimetics are described in detail elsewhere herein.

In another embodiment of the screening method of the presently disclosed subject matter, a Salp15 polypeptide or active fragment thereof, and a CD4 receptor can be used for screening libraries of compounds in any of a variety of high throughput drug screening techniques. The components employed in such screening may be free in solution, affixed to a solid support, borne on a cell surface, or located intracellularly. For example, in some embodiments, the CD4 receptor or an extracellular fragment thereof is immobilized to a solid support and the Salp15 polypeptides and candidate substances are allowed to compete for binding to the immobilized CD4 receptor. The solid support can then be easily washed to remove unbound substances. The formation of binding complexes, between the Salp15 polypeptide or candidate substance with the CD4 receptor, can then be measured as described herein.

EXAMPLES

The following Examples provide illustrative embodiments. Certain aspects of the following Examples are disclosed in terms of techniques and procedures found or contemplated by the present inventors to work well in the practice of the embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Materials and Methods for Examples 1-5

Cell Purification and Activation

Naïve CD4+ T cells from C3H/HeN, Balb/c, and B10.BR mice were purified as previously described (Anguita et al., 2002). CD4+ T cells were preincubated in Click's modified Bruff's Medium (Sigma Chemical Co., St. Louis, Mo., U.S.A.) for 10 minutes at 37° C. with and without Salp15 (50 μg/mL) and stimulated for 20 min or the indicated times at 37° C. with 10 μg/mL of anti-CD3ϵ, 1 μg/mL of anti-CD28, and 10 μg/mL of anti-armenian and syrian hamster IgG (BD Biosciences Pharmingen, San Jose, Calif., U.S.A.). Jurkat (E6-1) cells were stimulated using 5 μg/mL of OKT3 mAb (eBioscience, San Diego, Calif., U.S.A.) and 1 μg/mL of anti-human CD28 cross linked with 5 μg/mL anti-mouse IgG for the indicated times.

Antibodies

The anti-p-LAT (Tyr191), anti-pSrc family (Tyr416), anti-LCK, anti-Vav1, anti-pZap70 (Tyr319), anti-Zap-70, p44/42, p44/42 (phopho-Tyr204/Thr202), anti-pSTAT1 and anti-STAT1 were purchased form Cell Signaling Technologies (Beverly, Mass., U.S.A.). Anti-pTyr (pY99), antipPLCγ1 (Tyr783), anti-PLCγ1, polyclonal anti-CD4, MT310, anti-CD3, anti-CD28, anti-TCRβ and normal rabbit IgG were purchased form Santa Cruz Biotechnology (Santa Cruz, Calif., U.S.A.). The polyclonal anti-His-HRP antibody was purchased form Novus Biologicals (Littleton, Colo., U.S.A.). OKT4 was purchased from eBioscience.

Confocal Microscopy

For the visualization of lipid rafts, phospho-tyrosine, and cytoskeleton reorganization, $CD4^+$, $CD8^+$ or Jurkat cells were cytospun for 10 minutes at 1000 RPM onto positively charged microslides (Fisher Scientific, Hampton, N.H., U.S.A.). The cells were fixed with 3.7% paraformaldehyde (Sigma Chemical Co.) for 15 minutes and stained with CTB$_{594}$ (Molecular Probes, Eugene, Oreg., U.S.A.), AlexaFluor$_{488}$ labeled phalloidin (Molecular Probes) or (1:50) biotin-conjugated anti-p-Tyr (PY99) followed by Streptavidin-AlexaFluor$_{594}$ (1:100, Molecular Probes). For p-LAT and p-PLCγ1 staining, fixed cells were treated with PBS containing 0.1% Triton-X 100 and 100 mM glycine for 15 min at room temperature and stained using rabbit p-LAT (Tyr$^{191}$) or rabbit anti-p-PLCγ1 (Tyr$^{783}$) probed with anti-rabbit IgG$_{488}$ (Molecular Probes).

For receptor capping studies, mouse primary B and CD11$^+$ cells were purified by positive selection using biotin anti-mouse CD45R/B220 clone RA3-6B2 and biotin anti-mouse CD11b clone M1/70 (BD Biosciences Pharmingen) respectively, followed by incubation with magnetic microbeads. The cells were analyzed for receptor capping using 25 μg/mL anti-mouse IgM and 25 μg/mL anti-mouse CD16/CD32 respectively, cross-linked with 25 μg/mL of anti-rat IgG594 for 10 min in the presence or absence of 50 μg/mL of Salp15. CD4$^+$ and CD8$^+$ T cells were purified by negative selection and incubated with 10 μg/mL anti-CD3 and 1 μg/mL anti-CD28 cross-linked with 10 μg/mL of anti-hamster IgG$_{488}$ for 10 min in the presence or absence of 50 μg/mL of Salp15.

For colocalization experiments, Jurkat and CD4$^+$ T cells were cytospun as described herein. HeLa and HeLa-CD4 cells were grown on chamber slides. The cells were fixed and stained with anti-CD4 and Salp15 as follows. Purified Salp15 was labeled using Alexa-488 with the Protein Labeling Kit (Molecular Probes) according to the manufacturer's instructions. Fixed cells were blocked with 5% normal serum and anti-CD16/CD32 (1:100) in PBS, incubated with 1 μg of monoclonal biotinylated anti-CD4 (L3T4) (BD Biosciences Pharmingen) followed by streptavidin$_{594}$ staining. The cells were then stained with 20 μg/mL of Salp15$_{488}$. For competition assays, cells were first blocked with 5% normal serum, incubated with either polyclonal anti-CD4 antibody, MT310, OKT4, normal rabbit IgG, Salp15 (0.5 mg/mL) or lysozyme (0.5 mg/mL) followed by staining with Salp15$_{488}$. All samples were mounted in a GVA Mount (Zymed, San Francisco, Calif., U.S.A.) and visualized with an Olympus Confocal microscope equipped with Fluoview 3.0 software.

Western Blotting and Co-Immunoprecipitation

For tyrosine phosphorylation western analysis, cells were lysed in 60 mM Tris (pH 7.4) containing 150 mM NaCl, 5 mM EDTA, 1 mM EGTA, 1 mM β-glycerol phosphate, 2.5 mM sodium pyrophosphate, 25 mM NaF, 2 mM sodium orthovanadate, 1% Triton-X 100, 0.25% sodium deoxycholate, 1 mM PMSF and protease inhibitors for 15 min on ice, sonicated 4×5 sec and incubated at 37° C. for 10 min. The lysate was cleared by centrifugation and boiled in SDS-sample buffer. The samples were subjected to SDS-PAGE, transferred to a nitrocellulose membrane and immunoblotted with anti-pTyr, anti-pPLCγ1 and anti-Vav1, anti-pSrc family (Tyr$^{416}$) to measure p-Lck$^{394}$ (Alonso et al., 2004), anti-Lck, anti-pZap70 (Tyr$^{319}$), anti-Zap70, p44/42 and p44/42 (phospho-Tyr$^{204}$/Thr$^{202}$). Vav1 was immunoprecipitated using anti-Vav1 and protein A-agarose beads overnight, subjected to SDS-PAGE followed by immunoblotting with anti-pTyr or anti-Vav1. To examine the effect of Salp15 on T cell stimulation with INFγ, CD4$^+$ T cells were preincubated with Salp15 at 50 μg/mL followed by activation with 20 ng/mL of mouse recombinant INFγ (R & D Systems, Minneapolis, Minn., U.S.A.) for 30 min at 37° C. The cells were lysed as above and subjected to SDS-PAGE and immunoblotting with anti-pSTAT1 and anti-STAT1.

For coimmunoprecipitation, 1-2×10$^7$ Jurkat, HeLa or HeLa-CD4 cells were lysed in 20 mM HEPES pH 7.4 containing 150 mM NaCl, 1% Triton-X 100, 0.25% sodium deoxycholate, 25 mM NaF, 2 mM Na3VO4, 1 mM PMSF and protease inhibitors for 15 min on ice. One mg of protein equivalent of the cell lysate was mixed with 50 μg/mL of 6× histidine-tagged-Salp15 or 6×His-tagged Salp13 fused to thioredoxin (29 kD) as a control protein, (Anguita et al., 2002, Das et al., 2001) and immunoprecipitated using an anti-poly-histidine antibody conjugated to agarose, anti-CD4, anti-CD3, anti-CD28 or normal rabbit IgG overnight at 4° C. The immunoprecipitate was run on SDS-PAGE followed by immunoblotting with anti-poly His-HRP, anti-CD4, anti-CD3, anti-CD28 or anti-TCRβ.

Quantification of immunoblots was performed using the SCION IMAGE™ software package, Scion Corporation (Frederick, Md., U.S.A.).

Flow Cytometry

Actin polymerization assay was performed as described earlier (Krishnan et al., 2004). Briefly, 0.5×106 CD4+ T cells were fixed with 3.7% paraformaldehyde for 8 min. The fixed cells were washed with PBS twice and permeabilized and stained with staining buffer containing 0.1% Triton X-100, 0.2 μM phalloidin488, 5% BSA and 0.2 mg/mL APC-conjugated L3T4 monoclonal antibody (BD Biosciences Pharmingen) for 40 min. The cells were washed, resuspended in PBS and analyzed for F-actin content on a FACSCalibur with CellQuest software (Beckton Dickinson, Mountain View, Calif., U.S.A.). For the Salp15 binding assays, the suspended cells were first blocked with PBS containing 5% BSA and 0.1% sodium azide for 10 min, washed with PBS containing 1% BSA followed by staining with Salp15 binding solution containing 15 μg/106 cells of Salp15488, 5% BSA and 0.1% sodium azide in PBS for 30 min. The cells were washed twice with PBS and analyzed by flow cytometry.

F-Actin Quantification

The amount of F-actin in activated CD4+ T cells in the presence and absence of Salp15 was quantified by ultracentrifugation and Western blotting. CD4$^+$ T cells were activated as described above for 2 min. Cells were lysed in HEPES buffer containing Triton X-100 (10 mM NaCl, 135 mM KCl, 2 mM MgCl2, 2 mM EGTA, 10 mM HEPES pH 7.15, 1% Triton X-100, 0.01 mg/ml aprotinin, 0.01 mg/ml leupeptin, 1 mM PMSF). The cell lysates were centrifuged for 5 min at 12,000×g at 4° C. in a table top centrifuge. The supernatant was then centrifuged in a Beckman ultracentrifuge, rotor TLA.100.2, for 30 min at 320,000×g at 4° C. The remaining pellet containing F-actin was solubilized in SDS loading buffer overnight on ice. The samples were subjected to SDS-PAGE followed by Western blotting. Equal amounts of total protein were loaded on the SDS-gel based on the total actin determined from a sample of the cell lysate.

Cell Activation from DO11.10 Transgenic and CD4-Deficient Mice

T-cells from CD4-deficient and B6 mice (The Jackson Laboratory, Bar Harbor, Me., U.S.A.) were purified by negative selection and activated for 72 hrs using 5 μg/ml of plate bound anti-CD3 and 1 μg/ml of anti-CD28 in the presence or absence of 50 μg/mL of Salp15. DO11.10 transgenic mouse (The Jackson Laboratory) CD4$^+$ T cells were purified by negative selection as before and incubated in the presence of 106/mL of syngeneic mitomycin C-treated (50 μg/ml for 40 min at 37° C.) antigen presenting cells (APCs) with 10 μg/mL of ovalbumin in the presence of 0.5, 5.0 and 50 μg/mL of Salp15 for 72 hrs. The supernatants were then collected and IL-2 measured by capture ELISA following the manufacturer's instruction (BD Biosciences Pharmingen).

Microtiter Binding Assay

Purified sCD4 was coated overnight at 4° C. at the indicated concentrations in 0.1M sodium carbonate buffer (pH 9.5) in 96 well plates. Equimolar amounts of lysozyme were used as a non-specific control. The wells were washed, blocked with 10% FCS/PBS for 1 hr at R.T., and incubated with Salp15 (0.4 µM) for 2 hr at 37° C. Salp15 binding was detected by incubation with horseradish peroxidase (HRP)-conjugated anti-His antibody for 1 hr followed by microwell peroxidase substrate (KPL). The reaction was stopped by adding TMB stop solution (KPL). Chemically synthesized overlapping peptides of Salp15 were purchased from GenScript Corporation (Piscataway, N.J., U.S.A). To study the binding of Salp15 and peptides to sCD4, Salp15 (5 µg) and different peptides (0.5 µg) were coated. The wells were washed and blocked prior to incubation with sCD4-HRP (Research Diagnostics Inc., Flanders, N.J., U.S.A.). For competition assays, indicated concentrations of Salp15 or P11 were added to sCD4-HRP and incubated with plate bound P11 (0.1 µg). To estimate the effect of dithiothreitol (DTT) treatment of Salp15 on binding to sCD4, 0.5 µM Salp15 was treated with 10 mM DTT overnight and immobilized onto microtiter plate followed by blocking and incubation with sCD4-HRP.

Analytical Gel Filtration

Purified sCD4 (D1-D4, 10 µg) and Salp15 (20 µg) were eluted through two SUPERDEX-200™ HR 10/30 gel filtration columns (Amersham Pharmacia Biotech, Piscataway, N.J., U.S.A.) connected in tandem using PBS as equilibration and elution buffer at a flow rate of 0.3 mL/min using an FPLC system (Amersham Pharmacia Biotech) equipped with a liquid chromatography controller LCC-501 Plus and regulated using FPLC director V1.10. To get the elution profile of the Salp15-CD4 complex, Salp15 was incubated with sCD4 before passing it through the gel filtration column. Blue dextran was used to estimate the void volume of the columns, while BSA, ovalbumin and lysozyme were used as molecular weight standards with elution volumes of 14.78 mL, 26.45 mL, 28.45 mL and 39.28 mL, respectively.

Native Gel Electrophoresis

Purified sCD4 (D1-D4, 10 µg), Salp15 (10 µg) and sCD4 (10 µg)+Salp15 (10 µg) were diluted into 50% glycerol, 40 mM HEPES (pH 6.5) and 50 mM imidazole (pH 6.5). The native gel [5% Acrylamide:Bis (29:1), 40 mM HEPES (pH 6.5), 50 mM imidazole (pH 6.5) and 10% glycerol] electrophoresis was performed using a 40 mM HEPES (pH 6.5) running buffer and 50 mM imidazole (pH 6.5) at 8 mAmps for 1.5 hours at 4° C. The gel was stained with coomassie blue or transferred to IMMOBILON P® (Millipore) blotting paper for immunoblotting with anti-Poly His-HRP and anti-CD4.

Ellman Assay

The solutions used for Ellman assay were solution A (37 mM sodium phosphate buffer, pH 8.0), solution B (7.4 mM sodium phosphate buffer, pH 8.1), solution C (25 mM EDTA in solution B), solution D (10 mM DTNB (Sigma) in solution A) and solution E (protein samples in solution B). The solutions to be measured on a spectrophotometer were prepared as follows: (1) the reagent blank contained 240 µL C, 60 µL D and 900 µL B; (2) the reaction mixture contained 20 µL C, 5 µL D and 75 µL E; (3) the protein blank was prepared by mixing 20 µL A, 5 µL D and 75 µL E; and (4) the buffer blank was made by mixing 240 µL A, 60 µL D and 900 µL B. These solutions were incubated at 25° C. for 45 min before reading the absorbance at 412 nm. The final absorbance, A was defined as:

$$A = A_{DTNB} - A_{protein} \quad \text{(Eq. 1)}$$

where ADTNB is the absorbance for solution 2 minus solution 1, and Aprotein is absorbance for solution 3 minus solution 4. The concentration of free thiol in solution 2 was then calculated using the formula:

$$A = \epsilon L [Salp15-SH] \quad \text{(Eq. 2)}$$

where $\epsilon$ is equal to 14150 M-1 cm-1. The concentration of free thiol in solution 2 was corrected for dilution and percentage of free thiol content of Salp15 was calculated as:

$$\text{Free thiol \%} = [Salp15-SH] \times 100 / [Salp15] \quad \text{(Eq. 3)}$$

where the concentration of Salp15 was obtained using the Bradford assay.

Statistical Analysis

Dissociation constants were determined by non-linear curve fit. The results are expressed as the mean±S.E. of 3 to 5 individual experiments.

Example 1

Salp15 Inhibits Early Protein Tyrosine Phosphorylation During T Cell Activation

During TCR signaling, PLCγ1 hydrolyzes phosphatidylinositol (4,5)-bisphosphate to inositol (1,4,5)-trisphosphate and diacylglycerol, leading to calcium mobilization and protein kinase-C activation, respectively (Rhee and Bae, 1997). It was first questioned whether PLCγ1 activation, regulated by its phosphorylation at Tyr783 (Mustelin et al., 1990), was affected by Salp15 treatment of T lymphocytes. Phosphorylation of PLCγ1 was reduced in stimulated mouse $CD4^+$ T lymphocytes which were pretreated with Salp15, compared to control treated cells (46%, FIG. 1A). This inhibition was also evident in the Jurkat clone E6-1, a human T cell leukemia cell line, suggesting that Salp15 is equally effective in causing immunosuppression in human T cells.

Figure 1B:
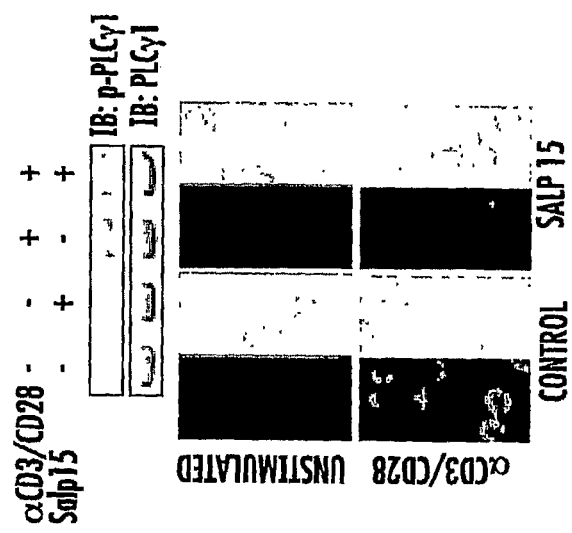
Figure 1C:
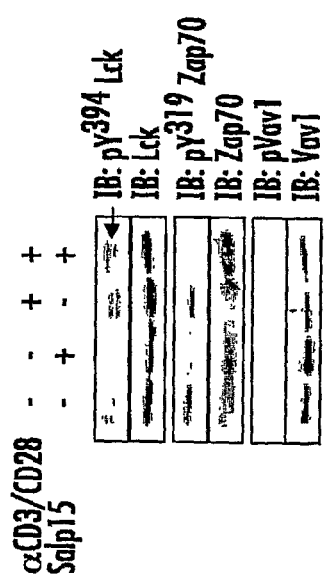
Figure 7B:
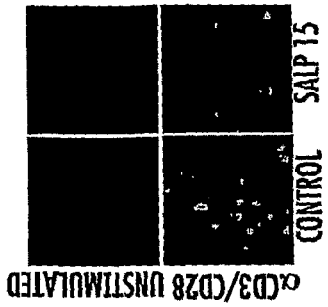
FIGS. 7A-7E show Salp15 inhibits early T cell activation events in Jurkat cells.
Figure 7C:
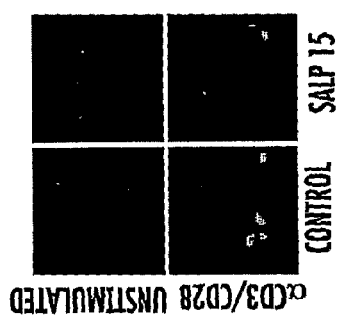
Figure 7E:
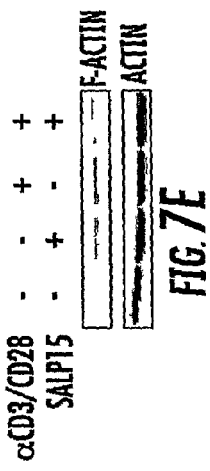
Figure 7A:
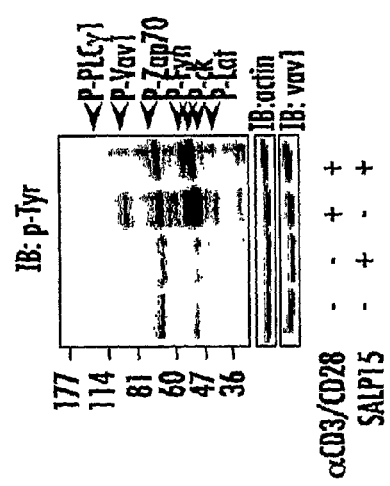

To investigate whether the upstream signaling pathways resulting in PLCγ1 activation were also affected by Salp15 treatment, the tyrosine phosphorylation of membrane bound and cytosolic proteins induced by TCR ligation in the presence or absence of Salp15 was examined. TCR ligation-induced tyrosine phosphorylation of several proteins was lowered to different degrees by pretreatment of $CD4^+$ T cells with Salp15 (FIG. 1B and FIG. 7A). The molecular weights of these proteins corresponded to those of Lck, Vav1, Lat, and Zap70, which was further confirmed by assessing the phosphorylation status of some of these signaling components individually by using phospho-specific antibodies. The phosphorylation levels of Lat at $Tyr^{191}$ (FIG. 1B), Lck at $Tyr^{394}$ and Zap70 at $Tyr^{319}$ (FIG. 1C) were reduced by Salp15 pretreatment. Salp15 also inhibited TCR ligation-induced tyrosine phosphorylation of Vav1 as examined by immunoprecipitation of total Vav1 followed by anti-pTyr immunoblotting (FIG. 1C).

The reduction in tyrosine phosphorylation of Lck, Zap70 and Vav1 by Salp15 pretreatment was estimated to be about 56%, 67% and 58%, respectively by quantification of the specific bands. The inhibitory effects of Salp15 on TCR ligation-induced tyrosine phosphorylation were also observed in Jurkat cells (FIG. 7B). These results suggest that Salp15 exerts a specific decrease in tyrosine phosphorylation of signaling proteins upon activation of T cells by anti-CD3/CD28.

Example 2

Reduced Lipid Raft Re-Organization in Salp15 Treated Activated T Lymphocytes

Lipid rafts, which are discrete plasma membrane lipid microdomains rich in glycosphingolipids, cholesterol and glycosphosphatidyl inositol-linked proteins (Simons and Ikonen, 1997), play a central role in TCR-induced signal transduction by segregating signaling molecules in resting cells and providing a compartment for their association and activation upon receptor engagement (Alonso and Millan, 2001). Otherwise dispersed over the cell surface as small domains, the lipid rafts coalesce in response to TCR engagement, amplifying and sustaining TCR-induced signals (Rodgers and Rose, 1996; Viola et al., 1999). Thus, whether Salp15 pretreatment affected lipid raft reorganization during CD4+ T cell activation in response to anti-CD3/CD28 signals was investigated. The redistribution of rafts was assessed using Alexa-fluor$^{594}$-labeled cholera-toxin B (CTB$^{594}$) which binds to the ganglioside GM1 enriched in lipid rafts. CTB$^{594}$ staining of the stimulated CD4$^+$ T cell membrane was confined in a dense cap structure, as described (Janes et al., 2000) in contrast to unstimulated T cells (FIG. 2A), indicating that rafts had aggregated during the activation process. Lipid raft clustering, however, was reduced by Salp15 treatment prior to the stimulation with anti-CD3/CD28 in both murine cells (FIG. 2A) as well as Jurkat cells (FIG. 7C).

Lipid raft re-organization is not exclusive for CD4$^+$ T cells and is also involved in signaling processes in other cell types such as CD8$^+$ T cells, B cells and Fc receptor bearing cells. To examine the influence of Salp15 in these cell types, receptor capping in T, B and phagocytic cells in response to anti-CD3/CD28, anti-IgM and Fc engagement, respectively, using fluorescent-labeled cross linking antibodies were analyzed. Salp15 did not affect lipid raft reorganization in B cells and macrophages, while clustering was reduced in CD4$^+$ T cells (FIG. 2B). Lipid raft reorganization during CD8$^+$ T cell activation in response to anti-CD3/CD28 signals was also unaffected by Salp15 pretreatment as determined by CTB$^{594}$ staining (FIG. 2C). Without wishing to be bound by theory, this suggests that Salp15 does not affect lipid raft reorganization per se, but affects the CD4$^+$ T cell specific upstream pathways leading to lipid raft clustering upon activation. Again, without wishing to be bound by theory, this inhibition of lipid raft clustering could partly explain the immunosuppressive effect of Salp15 on T lymphocytes by inhibiting the amplification of primary signaling events induced by TCR ligation.

Example 3

Salp15 Inhibits Actin Polymerization in Activating T Lymphocytes

Figure 7D:
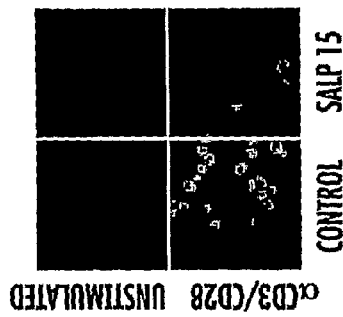

Lipid raft redistribution is regulated by critical cytoskeletal changes including polymerization of globular (G)-actin into filamentous (F)-actin (Valensin et al., 2002) that occur upon TCR/CD3 complex engagement. To determine whether Salp15 pretreatment affected actin polymerization induced by T cell activation, Alexa-fluor$_{488}$-labeled phalloidin was used to visualize the extent of F-actin formation by confocal microscopy. Phalloidin$_{488}$ staining was high in activated CD4$^+$ T cells compared to naïve cells (FIG. 3A), while the extent of phalloidin$_{488}$ staining was reduced in activated murine CD4$^+$ T (FIG. 3A) and Jurkat cells (FIG. 7D) pretreated with Salp15. This effect was further investigated by examining F-actin levels in naïve and activated CD4$^+$ T and Jurkat cells. The amount of F-actin was reduced upon pretreatment of T cells with Salp15 (FIG. 3B and FIG. 7E). Flow cytometry analysis of F-actin formation in activated and naïve T cells using phalloidin$_{488}$ also revealed reduced F-actin content in cells pretreated with Salp15 (FIG. 3C). This effect was seen as early as 1 minute of activation further confirming that the primary signaling events upstream of lipid raft clustering were also affected by Salp15.

Example 4

CD4 Acts as the Specific Receptor for Salp15 on T Lymphocytes

Figures 4A, 4B, 4C, 4D:
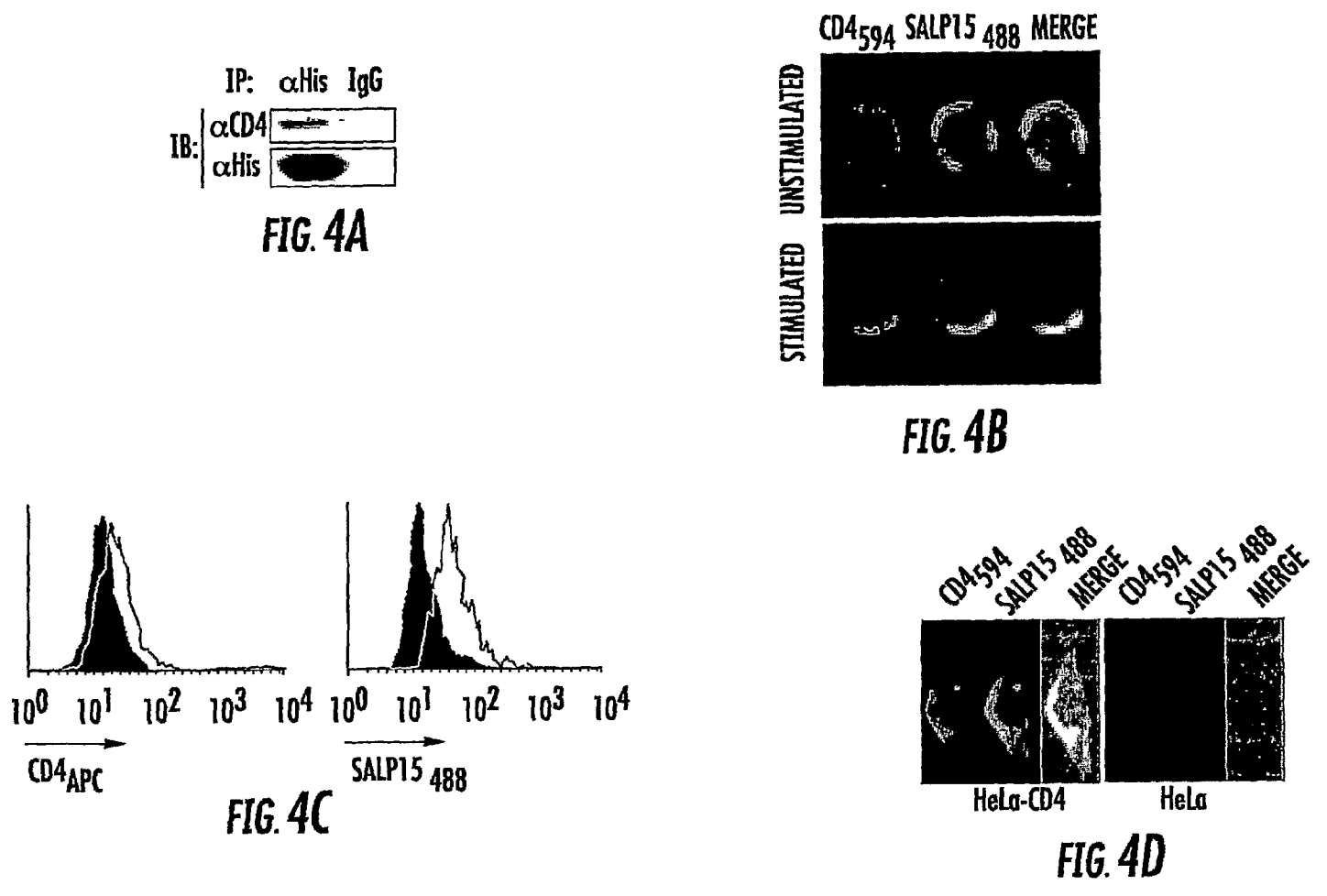
Figure 8B:
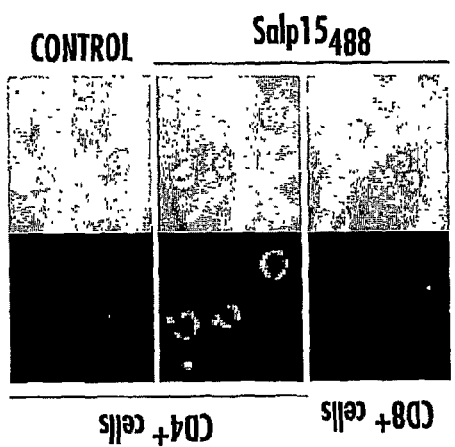
FIGS. 8A-8D show Salp15 binds specifically to CD4.
Figure 8D:
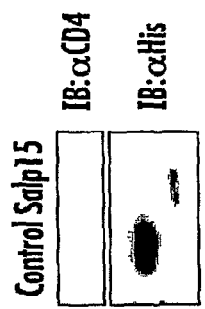
Figure 8A:
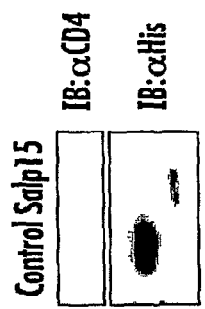

The inhibition of TCR-induced early signaling by Salp15 led to the investigation of the interaction of Salp15 with the key receptors involved in T cell signaling using coimmunoprecipitation methodologies. Salp15 co-immunoprecipitated the CD4 co-receptor (FIG. 4A) but not other key components of the T cell receptor complex, particularly TCRβ, CD3ε and CD28 from a Jurkat cell lysate (FIG. 8A). Further, Salp15 was found to bind specifically to CD4$^+$ T cells, while no staining of CD8$^+$ cells was detected by confocal microscopy (FIG. 8B). The simultaneous visualization of CD4 staining and Salp15 binding on unstimulated and activated CD4$^+$ T cells by confocal microscopy revealed the colocalization of both proteins on the plasma membrane (FIG. 4B).

Figure 4E:
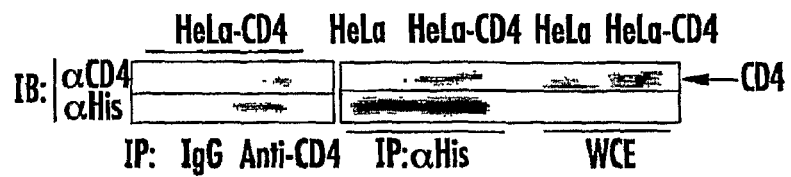
Figure 4F:
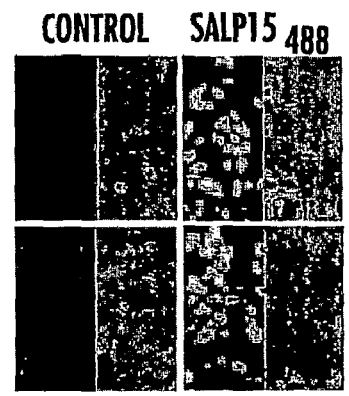
Figure 4G:
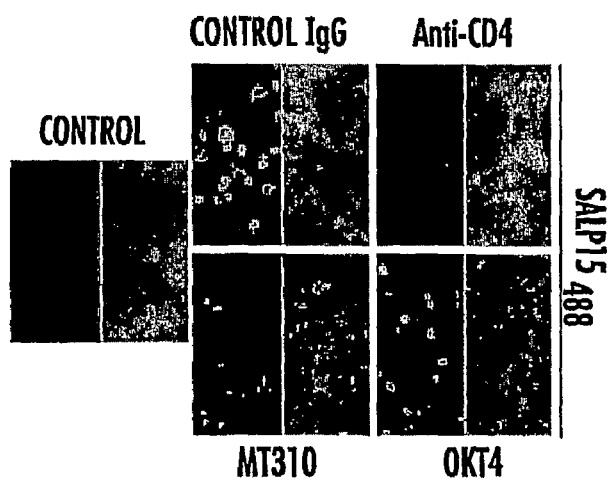
Figure 8C:
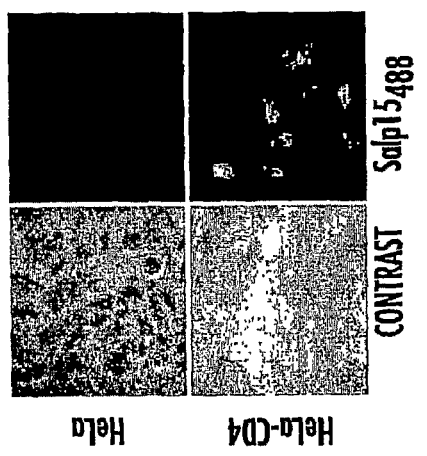

To further confirm this direct association, a non-lymphocyte cell line expressing CD4 was used. Flow cytometry analysis showed an increase in Salp15 binding to HeLa-CD4 cells compared to non-transfected controls (FIG. 4C). The analysis by confocal microscopy of Salp15 binding on HeLa and HeLa-CD4 cells revealed specific Salp15 binding on HeLa-CD4, but not in untransfected cells (FIG. 8C). Furthermore, CD4 staining colocalized with bound Salp15 on HeLa-CD4 cells (FIG. 4D). Co-immunoprecipitation experiments further confirmed the direct interaction of Salp15 with CD4 (FIG. 4E). Immunoprecipitation of a HeLa-CD4 cell lysate with Salp15 or a control His-tagged-thioredoxin-fused tick saliva protein (Salp13, Das et al, 2001) using an anti-His Ab showed specific immunoprecipitation of CD4 (FIG. 8D). Binding of Salp15$_{488}$ to HeLa-CD4 cells was competed by preincubating the cells with either unlabeled Salp15 or a polyclonal anti-CD4 antibody (FIG. 4F and FIG. 4G), substantiating the specificity of the interaction between Salp15 and CD4. The ability of two anti-CD4 mAbs, MT310 (CD4/V1-specific, Sutor et al., 1992) and OKT4 (CD4/D3-specific, Moore et al, 1992) to compete with Salp15$_{488}$ for binding to HeLa-CD4 cells was also investigated. Preincubation of HeLa-CD4 cells with mAb OKT4 failed to compete Salp15$_{488}$ binding, while MT310 showed competition with Salp15 staining (FIG. 4G).

To further substantiate the role of CD4-Salp15 interaction in the immunosuppressive effect of the tick saliva protein, splenic T cells from CD4-deficient mice were stimulated (McCarrick et al, 1993) with anti-CD3/CD28 in the absence or presence of Salp15. The immunosuppressive activity of Salp15 was highly diminished in T cells isolated from CD4-negative mice (33% inhibition) as compared to control T cells (85% inhibition, FIG. 9A). Without wishing to be bound by theory, these results indicate that the immunosuppressive action exerted by Salp15 is mediated through its specific interaction with the T cell co-receptor, CD4.

Example 5

The C-Terminal Peptide of Salp15 Associates with the Outer-Most Extracellular Domains of CD4

The binding of Salp15 with CD4 was next characterized. Salp15 showed a saturable binding to soluble (s) CD4 (containing the extracellular outer two domains, D1-D2) in a microtiter assay compared to a non-specific control (Lysozyme; FIG. 5A) with a dissociation constant (Kd) of 47 nM. Salp15 showed a saturable binding to a sCD4 preparation that contains all four extracellular domains (D1-D4) with a similar kinetics (FIG. 10A) in correlation with the observed competition with the CD4/D1-domain specific mAb MT310 (FIG. 4G).

Figure 11:
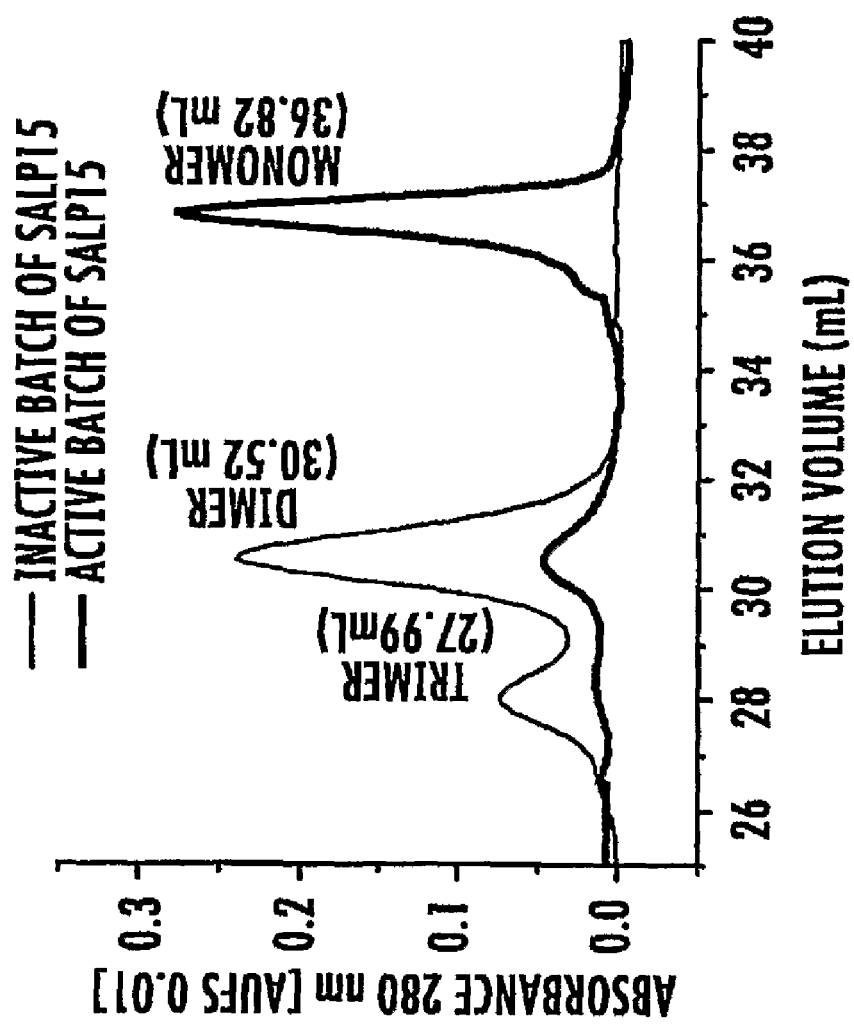
FIG. 11 is a graph showing the native gel filtration profile of Salp15. Active and inactive Salp15 was eluted through two superdex-200 gel filtration columns in tandem. The elution profile of active Salp15 (black line) contained predominantly a monomer fraction, while that of inactive Salp15 (gray line) contained dimer and trimer populations.

To further verify the interaction between Salp15 and sCD4, the gel filtration profile of a Salp15-CD4 solution was studied. two Superdex-200 gel filtration columns in tandem were employed to first study the elution profile of Salp15. The elution profiles of active Salp15 were markedly different from those of inactive preparations of the protein. Active Salp15 preparations consisted primarily of monomer fractions while inactive Salp15 forms contained predominantly dimer and trimer populations (FIG. 11). The gel filtration profile of sCD4 (D1-D4) contained a single peak corresponding to monomeric sCD4 (FIG. 5B). An additional peak overlapping with the sCD4 peak was observed in a Salp15-CD4 solution compared to the profiles of Salp15 and sCD4 alone (FIG. 5B). The overlapping peaks were resolved into individual peaks by Gaussian fit analysis, which showed the elution volume of the Salp15-CD4 complex to be 26.38 mL compared to 27.53 mL for the sCD4 peak (FIG. 5B). The calculated molecular weight of the Salp15-sCD4 complex was 67±8 kDa, suggesting that the molar ratio of Salp15-CD4 interaction is 1:1. The peak height of Salp15-CD4 was directly related to monomer content of Salp15 in different experiments. Another small peak seen at elution volume of 21.78 mL, which corresponded to an estimated molecular weight of 120 kDa (FIG. 5B) was not consistently observed.

The interaction of Salp15 with CD4 was also studied by native gel electrophoresis. Both sCD4 (D1-D4) and Salp15 co-migrated when allowed to interact in solution followed by gel electrophoresis under native conditions and Western blot analysis (FIG. 5C). Salp15 alone could not be visualized in the native gel together with sCD4 and sCD4-Salp15, probably due to a large difference in the mobility of Salp15 compared to those of sCD4 and sCD4-Salp15.

In order to map the residues in the immunomodulatory protein that interact with sCD4, synthetic 20 amino acid-long peptides with 10 amino acid overlaps spanning the entire Salp15 sequence (Table 1) were generated. Only the C-terminal peptide of Salp15 (P11, amino acids 95-114) showed binding to sCD4 (FIG. 6A). The binding was saturable, with a $K_d$ of 50 nM (FIG. 6B). P11 binding to sCD4 could be competed by adding increasing concentrations of the free peptide (IC50=1.25 μM; FIG. 10B), suggesting a specific interaction. The binding of P11 to sCD4 could also be competed by adding increasing concentrations of Salp15 (FIG. 6C). These data demonstrated that Salp15 binds to CD4 through its C-terminal residues.

In order to gain insight into the potential role of the cysteines present in Salp15 and P11 in their binding to CD4, two approaches were pursued. First, a shorter version of P11, P11-2 was used that contains 2 cysteines (amino acids 103-114 of the Salp15 sequence). This peptide also showed saturable binding with CD4 compared to a non-specific control (PLP, amino acids 139-151; FIG. 10C). Second, a CD4-binding microtiter assay was performed with plate-bound Salp15 that had been pre-treated with 10 mM DTT, which resulted in equivalent binding levels compared to CD4 binding to control Salp15 (FIG. 10D). The Ellman analysis of Salp15 showed that the molecule contains around 11% of free —SH groups, suggesting the presence of disulfide bonds that may involve an average of 6 of the 7 cysteines present in the molecule. Without wishing to be bound by theory, together these results suggest that even though the protein seems to contain several disulfide bonds, binding to CD4 is not mediated by their presence in the terminal portion of the molecule.

P11 was then tested for any immunosuppressive effects on T cell activation. The pretreatment of cells with P11 showed a dose dependent inhibition of $CD4^+$ T cell IL-2 production (FIG. 6D), while P8 (which showed no binding to CD4; FIG. 6B) did not exert any inhibition of T cell activation. To further confirm this effect, lipid raft reorganization in response to T cell activation was examined in cells pretreated either with P11 or P8. The pretreatment of cells with P11 caused a reduction in lipid rafts clustering while P8 did not show any effect (FIG. 6E). Thus, the C-terminal region of Salp15 is involved in its binding to CD4 as well as exerting immunomodulatory effects in T cells.

Discussion of Examples 1-5

CD4 plays a crucial role during T cell activation by facilitating the association of Lck with the CD3-TCR complex-associated ITAMS (Horejsi et al., 2004). The results disclosed in the Examples suggest that Salp15 treatment prior to T cell stimulation impedes the proper activation of the Src kinase Lck, which is considered almost the first protein to get phosphorylated during TCR signaling (Horejsi et al., 2004). Lck phosphorylation results in the activation of downstream proteins by its translocation to lipid rafts since a palmitoylated form of Lck which compartmentalizes constitutively in lipid rafts has been shown to induce constitutive activation of NF-AT and IL-2 production (Veri et al, 2001).

The results disclosed in the Examples have also confirmed that F-actin formation is reduced in activated T lymphocytes pretreated with Salp15. F-actin polymerization has been shown to be controlled by a number of stimuli such as Vav1, through the activation of the small GTPases Rac1 and cdc42 (Wulfing et al., 2000; Villalba et al., 2001). The guanine exchange factor activity of Vav1 is enhanced by its phosphorylation at several tyrosines through the Src family kinase Lck (Bustelo, 2000; Crespo et al., 1997; Riteau et al., 2003). The inhibition of TCR ligation-induced protein tyrosine phosphorylation including those of Lck and Vav1, by Salp15 pretreatment explains the defective actin polymerization during T cell activation and the improper lipid raft reorganization. Taken together, and without intending to be limited by theory, these observations suggest that Salp15 affects T cell activation at the very beginning of TCR signaling, likely at the level of membrane receptors involved in TCR signaling. Indeed, the Examples provide results showing that Salp15 interacts specifically with the CD4 co-receptor, while no interaction was detected between Salp15 and the TCR complex or the costimulatory molecule, CD28. Furthermore, Salp15 interacts with the extracellular outer two domains of CD4 through its C-terminal residues by a mechanism that is not likely to involve the several potential disulfide bonds found in the protein.

In contrast to co-engagement with the TCR, separate cross-linking of CD4 either by antibodies specific for particular CD4 epitopes or by its binding to HIV gp120 has been shown to inhibit or markedly modify the outcome of subsequent signals induced by TCR ligation (Bank and Chess, 1985; Harding et al., 2002). Similarly, the selective ligation of CD4 in vivo by specific antibodies in rodent models results in robust alloantigen-specific immunosuppression and induction of specific transplantation tolerance (Benjamin and Waldmann, 1986; Laub et al., 2002). $CD4^+$ T cell immunosuppression caused by Salp15 shared similarities with these described interactions, such as the inhibition of TCR induced tyrosine phosphorylation, calcium mobilization, NFAT and NF-κB activation that lead to IL-2 production.

However, Salp15 did not induce Lck phosphorylation in the absence of T cell stimulation, in contrast to the described effect of gp120 interacting with CD4 (Briand et al., 1997). Moreover, Salp15 does not affect AP-1 DNA binding activation (Anguita et al., 2002) compared to the ERK-mediated inhibition of AP-1 DNA binding activity observed in cells treated with gp120 (Jabado et al., 1997). Indeed, Salp15 does not affect AP-1 DNA binding activity T cells stimulated with lower doses of anti-CD3 (2.5 µg/ml versus 5 µg/ml), even though the effect of the Salp15 is strongly dependent on the strength of the signal provided to the activating T cells (Anguita et al., 2002), suggesting that this pathway is not affected by Salp15. While AP-1-mediated transcription is dependent on post-transcriptional modifications of its constituents, AP-1-mediated DNA binding activity does not require Tyr phosphorylation events (Rincón et al., 1994). Meanwhile, the TCR-mediated signals required for the binding activity of the complex remain unclear. PKC activation is sufficient to trigger AP-1 DNA binding (Rincón et al., 1994) and ERK activation seems to play an important role in the activation of the transcription factor through the expression of c-Fos and c-Jun (members of the AP-1 complex) (Chen and Davis, 2003; Cook et al., 1999). Unlike PLCγ1 activation, Salp15 does not impair ERK activation in response to anti-CD3/CD28 stimulation (FIG. 9B) in agreement with a lack of effect of the immunosuppressor on AP-1 DNA binding activity. Moreover, these data further discriminate the effect of Salp15 as compared to those of HIV gp120 and anti-CD4 cross-linking.

Since Salp15 interacts with the T cell co-receptor CD4 and inhibits the initiation of TCR-mediated signals by blocking the activation of Lck, it seems likely that CD4 mediates, either fully or at least in part, the inhibitory effect of Salp15 on T cell activation. Moreover, the results set forth in the Examples suggest that in T cells, the majority of the effect by Salp15 is mediated through its interaction with CD4. Compared to the effect of Salp15 on IL-2 production in control B6 mice, the effect in CD4-negative T cells was highly diminished. Furthermore, CD4-independent T cell responses such as INFγ-mediated phosphorylation of STAT1 were unaffected by Salp15 (FIG. 9C). The fact that the peptide corresponding to the C-terminal amino acid residues of Salp15, which shows strong binding to CD4, is capable of exerting the suppression of T cell activation further supports that CD4 mediates the inhibitory effect of Salp15 on T cells. Salp15 inhibits the activation of CD4+ T cells stimulated with anti-CD3/CD28, as well as through MHC II-CD4-dependent signals (FIG. 9D and FIG. 6), suggesting that the effect of the protein on T cell activation does not occur through interference with the interaction between MHC II and CD4, but rather with the interaction and proper alignment of CD4 with the TCR complex, which is critical for T cell activation. In this context, the following model is suggested, in view of the results disclosed in the Examples, for the immunosuppressive action of Salp15 on T cells. Upon contact with the membrane co-receptor CD4, Salp15 induces a conformational change in the receptor that blocks TCR-mediated Lck activation. This leads to the improper early activation of downstream signaling proteins resulting in defective F-actin polymerization and a reduction in the clustering of signaling proteins in lipid rafts, which are essential for the further amplification of cell signals that result in IL-2 production and T cell proliferation.

*I. scapularis* ticks have been shown to modulate the host immune response in many different ways, resulting in efficient transmission of several clinically important pathogens (Wikel, 1999). These data are the first known example of an interaction between an arthropod protein and a mammalian T cell co-receptor. This interaction clarifies the mechanism by which ticks withstand host immune responses during their encounter with the host. This helps ticks maintain their presence on the host and thereby be more potent vectors of a number of pathogens. Since the effect of Salp15 is not species specific, as it is evident in both mouse and human cells, Salp15 can be used in therapy of conditions characterized by CD4+ T cell responses, including autoimmune disorders and allogeneic transplant tolerance.

Examples 6 and 7

Modulation of Relapsing-EAE by Salp15

MS is a chronic inflammatory disease of the central nervous system CNS. Self-reactive T cell activation and innate immune cell activation are thought to be major eliciting factors for the appearance of the symptomatology associated with the damage of the myelin sheath. Evidence exists that point to reactivation of memory T cells and/or epitope spreading (i.e., neoautoreactivity) to explain the chronicity and the relapsing-remitting clinical course often associated with the disease.

The study of MS has advanced dramatically with the use of different rodent models, including rats and mice. The animals present with relapsing episodes that are at least partially due to epitope spreading, which gives rise to the activation of new CD4+ T cells recognizing other CNS peptides. Experiments carried out in the murine model have indicated that neoreactive CD4+ T cells are able to induce relapsing episodes. Therefore, the control of these relapsing episodes would provide a means to evade progression of disease. Thus, inhibition of T cell activation in response to relapsing-associated epitopes during remission of the acute phase of the disease can prevent the appearance of relapsing episodes.

Peptide specific disease therapy is difficult due to the diversity of peptides that can trigger relapsing episodes in humans. Alternative approaches include the inhibition of T cell activation using blocking antibodies to costimulatory molecules. As disclosed herein, Salp15 polypeptides can be utilized as a treatment for patients with MS.

As disclosed herein, a protein from tick saliva (Salp15) inhibits CD4+ T cell activation during encounter with the antigen, by preventing the production of the autocrine growth factor interleukin 2. Salp15 inhibits TCR-mediated Ca$^{2+}$ fluxes that lead to impaired activity of the transcription factor NF-AT, without affecting the activation of effector T cells. This protein can be used for the generation of immunotherapies aimed at the prevention and/or treatment of relapsing MS.

In order to further validate the beneficial effects of Salp15 in the prevention of relapsing episodes of MS a murine model of MS (R-EAE) is used. The model is used to assess the effect of Salp15 administration on epitope spreading during experimental induction of murine EAE and assess the effect of Salp15 on the clinical presentation of relapsing EAE.

Example 6

Effect of Salp15 Administration on Epitope Spreading During Experimental Induction of Murine EAE Salp15 inhibits naïve CD4+ T cell activation and therefore, it can reduce or even prevent neoreactivity during the course of disease, such as in MS for example. It has been demonstrated previously that epitope spreading has a role in relapsing episodes associated with R-EAE, an animal model of human MS. Salp15 is tested to determine if it reduces or even prevents the occurrence of activated CD4+ T cells in response to new epitopes (i.e. epitope spreading) during the course of experimental R-EAE.

salp15 was amplified from a pBluescript vector using specific primers: 5'-GAA AGC GGC CCA ACT AAA-3' (SEQ ID NO: 18) and 5'-CTA ACA TCC GGG AAT GTG-3' (SEQ ID NO: 19). The PCR product was subcloned into the pMT/BiP/V5-His A vector (Invitrogen, Carlsbad, Calif., U.S.A.) and transfected into Drosophila S2 cells (Invitrogen) in combination with the hygromycin selection vector pCOHYGRO, for stable transfection. The stable transformants were selected using 300 μg/ml hygromycin-B for 3-4 weeks. The resistant cells were grown as large spinner cultures, switched to DES serum-free medium for 2 days and induced with copper sulfate to a final concentration of 500 μM for 4 days. The cells were then centrifuged at 1,000×g for 5 minutes. The supernatant was used to purify the protein using the TALON™ metal affinity resin (Clontech, Palo Alto, Calif., U.S.A.). The protein was eluted using 100 mM imidazole, extensively dialyzed against PBS (pH 7.8) and concentrated by centrifugal filtration through a 10 kDa filter (Millipore Corp., Bedford, Mass., U.S.A.). The purity of the proteins was routinely checked on SDS-PAGE and for activity on a CD4+ T cell activation assay with anti-CD3/CD28 antibodies for 20-24 h.

SJL/J mice in groups of 18 are injected i.p. with 200 μg of PLP peptide 139-151 (HSLGKWLGHPDKF; SEQ ID NO: 15) (Research Genetics, Huntsville, Ala., U.S.A.). Please note that the original Cysteine has been substituted by serine for stability purposes. This change does not induce any alteration in the antigenicity of the peptide (Tuohy et al., 1989)) dissolved in an emulsion of 100 μL total volume of 60% Complete Freund's Adjuvant and 40% sterile normal saline. One group of mice receives daily injections of 50 μg of recombinant Salp15 produced in a Drosophila expression system, starting day 10 after immunization. This regime permits an efficient in vivo activation of $PLP_{139-151}$-specific CD4+ T cell activation. Since Salp15 has no effect on effector CD4+ T cells (Anguita et al., 2002.), its function is expected to be circumscribed to the activation of neoreactive CD4+ T cells. Another group of mice receives daily injections of PBS. Controls include a group of 3 animals that receive daily injections of Salp15 starting the day before immunization with $PLP_{139-151}$. This group serves as a positive control for Salp15 action and should prevent the activation of $PLP_{139-151}$-specific CD4+ T cells in vivo. The experiments are repeated at least twice to obtain statistically meaningful results.

At days 12 (including the 3 control mice treated with Salp15 over the course of the immunization), 14, 17, 20, 30 and 60 post-infection, 3 mice from each group are sacrificed and analyzed as follows: splenic CD4+ T cells are purified by negative selection using biotinylated antibodies against CD8a, Ly6G, Mac-I, B220, class II ($I-A^k$ and $I-E^k$) and panNK molecules (BD Biosciences Pharmingen, San Jose, Calif., U.S.A.), followed by incubation with Avidin bound to magnetic microbeads and passage through a magnetic column (Miltenyi Biotec, Auburn, Calif., U.S.A.). $10^6$ CD4+ T cells per ml are then incubated in the presence of 106 mitomycin C-treated (50 μg/ml, 37° C., 40 min) (Sigma Chemical Co., St. Louis, Mo., U.S.A.) syngeneic splenocytes with different peptides (10 μg/ml) that have previously shown reactivity in the murine model to assess the extent of epitope spreading in the relapse. These include: $PLP_{139-151}$ (immunization peptide), $PLP_{104-117}$, $PLP_{178-191}$ $MBP_{87-99}$ and $MOG_{92-106}$. These peptides include those that have been associated with relapses in SJL mice (Vanderlugt et al., 2000). T cells are analyzed for 1) proliferation by [$^3$H]-thymidine incorporation the last 18 hours of restimulation and 2) IFNγ, and IL-4 production at 40 h of restimulation, by ELISA. Antibodies specific for murine IFNγ, and IL-4 (BD Pharmingen), are used, following the manufacturer's instructions with some modifications. Briefly, 96 well ELISA plates (ICN, Costa Mesa, Calif., U.S.A.) are coated with the capture antibody (2 μg/ml) for 2 hours at 37° C. After blocking with PBS plus 10% FCS (PBS/FCS) overnight at 4° C., samples are applied and incubated 1 hour at 37° C. The biotinylated detection antibody (1 μg/ml) is added after washing the plates with PBS plus Tween 20 (0.5% v/v) (PBS/Tween). Quantitation of cytokine levels are made after incubating the plates with horseradish-conjugated avidin and adding the substrate for the enzyme (TMB, Kirkergaard and Perry Laboratories, Inc., Gaithersburg, Md., U.S.A.). Plates are read at 450 nm after stopping the color developing reaction (TMB 1-Component Stop Solution, Kirkergaard and Perry Laboratories, Inc., Gaithersburg, Md., U.S.A.). The values indicated are calculated comparing the values obtained with those derived using standard concentrations of recombinant mouse IFNγ, and IL-4 (BD Pharmingen).

Peripheral responses to relapsing epitopes are assessed by the analysis of delayed type hypersensitivity (DTH). Four and seven days of the initiation of the treatment with Salp15 or PBS in $PLP_{139-151}$-immunized mice, groups of 5 animals are challenged in the left ear with 10 μg of $PLP_{178-191}$, $PLP_{104-117}$, or $MBP_{87-99}$ and analyzed for swelling after 24 and 48 hours. Average thickness is compared to the non-challenged ear and control, non immunized mice and assessed statistical significance by comparison of the means with the Student T test.

The activity of Salp15 in vitro and in vivo suggests that the mice treated with the Salp15 protein will present lowered activation of CD4+ T cells in response to new epitopes arising during the course of experimental disease. In contrast, reactivity of CD4+ T cells to the immunizing peptide should remain intact, since Salp15 has no activity on effector T cells (Anguita et al., 2002.).

A potential side effect of Salp15 in the mouse to contemplate is the potential interference of Salp15 administration with selection processes of T cells in the thymus. In order to assess that the treatment with the protein does not have undesirable side effects on the T cell repertoire that would impair these mice to fight naturally occurring infections, thymic T cell populations are also analyzed. At the time of sacrifice, single cell suspensions of the thymi of the mice are obtained and analyzed for 1) total cell numbers by counting total thymocytes by trypan blue exclusion; 2) thymocyte subpopulations by FACS analysis of CD4+ and CD8+ single positive (SP), double positive (DP) and double negative (DN: $CD44^+$ $CD25^-$; $CD44^+CD25^+$; $CD44^-CD25^+$ and $CD44^-CD25$) populations. These thymic populations represent different stages in T cell development (from immature to mature: $DN$ $CD44^+CD25^- \rightarrow CD44^+CD25^+ \rightarrow CD44^-CD25^+ \rightarrow CD44^-$ $CD25^- \rightarrow DP \rightarrow SP$) and can provide clues as to whether Salp15 interferes with the generation of appropriate T cell repertoires; and 3) T (restimulation) and B cell (antibody production) responses to a foreign antigen (Keyhole Lympet Hemocyanin, KLH) of mice after 2 weeks of treatment with Salp15. The mice are treated for 2 weeks and immunized at the end of treatment with 10 μg of KLH in complete Freund's adjuvant (CFA). The purpose of these controls is to assure that the treatment does not impair the generation of appropriate T cell repertoires that could compromise immune responses to, for example, infectious agents.

Example 7

Effect of Salp15 on the Clinical Presentation of Relapsing EAE

Several lines of evidence point to a role of epitope spreading in MS progression. The treatment of mice with experimentally induced EAE with agents that block CD4+ T cell activation (CTLA4-Ig, anti-B7 antibodies) or the induction of tolerance to peptides that are recognized during the relapsing episodes in mice, alter progression of the disease and relapsing episodes (Vanderlugt et al., 2000; Karandikar et al., 2000; Miller et al., 1995). Some of these therapies are useful in the murine model, but difficult to apply in human disease because the exact nature of the antigens recognized during relapsing episodes is not known. Salp15 can reduce or even prevent epitope spreading during the course of experimental r-EAE and therefore, can reduce or even prevent progression of disease. In order to further demonstrate Salp15 can ameliorate experimental EAE, disease progression is analyzed in SLJ mice that are treated with the immunosuppressive Salp15 protein.

SJL mice in groups of 10 are immunized with $PLP_{139-151}$, as before in Example 6. The animals are monitored for the appearance and remission of the typical paralyzing symptoms. Mice are observed daily for clinical symptoms and scored as follows: 0, no evident disease; 1, loss of tail tone; 2, hind limb weakness; 3, paralysis of both hind limbs; 4, moribund state/death. Mice with intermediate clinical symptoms are scored in 0.5 increments. The results are tabulated for statistical analysis. All the observations are carried out at the same time of day (in the morning). If a mouse shows a grade of 4, the animal is euthanized, as per IACUC recommendations. Clinical remission is defined as an improvement of at least one full clinical score that is sustained for at least two consecutive days.

Three days after the establishment of clinical remission, the mice are divided in 2 groups. One group is treated with recombinant Salp15 every day by i.p. injection (50 µg/mouse). The control group is treated with PBS. The animals are continuously monitored during 21 days for relapses. A clinical relapse is defined as an increase of at least one full clinical score sustained for at least 2 consecutive days. The scores are tabulated and the groups compared for statistical significance.

The progression of disease is also evaluated by histological examination of brains and spinal cords of immunized, treated and control mice. Groups of 3 mice are sacrificed after 7, 14 and 21 days of treatment with Salp15. Brains and spinal cords are fixed in formalin and embedded in paraffin. Sections are then obtained and pretreated with 0.04% $OsO_4$ and 1% $H_2O_2$ in 10% Triton X-100. The sections are then blocked with normal goat serum and treated sequentially with a PLP monoclonal antibody (Harlan, Indianapolis, Ind., U.S.A.) and a peroxidase-labeled anti-mouse IgG antibody. The preparations will then be treated with diaminobenzidine and 0.01% $H_2O_2$, 0.04% $OsO_4$ followed by washing with PBS. The sections are analyzed by microscopy.

Salp15 is a protein that can repress the activation of CD4+ T cells, including new epitopes that arise during experimental EAE. Epitope spreading has been associated with relapsing episodes in rodents and potentially in humans. Salp15 is expected to inhibit the appearance of relapsing episodes in mice experimentally induced EAE. It is also expected that a lower degree of demyelination as a result of treatment with Salp15 can be found, which would indicate that the treatment is able to prevent the progression of disease in the mice.

The use of *Bordetella pertussis* toxin for the induction of the disease in mice, a common procedure for the induction of EAE in rodents is purposely omitted. However, SJL mice develop R-EAE in the absence of the toxin shortly after immunization with the eliciting peptide (Karandikar et al., 2000; Theien et al., 2001). Therefore, studies are conducted without the toxin. Nevertheless, studies in groups of mice treated with this eliciting agent can be performed.

Example 8

Salp15 Competes with HIV gp120 for Binding to CD4

Ninety-six (96) well plates were coated with 0.05 uM sCD4 (D1-D2 domains) in coating buffer (pH 9.6). The plates were washed 2× and blocked with 200 uL of PBS+10% FCS. Samples were then added containing gp120-HRP plus 0, 0.05, 0.5 and 5 uM Salp15 in PBS+10% FCS. KLH was used as negative control at 5 uM. The plates were incubated for 2 hours at room temperature and washed 4×, followed by incubation with horseradish peroxidase substrate and stop solution from KPL.

Figure 12:
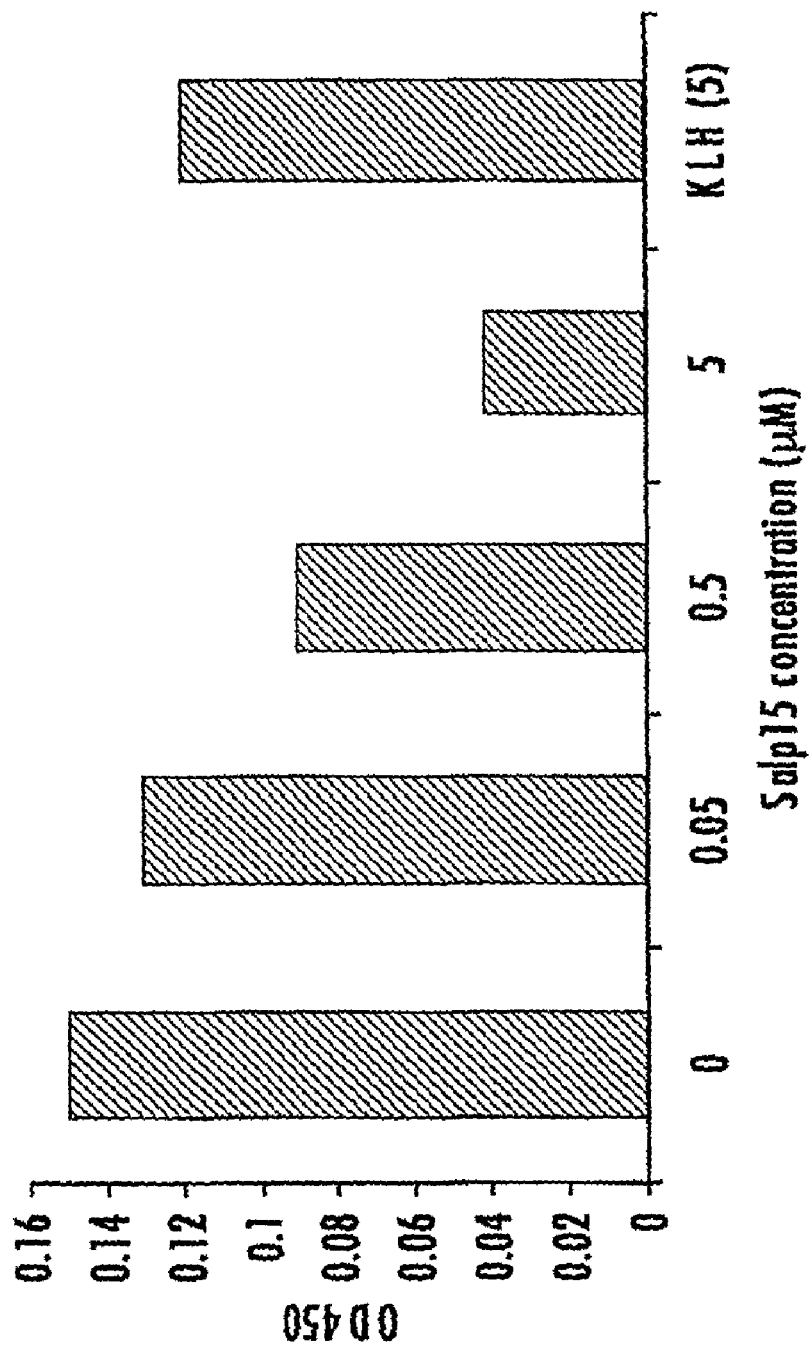
FIG. 12 is a graph showing Salp15 effects on CD4-gp120 binding in vitro.

Results are shown in FIG. 12 and demonstrate a concentration dependent inhibition by Salp15 of gp120 binding to CD4. These results indicate that Salp15 binds to a region in the CD4 molecule that overlaps with the binging site for gp120.

Example 9

Salp15 Effect on gp120-CD4-Mediated Cell Fusion by Luciferase Assay

106 HeLa-CD4 cells, clone 1022 (NIH AIDS Research & Reference Reagent Program, Germantown, Md., U.S.A.) were plated in a 6-well plate and transfected with the plasmid Blue 3' LTR-luciferase (NIH AIDS Research & Reference Reagent Program) using the lipofectamin method (Invitrogen).

After 24 hours, the cells were trypsinized and mixed with HL2/3 cells that express HIV envelope proteins (NIH AIDS Research & Reference Reagent Program), encoding Gag, Nef, Rev, Tat and Env proteins from HIV (0.2×106 HeLa-CD4+0.2×106 HL2/3) in a 24-well plate at a final volume of 500 uL. The cells were incubated in the presence of 10 and 50 ug/ml of Salp15. The positive control was anti-CD4 Ab and the negative control was anti-CD3.

The cells were harvested after 48 hours, washed with PBS and lysed with 100 uL of Passive Lysis buffer (Promega) per well, for 15 min at RT. The lysates were transferred to Eppendorf tubes, spun at 10,000×g and assessed for Luciferase activity and protein content by the Bradford assay (BioRad). Luciferase activity is an indicator of cell fusion mediated by the interaction of HIV envelope proteins on HL2/3 cells and CD4 on HeLa-CD4 cells.

Figure 13:
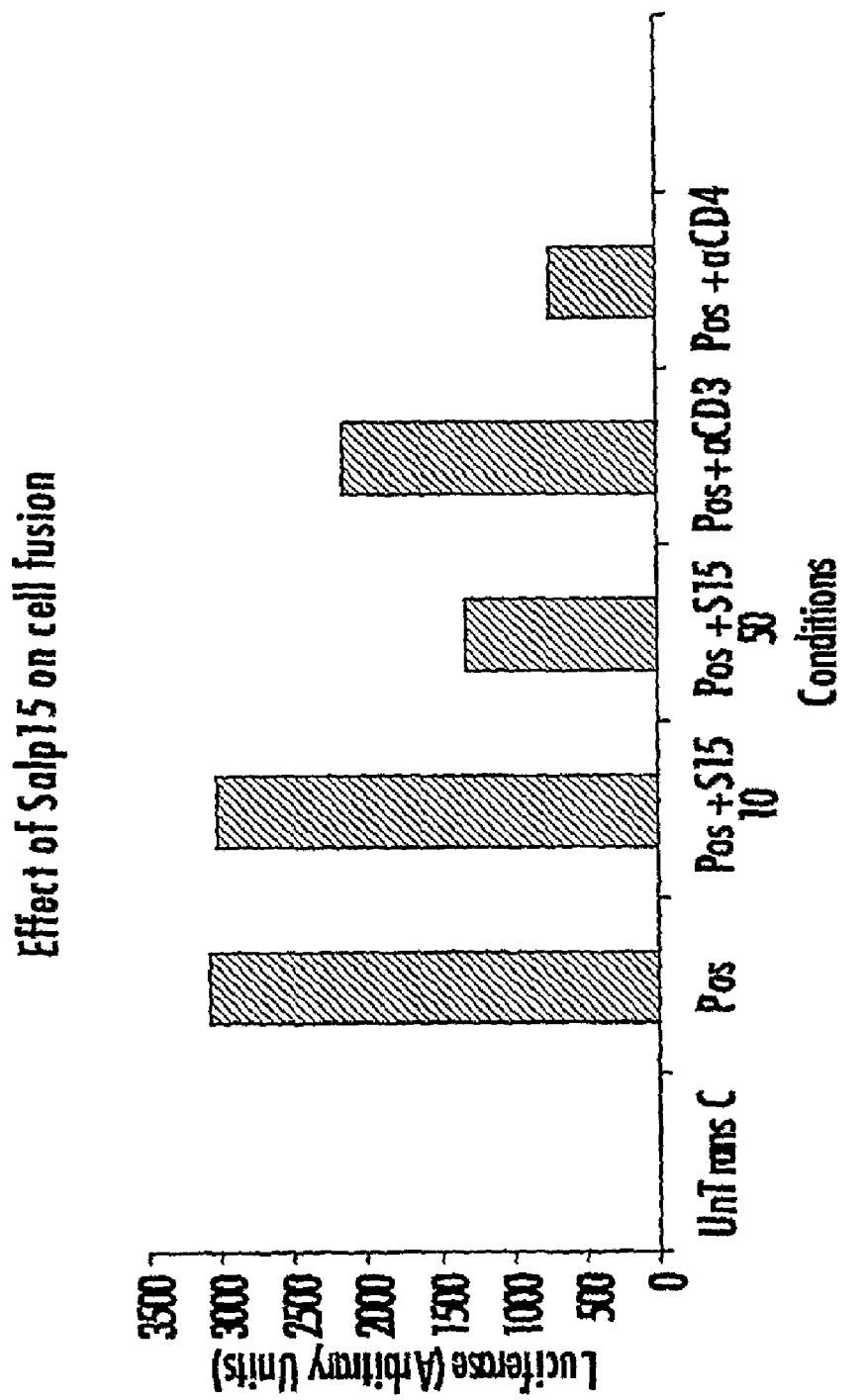
FIG. 13 is a graph showing effects of Salp15 on blocking fusion of cells expressing either HIV envelope proteins or CD4.

Results are shown in FIG. 13 demonstrating a concentration dependent reduction in cell fusion by Salp15. These data demonstrate Salp15 interferes with fusion of cells expressing gp120 with cells expressing CD4 through interference of the Salp15 protein with gp120 binding to CD4.

REFERENCES

The publications and other materials listed below and/or set forth by author and date in the text above to illuminate the presently disclosed subject matter, and in particular cases, to provide additional details respecting the practice, are incorporated herein by reference. Materials used herein include but are not limited to the following listed references.

Adelman et al. (1983). *DNA* 2:183.
Alonso et al. (2004). *J. Biol. Chem.* 279:4922-4928.
Alonso and Millan (2001). *J. Cell. Sci.* 114:3957-3965.
Altschul et al. (1990). *J Mol Biol* 215:403-410.
Andersson et al. (2000). *Biopolymers* 55:227-250.
Anguita et al. (2002). *Immunity* 16:849-859.
Bank and Chess (1985). *J. Exp. Med.* 162:1294-1303.
Benjamin and Waldmann (1986). *Nature* 320:449-451.
Berkow et al. (1997). *The Merck Manual of Medical Information*, Home ed. Merck Research Laboratories, Whitehouse Station, N.J.
Bodanszky (1993). *Principles of Peptide Synthesis*, 2nd rev. ed. Springer-Verlag, Berlin/New York.
Bolen and Brugge (1997). *Annu. Rev. Immunol.* 15:371-404.
Briand et al. (1997). *Virology* 228:171-179.
Burgdorfer et al. (1982). *Science* 216:1317-1319.
Bustelo (2000). *Mol. Cell. Biol.* 20:1461-1477.
Chen and Davis (2003). *Mol. Cell. Endocrinol* 200:141-154.
Chen et al. (1994). *J. Clin. Microbiol.* 32:589-595.
Cook et al. (1999). *Mol. Cell. Biol.* 19:330-341.
Corringer et al. (1993). *J. Med. Chem.* 36:166-172.
Dalgleish et al. (1984). *Nature* 312:763.
Crespo et al. (1997). *Nature* 385:169-172.
Das et al. (2001). *J. Infect. Dis.* 184:1056-1064.
Duch et al. (1998). *Toxicol. Lett.* 100-101:255-263.
Ebadi (1998). *CRC Desk Reference of Clinical Pharmacology*. CRC Press, Boca Raton, Fla.
Ferreira and Silva (1998). *Vet. Immunol. Immunopathol.* 64:279-293.
Fields and Noble (1990). *Int J Pept Protein Res* 35:161-214.
Fleury et al. (1991). *Cell* 66(5):1037-1049.
Freireich et al. (1966). *Cancer Chemother. Rep.* 50:219-244.
Garbay-Jaureguiberry et al. (1992). *Int J Pept Protein Res* 39:523-527.
Goodman et al. (1996). *Goodman & Gilman's the Pharmacological Basis of Therapeutics*, 9th ed. McGraw-Hill Health Professions Division, New York.
Goverman and Brabb (1996). *Lab. Anita. Sci.* 46:482.
Gribskov et al. (1986). *Nuc Acids Res* 14(1):327-334.
Harding et al. (2002). *J. Immunol.* 169:230-238.
Horejsi et al. (2004). *Nat. Rev. Immunol.* 4:603-616.
Huang et al. (2000). *Proc. Natl. Acad. Sci. USA* 97:10923-10929.
Janes et al. (2000). *Semin. Immunol.* 12:23-34.
Karandikar et al. (2000). *J. Neuroimmunol.* 109:173.
Katzung (2001). *Basic & Clinical Pharmacology*, 8th ed. Lange Medical Books/McGraw-Hill Medical Pub. Division, New York.
Kopecky and Kuthejlova (1998). *Parasite Immunol.* 20:69-74.
Koretzky et al. (2003). *Immunol. Res.* 27:357-366.
Krishnan et al. (2004). *J. Immunol.* 172:7821-7831.
Kuchroo et al. (2002). *Annu Rev Immuno.* 120:101.
Kyte et al. (1982). *J Mol Biol* 157:105.
Laub et al. (2002). *J. Immunol.* 169:2947-2955.
Lehmann et al. (1992). *Nature* 358:155.
Lehrnann et al. (1993). *Immunol. Today* 14:203.
Maddon et al. (1986). *Cell* 46:333-348.
McCarrick et al. (1993). *Transgenic Res.* 2:183-190.
McDougal et al. (1986). *Science* 231:382.
McOmie (1973). *Protective Groups in Organic Chemistry*, Plenum Press, London/New York.
McRae et al. (1992). *J Neuroimmuno* 138:229.
McRae et al. (1995). *J Exp Med* 182:75.
Merrifield (1969). *Adv. Enzymol. Relat. Areas Mol. Biol.* 32:221-296.
Michel et al. (1998). *J. Biol. Chem.* 273:31932-31938.
Miller et al. (1995). *Immunity* 3: 739.
Moore et al. (1992). *J. Virol.* 66:4784-4793.
Motameni et al. (2004). *Infect. Immun.* 72:3638-3642.
Mustelin et al. (1990). *Science* 247:1584-1587.
Myung et al. (2000). *Curr. Opin. Immunol.* 12:256-266.
Needleman et al. (1970). *J Mol Biol* 48:443.
Pavone et al. (1993). *Int J Pept Protein Res* 41:15-20.
PCT International Publication No. WO 93/25521.
Qian and Weiss (1997). *Curr. Opin. Cell Biol.* 9:205-212.
Ramamoorthi et al. (2005). *Nature* 436:573-577.
Remington et al. (1975). *Remington's Pharmaceutical Sciences*, 15th ed. Mack Pub. Co., Easton, Pa.
Rhee and Bae (1997). *J. Biol. Chem.* 272:15045-15048.
Ribeiro et al. (1995). *Biochem. J.* 308:243-249.
Rincon and Flavell (1994). *EMBO J.* 13:4370-4381.
Riteau et al. (2003). *J. Exp. Med.* 198:469-474.
Rodgers and Rose (1996). *J. Cell. Biol.* 135:1515-1523.
Sambrook et al. (2001). *Molecular Cloning: A Laboratory Manual*, Third Edition, Cold Spring Harbor Laboratory Press, Cold Spring Harbor, N.Y.
Schneider and Eberle (1993). *Peptides, 1992: Proceedings of the Twenty-Second European Peptide Symposium*, Sep. 13-19, 1992, Interlaken, Switzerland. Escom, Leiden.
Schoeler et al. (1999). *Exp. Parasitol.* 92:239-248.
Schröder and Lübke (1965). *The Peptides*. Academic Press, New York, United States of America.
Schwartz et al. (1979). *Nuc Acids Res* 6(2):745-755. Simons and Ikonen (1997). *Nature* 387:569-572.
Smith et al. (1981). *Adv Appl Math* 2:482.
Speight et al. (1997). *Avery's Drug Treatment: A Guide to the Properties, Choice, Therapeutic Use and Economic Value of Drugs in Disease Management*, 4th ed. Adis International, Auckland/Philadelphia.
Stewart and Young (1969). *Solid Phase Peptide Synthesis*, Freeman, San Francisco.
Sutor et al. (1992). *J. Immunol.* 149:1452-1461.
Theien et al. (2001). *J. Clin. Invest.* 107:995.
Thompson et al. (1994), *Nucleic Acids Res* 22(22):4673-4680.
Tran et al. (2002). *J. Immunol.* 168:4293.
Tung et al. (1992). *Pept. Res.* 5:115-118.
Tuohy et al. (1989). *J. Immunol.* 142:1523.
Urge et al. (1992). *Carbohydr. Res.* 235:83-93.
Urioste et al. (1994). *J. Exp. Med.* 180:1077-1085.
U.S. Pat. No. 4,244,946.
U.S. Pat. No. 4,554,101.
U.S. Pat. No. 5,234,933.
U.S. Pat. No. 5,326,902.
U.S. Pat. No. 5,578,629.
U.S. Pat. No. 5,811,392.
U.S. Pat. No. 5,811,512.
U.S. Pat. No. 5,811,515.
U.S. Pat. No. 5,817,757.
U.S. Pat. No. 5,817,879.
U.S. Pat. No. 5,834,228.
U.S. Pat. No. 5,872,011.
U.S. Pat. No. 6,015,561.
U.S. Pat. No. 6,015,881.
U.S. Pat. No. 6,031,071.
U.S. Pat. No. 6,180,082.
Valensin et al. (2002). *Eur. J. Immunol.* 32:435-446.
Vanderlugt et al. (2000). *J. Immunol.* 164:670.
Veri et al. (2001). *Mol. Cell. Biol.* 21:6939-6950.

Villalba et al. (2001). *J. Cell. Biol.* 155:331-338.
Viola et al. (1999). *Science* 283:680-682.
Wethmur & Davidson (1968). *J Mol Biol* 31:349-370.
Wikel (1999). *Int. J. Parasitol.* 29:851-859.
Wikel and Bergman (1997). *Parasitol. Today* 13:383-389.
Wulfing (2000). *Proc. Natl. Acad. Sci. USA.* 97:10150-10155.

Yu et al. (1996). *J. Exp. Med.* 183:1777.
Zhang and Samelson (2000). *Semin. Immunol.* 12:35-41.

It will be understood that various details of the presently disclosed subject matter may be changed without departing from the scope of the presently disclosed subject matter. Furthermore, the foregoing description is for the purpose of illustration only, and not for the purpose of limitation.

---

What is claimed is:

1. A method of treating a subject suffering from or at risk of suffering from a condition characterized by a CD4+ T cell response, comprising administering to the subject an effective amount of a Salp15 polypeptide, wherein the Salp15 polypeptide consists of the amino acid sequence of SEQ ID NO: 13 or SEQ ID NO: 14.

2. The method of claim 1, wherein the condition is an autoimmune disorder or a tissue or organ transplant rejection.

3. The method of claim 2, wherein the condition is an autoimmune disorder selected from the group consisting of lupus, rheumatoid arthritis, type 1 diabetes, multiple sclerosis, rheumatic fever, and Hashimoto's disease.

4. The method of claim 1, wherein the polypeptide is administered by systemic administration, parenteral administration, oral delivery, buccal delivery, subcutaneous administration, inhalation, intratracheal installation, surgical implantation, transdermal delivery, local injection, and hyper-velocity injection/bombardment, or combinations thereof.

5. A method of treating multiple sclerosis in a subject, comprising administering to the subject an effective amount of a Salp15 polypeptide consisting of the amino acid sequence of SEQ ID NO: 13 or SEQ ID NO: 14.

6. The method of claim 5, wherein the Salp15 polypeptide is administered by systemic administration, parenteral administration, oral delivery, buccal delivery, subcutaneous administration, inhalation, intratracheal installation, surgical implantation, transdermal delivery, local injection, and hyper-velocity injection/bombardment, or combinations thereof.

7. The method of claim 5, wherein the Salp15 polypeptide is encoded by SEQ ID NO: 16 or SEQ ID NO: 17.

8. The method of claim 5, wherein treating the multiple sclerosis comprises treating a relapsing episode of multiple sclerosis resulting from epitope spreading.

* * * * *